United States Patent
Danielsen et al.

(10) Patent No.: US 9,562,258 B2
(45) Date of Patent: *Feb. 7, 2017

(54) SEQUENCE-SPECIFIC DETECTION OF NUCLEOTIDE SEQUENCES

(71) Applicant: Georgetown University, Washington, DC (US)

(72) Inventors: Mark Danielsen, Germantown, MD (US); Joel Credle, Washington, DC (US); Eugene A. Davidson, Boynton Beach, FL (US); Kenneth L. Dretchen, North Potomac, MD (US)

(73) Assignee: Georgetown University, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/170,667

(22) Filed: Feb. 3, 2014

(65) Prior Publication Data

US 2014/0256577 A1 Sep. 11, 2014

Related U.S. Application Data

(60) Division of application No. 13/202,887, filed as application No. PCT/US2010/000527 on Feb. 23, 2010, now abandoned, application No. 14/170,667, which is a continuation-in-part of application No. 11/884,366, filed as application No. PCT/US2006/005248 on Feb. 15, 2006, now Pat. No. 9,012,142.

(60) Provisional application No. 61/154,737, filed on Feb. 23, 2009, provisional application No. 60/758,196, filed on Jan. 12, 2006, provisional application No. 60/652,743, filed on Feb. 15, 2005.

(51) Int. Cl.
C12Q 1/68 (2006.01)
C12Q 1/70 (2006.01)

(52) U.S. Cl.
CPC ............ *C12Q 1/6823* (2013.01); *C12Q 1/689* (2013.01); *C12Q 1/6837* (2013.01); *C12Q 1/6888* (2013.01); *C12Q 1/701* (2013.01)

(58) Field of Classification Search
None
See application file for complete search history.

(56) References Cited

U.S. PATENT DOCUMENTS

| | | | |
|---|---|---|---|
| 5,011,769 A * | 4/1991 | Duck et al. | 435/6.12 |
| 5,656,430 A | 8/1997 | Chirikjian et al. | |
| 5,763,178 A | 6/1998 | Chirikjian et al. | |
| 5,763,181 A | 6/1998 | Han et al. | |
| 5,846,726 A | 12/1998 | Nadeau et al. | |
| 6,191,267 B1 | 2/2001 | Kong et al. | |
| 6,280,949 B1 * | 8/2001 | Lizardi | 435/6.18 |
| 6,395,523 B1 | 5/2002 | Kong et al. | |
| 6,548,247 B1 | 4/2003 | Chirikjian et al. | |
| 6,787,304 B1 | 9/2004 | Han et al. | |
| 6,884,586 B2 | 4/2005 | Van Ness et al. | |
| 7,112,422 B2 | 9/2006 | Han et al. | |
| 7,112,423 B2 | 9/2006 | Van Ness et al. | |
| 2003/0219804 A1 | 11/2003 | Nerenberg et al. | |
| 2004/0048257 A1 | 3/2004 | Liu | |
| 2004/0142369 A1 | 7/2004 | Alajem et al. | |
| 2005/0214809 A1 | 9/2005 | Han | |
| 2005/0287560 A1 * | 12/2005 | Garimella et al. | 435/6 |
| 2006/0259249 A1 | 11/2006 | Sampath et al. | |

FOREIGN PATENT DOCUMENTS

| | | |
|---|---|---|
| WO | WO 89/10415 | 11/1989 |
| WO | WO 96/01836 A1 | 1/1996 |
| WO | WO 03/008623 A2 | 1/2003 |
| WO | WO 03/083137 A2 | 10/2003 |
| WO | WO 2004/022701 A2 | 3/2004 |
| WO | WO 2005/052127 A2 | 6/2005 |
| WO | WO 2006/088910 A2 | 8/2006 |

OTHER PUBLICATIONS

Lanciotti et al., Journal of Clinical Microbiology, 1992, vol. 30 pp. 545-551.*
Epstein et al., Analytica Chimica Acta, 2002, vol. 469 pp. 3-36.*
Kiesling et al., Nucleic Acids Research, 2007, vol. 35 e117, pp. 1-9.*
Cairns et al., Biochemical and Biophysical Research Communications, 318(3):684-90 (2004).
Constantine and Harrington, Life Science News, pp. 11-14 (1998).
Data sheet N.BstNBI—New England Biolabs, down loaded from the internet [www.neb.com], pp. 1-3, printed on Jan. 2, 2014.
De Preter et al., Cancer Letters, 197:53-61 (2003).
European Search Report, Application No. 10 74 4083, dated Oct. 25, 2012.
Gao et al., Diagnostic Microbiology and Infectious Disease, vol. 60, pp. 133-141, Published online Oct. 30, 2007.
GeneChip Human Genome U133 Set, Internet Citation XP002232760 (2003).
Human Genome U95Av2, Internet Citation XP002215481 (2002).
IDT Manual, Strategies for Attaching Oligonucleotides to Solid Supports, Integrated DNA Technologies, pp. 1-22 (2005).

(Continued)

*Primary Examiner* — Mindy G Brown
(74) *Attorney, Agent, or Firm* — RatnerPrestia

(57) ABSTRACT

A method for detecting the presence of a target nucleotide sequence in a sample of DNA is described herein in which a test sample comprising single stranded DNA is exposed to a DNA probe and a nicking endonuclease under conditions that would permit sequence-specific hybridization of the probe to a complementary target sequence. The probe comprises a sequence complementary to the target sequence to be detected and this sequence also includes a recognition sequence for the nicking endonuclease. If the sample contains the target sequence, the probe hybridizes to the target and is cleaved by the nicking endonuclease, which leaves the target intact. Observing the presence of probe cleaved by the nicking endonuclease indicates the presence of the target nucleotide sequence in the sample of DNA.

11 Claims, 50 Drawing Sheets

(56) References Cited

OTHER PUBLICATIONS

International Search Report (PCT/ISA/210) issued on Aug. 11, 2010 for International Application No. PCT/US2010/000527.
Jia et al., Journal of RNAi and Gene Silencing, vol. 3, pp. 248-253 (2007).
Kane et al., Nucleic Acids Research, vol. 28, pp. 4552-4557 (2000).
Kiesling et al., Nucleic Acids Research, 35(18):E117.1-E117.9 (2007).
Li et al., Analytical Chemistry, vol. 29, pp. 1050-1056 (2007).
Magnusson et al., Biomed Central, 6(1):310-22 (2005).
PCT/US06/05248 International Search Report mailed Jul. 9, 2008 by Narayan K. Bhat.
Schoske et al., Anal. Bioanal. Chem., 375:333-43 (2003).
Stappert et al., Nucleic Acids Research, vol. 20, p. 624 (1991).
Stephens et al., Science, 282:754-59 (1998).
Tyagi and Kramer, Nature Biotechnology, 14:303-08 (1996).
Xu et al., PNAS, vol. 98, (23):12990-995 (2001).
European Observation Report by Third Party dated Sep. 9, 2015 in European Application No. 10744083.6.
Ghosh and Musso, Nucleic Acids Research, 15(13):5353-72 (1987).
Lund et al., Nucleic Acids Research, 16(22):10861-80 (1988).
Nikiforov and Rogers, Analytical Biochemistry, 227:201-9 (1995).
European Examination Report dated Aug. 21, 2015 in European Application No. 10744083.6.

* cited by examiner

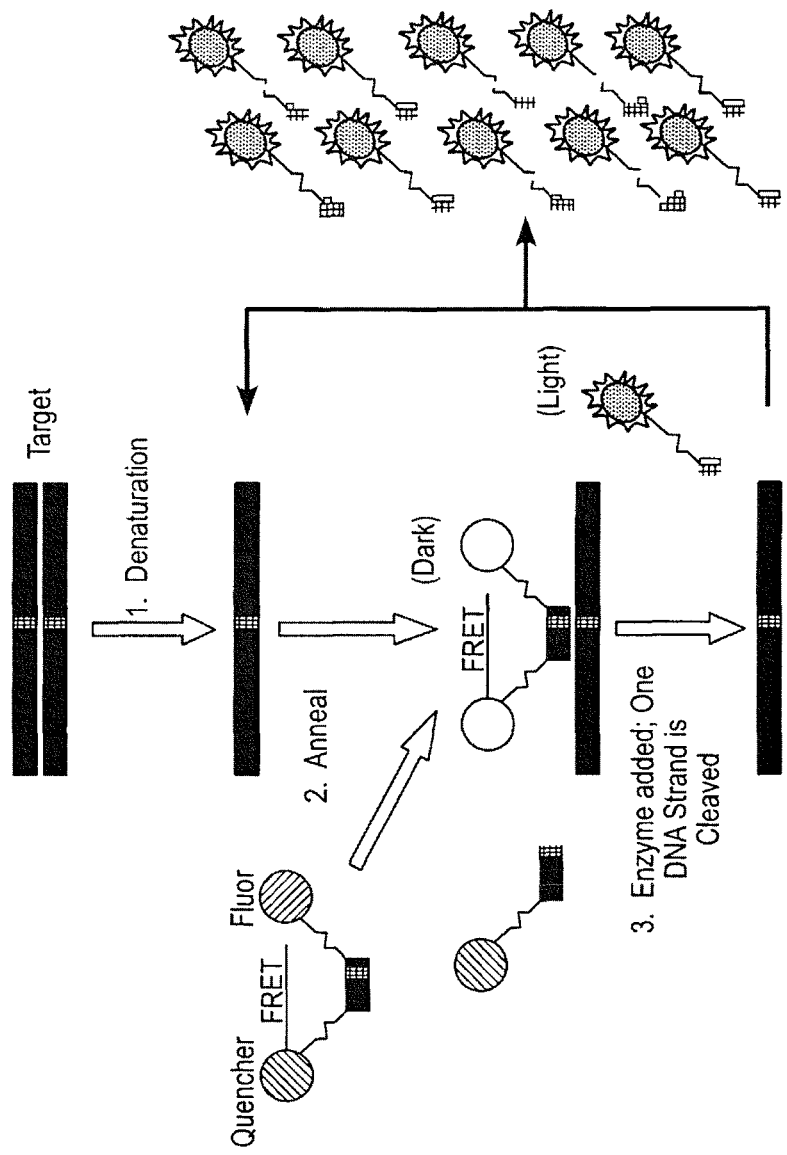

| Temperature °C | 50 | 55 | 56 | 57 | 58 | 59 | 60 | 60.6 | 62.5 |
|---|---|---|---|---|---|---|---|---|---|
| E.coli (wt) Elc | | | | | | | | | |
| B. subtilis (wt) Blc | | | | | | | | | |

| 16 S DNA | Mutation | Probe | 50 | 55 | 56 | 57 | 58 | 59 | 60 | 60.6 | 62.5 |
|---|---|---|---|---|---|---|---|---|---|---|---|
| T | A | Elc m1 | | | | | | | | | |
| G | C | Elc m2 | | | | | | | | | |
| G | C | Elc m3 | | | | | | | | | |
| C | G | Elc m4 | | | | | | | | | |
| A | T | Elc m5 | | | | | | | | | |
| T | A | Elc m6 | | | | | | | | | |
| T | A | Elc m7 | | | | | | | | | |
| C | G | Elc m8 | | | | | | | | | |
| T | A | Elc m9 | | | | | | | | | |
| G | C | Elc m10 | | | | | | | | | |
| A | T | Elc m11 | | | | | | | | | |
| T | A | Elc m12 | | | | | | | | | |
| C | G | Elc m13 | | | | | | | | | |
| C | G | Elc m14 | | | | | | | | | |
| A | T | Elc m15 | | | | | | | | | |
| C | G | Elcmp m16 | | | | | | | | | |

FIG. 6

Stem-Loop Fluor-Quench Probe Design

— Sequence matching target sequence

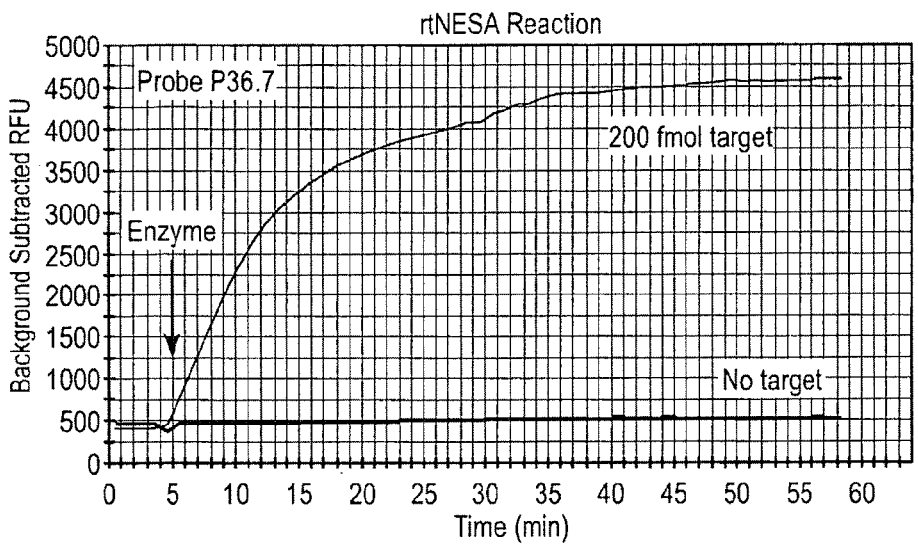
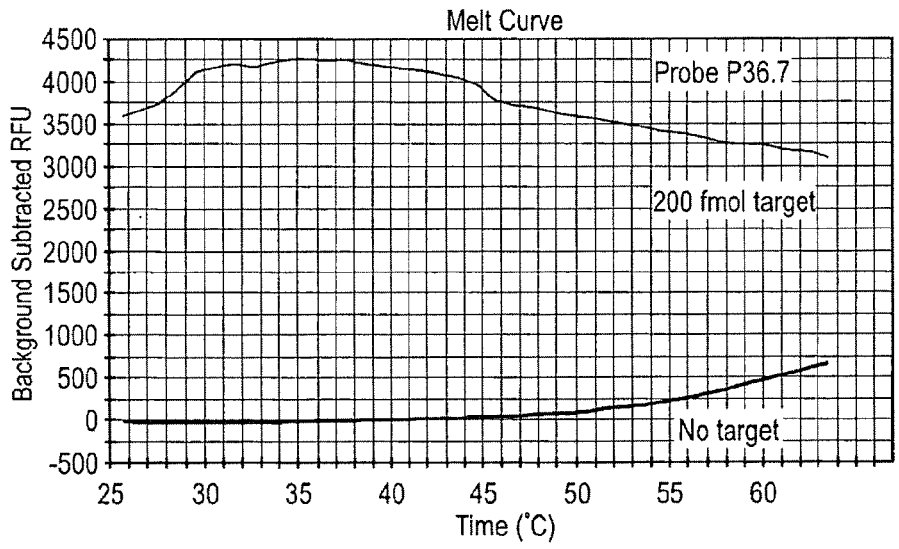
FIG. 22

Efficiency of coupling reaction to beads
(A) Table and standard curve generated from DNase treated serial dilutions of unbound probe and of bound probes.
(B) Table of calculated values of probe molecules per bead.

FIG. 35

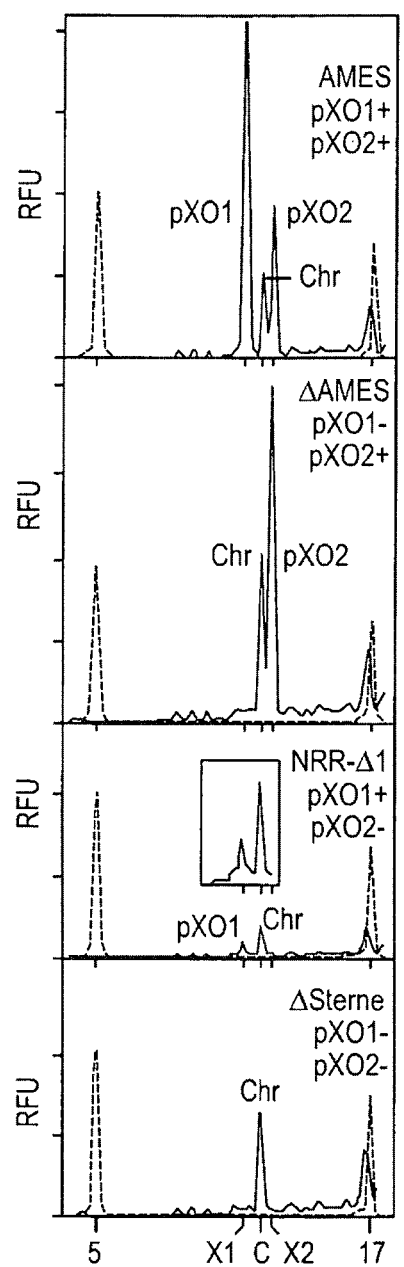

US 9,562,258 B2

SEQUENCE-SPECIFIC DETECTION OF NUCLEOTIDE SEQUENCES

CROSS REFERENCE TO RELATED APPLICATIONS

This application is a divisional application of U.S. National Phase application Ser. No. 13/202,887, filed Sep. 22, 2011, of PCT International Application PCT/US2010/000527, filed Feb. 23, 2010, which claims the benefit of U.S. Provisional Application No. 61/154,737, filed Feb. 23, 2009, and is a continuation-in-part application of U.S. National Phase application Ser. No. 11/884,366, filed May 27, 2008, of PCT International Application PCT/US2006/005248, filed Feb. 15, 2006, which claims the benefit of U.S. Provisional Application No. 60/758,196, filed Jan. 12, 2006, and U.S. Provisional Application No. 60/652,743, filed Feb. 15, 2005, the contents of each of which are incorporated herein in their entireties for all purposes.

GOVERNMENT SUPPORT

This work was supported in part by contracts W911 SR-05-C-0029 and W911 SR-04-C-0036 from the U.S. Department of Defense. The U.S. government may have certain rights in the invention.

BACKGROUND

Technical Field

The present disclosure relates to methods for the detection of specific nucleotide sequences and reagents and kits for use in practicing the methods.

Related Art

Nicking endonuclease enzymes have been previously described. For example, U.S. Pat. No. 6,191,267 discloses recombinant DNA encoding a nicking endonuclease, N.BstNBI, and the production of N.BstNBI restriction endonuclease from the recombinant DNA utilizing PleI modification methylase. U.S. Pat. No. 6,395,523 discloses two methods to engineer nicking endonucleases from existing Type Ms restriction endonucleases, and the production of engineered nicking endonucleases. One approach involves inactivating the dimerization function of a Type Ms restriction enzyme using site-directed mutagenesis approach. Another approach involves replacing the cleavage domain of a Type IIs restriction enzyme with the cleavage domain from the naturally occurring nicking endonuclease, N.BstNBI.

SUMMARY

A method for detecting the presence of a target nucleotide sequence in a sample of DNA can comprise exposing a test sample comprising single stranded DNA to a DNA probe and a nicking endonuclease under conditions that would permit sequence-specific hybridization of the probe to a complementary target sequence, wherein the probe comprises a sequence complementary to the target sequence that also includes a recognition sequence for the nicking endonuclease; and, observing whether the probe is cleaved by the nicking endonuclease, wherein the presence of probe cleaved by the nicking endonuclease indicates the presence of the target nucleotide sequence in the sample DNA.

In various embodiments, the method can be multiplexed to detect the presence of a plurality of target nucleotide sequences in a sample of DNA. In alternative embodiments, the method can further comprise producing amplified DNA from a biological sample. Probes can comprise both fluorescent moieties and fluorescence quencher moieties in proximity such that while the probe remains whole, no fluorescence is observed. When such the probes are cleaved, increased fluorescence can be detected, permitting real-time observation of probe cleavage. In alternatives, probes can be attached to a solid surface, for example in a micro array or on the surface of microbeads.

The technology can be applied to the detection of bacterial pathogens in environmental samples, for example a method of detecting *Bacillus anthracis* is described. Alternatively, the technology can be applied to the detection of viral RNA in crude samples having significant background RNA.

These and other variations are set forth in greater detail below.

BRIEF DESCRIPTION OF THE DRAWINGS

FIG. 1. Overview of the streaming probe technique 1.

FIG. 6. Schematic of the effect of single point mismatches between probe and target on the streaming reaction.

FIG. 14A shows NE site located in the hairpin, FIG. 14C shows the NE site located in the loop, and FIG. 14B shows a cleavage site located between the NE site and the fluor or quencher.

FIG. 22. Illustrates that a hairpin F/Q Probes can give very high signal to noise ratios at reduced temperatures.

FIG. 35. Illustrates probe activity on *B. anthracis* strains and on related species of *Bacillus.*

FIG. 36. Illustrates performance of a multiplex assay for *B. anthracis* detection and genotyping.

DETAILED DESCRIPTION

Figure 2A:
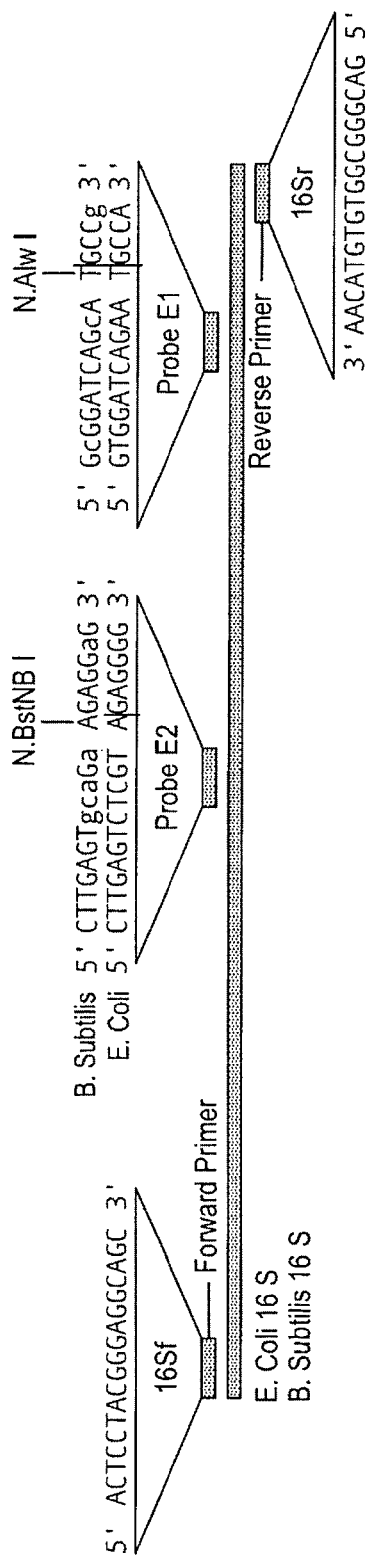
FIG. 2a. Amplification by PCR of 16S rRNA gene DNA from *E. coli* and *B. subtilis* genomic DNA and the design of the *E. coli*-specific probe E1.

We have developed a sensitive method of identifying specific single- or double-stranded DNA sequences and, by extension, other nucleic acids such as RNA that can be converted to DNA. The method involves sequence-specific hybridization of a complementary oligonucleotide probe to a target DNA. When annealed, the oligonucleotide and target create a recognition site for a strand-specific nicking restriction endonuclease. The nicking endonuclease cleaves the oligonucleotide into two pieces, but leaves the target intact. Due to the decreased size of the fragments, their affinity for target DNA is reduced and they dissociate leaving the target free to form a new complex with full-length probe oligonucleotide. The reaction contains excess oligonucleotide (on a mole to mole basis) and so hybridization, cleavage, and dissociation occur many times. The reaction is limited only (at least theoretically) by the availability of oligonucleotide and the stability of the enzyme. Because of the possibility of continuous reaction and turn-over of the probe, the assay can be called a streaming probe assay and the probes referred to as streaming probes.

The reaction can be highly specific since it requires complete complementarity between the oligonucleotide and the target at the restriction site to allow restriction cleavage and can be conducted so as to require complete or nearly complete complementarity outside of the enzyme recognition site to allow hybridization. Hybridization temperatures can be adjusted to allow increased or decreased specificity; sequences containing just one mismatch (e.g., single nucleotide polymorphisms (SNPs)) can be distinguished if desired.

Any technique that can determine the presence of different sized or cleaved DNA can be used to measure either the rate or the end point of the streaming assay reaction. For example, in one embodiment, denaturing polyacrylamide gel electrophoresis (PAGE) is a relatively simple technique that can be used to detect cleavage of the probe oligonucleotide. In another embodiment, the method can be made exceptionally sensitive by using fluorescently labeled DNA together with capillary electrophoresis (CE). In yet another embodiment, a real time method can be performed using an oligonucleotide comprising a fluorescent group attached at one end and a quencher on the other end of the oligonucleotide. In this case, cleavage and dissociation of the probe results in increased fluorescence that can be measured in real-time using a fluorescence reader. As one example, we demonstrate that a streaming assay can be used to specifically detect the presence of plasmids, such as *Bacillus anthracis* pX01 and pX02 plasmids, *E. coli* genomic DNA and *Bacillus subtilis* genomic DNA.

The method can be used whenever there is a desire to detect a specific sequence that includes a recognition sequence of a nicking restriction endonuclease that is known or can be engineered from a type Ms restriction endonuclease. For instance, this method is suitable for detecting the presence of specific DNAs in a mixture (microorganism contamination, infection, etc.); and it can be used for SNP analysis and for genotyping. Statistically, one or more unique target sites containing a suitable nicking endonuclease recognition sequence can be expected to be found in most all DNA sequences of sufficient length.

When combined with whole genome amplification (WGA), for example using isothermal multiple displacement amplification (MDA), it is possible to specifically detect genomic DNA amplified from about ten bacterial cells or less. The streaming probe assay can be multiplexed allowing the detection of multiple sequences (multiple genes in one organism or individual genes in multiple organisms). The multiplexing system can be noncompetitive in nature, unlike multiplexing systems that use polymerase chain reaction (PCR), and allows the generation of high throughput quantitative data.

A method utilizing WGA and a streaming probe can have significant advantages over current methods such as PCR. These can include the following. There is no need to purify DNA before amplification. Amplified DNA is generated that can be used directly with the streaming probe. DNA that can be used for thousands of streaming probe reactions is generated at once. Both DNA amplification and detection methods can be nondestructive, i.e., the same DNA can be used for multiple sequential tests including forensic tests.

The methods described herein exploit the particular properties of nicking restriction endonuclease enzymes. When conventional restriction endonucleases bind to their recognition sequences in DNA, they hydrolyze both strands of the DNA duplex at the same time. Two independent hydrolytic reactions proceed in parallel, driven by the presence of two catalytic sites within each enzyme, one for hydrolyzing each DNA strand. That is, restriction enzymes classically recognize a double-stranded DNA binding site and then cleave each strand of the DNA using two independent catalytic cleavage centers. Nicking endonucleases, on the other hand, cut only one strand. Nt.BstNB I is a naturally occurring nicking endonuclease that only cleaves one strand due to its inability to form dimers (4,5). The nicking endonuclease Nt.Alw I was engineered by creating a fusion protein between the DNA binding domain of Alw I and the cleavage/dimerization domain of Nt.BstNB I (6). Three additional nicking endonucleases Nt.BbvC I, Nb.BbvC I and Nb.Bsm I have been created. The methods described herein exploit the single-strand cleavage activities of nicking endonucleases to provide a sensitive assay for detecting the presence of specific sequences in a DNA sample, or any sample that can be converted to DNA containing a nicking site. In principle, the assay will work with any nicking endonuclease.

Several nicking endonucleases are now available from New England Biolabs. For example, N.BstNB I occurs naturally and nicks by virtue of its inability to form dimers. N.Alw I, a derivative of the restriction enzyme Alw I, has been engineered to behave in the same way. Both nick just outside their recognition sequences. N.BbvC IA and N.BbvC IB are alternative derivatives of the heterodimeric restriction enzyme BbvC I, each engineered to possess only one functioning catalytic site. These two enzymes nick within the recognition sequence but on opposite strands. Nb.Bsm I cleaves only one strand of DNA on a double-stranded DNA substrate. Nicking endonucleases are as simple to use as restriction endonucleases.

As disclosed in U.S. Pat. No. 6,395,523, it is possible to engineer known restriction enzymes to hydrolyze only one strand of the duplex, i.e., to produce DNA molecules that are "nicked," rather than cleaved. Therefore, it is possible to create new specificities as desired from the array of known enzymes and the methods described herein can be generally applied to any sequence for which an appropriate restriction endonuclease exists or can be engineered. The method is not limited to use of Nt.Alw I, Nt.BstNB I, Nb.Bsm I, and Nt.BbvC I, which are exemplified herein.

Thus, a method for detecting the presence of a target nucleotide sequence in a sample of DNA can comprise:
 exposing a test sample comprising single stranded DNA to a DNA probe and a nicking endonuclease under conditions that would permit sequence-specific hybridization of the probe to a complementary target sequence, wherein the probe comprises a sequence complementary to the target sequence that also includes a recognition sequence for the nicking endonuclease; and,
 observing whether the probe is cleaved by the nicking endonuclease, wherein the presence of probe cleaved by the nicking endonuclease indicates the presence of the target nucleotide sequence in the sample of DNA.

The probe need not be perfectly complementary to the target, except in the recognition sequence. Hybridization conditions can be chosen by the skilled practitioner to provide a desired degree of sequence specific hybridization. In various embodiments, one or more base mismatches can be permitted, or perfect complementarity can be required.

FIG. 1 illustrates an exemplary scheme for carrying out the method. Sample DNA comprising a target sequence is first denatured in the presence of a molar excess of an oligonucleotide probe (any method of denaturation should work, heat denaturation was used herein). This probe contains a nicking endonuclease recognition sequence (black bar) and is complementary to one strand of the target DNA. 2. The probe anneals to the target reforming the nicking endonuclease site. 3. On the addition of nicking enzyme, the probe is cleaved and the reduced affinity of the two resulting oligonucleotides allows them to dissociate from the target. Fresh full-length probe hybridizes with the target and is cleaved; the process repeats. In the example shown, the oligonucleotide probe is labeled with a fluorescent tag on the 3' end and a fluorescence quencher on the 5' end (alternate positions are possible as long as the fluor and quencher are separated at the end of the reaction, and the position does not inhibit enzymatic cleavage). Cleavage of the probe results in separation of the fluorescent tag and quencher resulting in increased fluorescence that can be detected in real time. The use of a fluorescence tag—quencher pair is not essential. Any method that can measure the presence of cleaved probe is sufficient. The optimum reaction temperature will vary based on the temperatures at which the oligonucleotide probe and cleavage products dissociate from the target under the enzymatic buffer conditions (i.e., the melting temperature ($T_m$)) and the nicking endonuclease used.

Observing whether or not the probe is cleaved can be accomplished by any technique that can observe the presence of shortened DNA probes or the cleavage of a fluorescently labeled probe, including poly-acrylamide gel electrophoresis (PAGE), capillary electrophoresis (CE), and fluorescence resonance energy transfer (FRET). Of these three techniques, CE is the most sensitive. However, FRET analysis can be performed in a real-time streaming assay. Fluorescent labels and quenchers can be placed anywhere in the probe, the only constraint being that they must not inhibit the nicking endonuclease. For instance, two fluorescent labels can be used to increase the signal strength, or probes with different spectral characteristics can be used in multiplexing.

There are other possible ways of detecting the fragments. Other optical detection methods can be used including bioluminescence and phosphorescence techniques, with or without resonance transfer (e.g., BRET and PRET). In addition, lanthanide-based energy transfer (LRET) can be used to observe the separation between appropriate labels. Another possibility is to use Mass Spectroscopy with or without mass spectroscopy tags. Another possible method is Raman Spectroscopy. Indeed, labeling of the probe with a surface enhanced Raman sphere can increase sensitivity many fold. Another way to detect the fragments produced relates to the fact that each cleavage results in a new 3' hydroxyl and a new 5' phosphate. The increasing presence of either can be measured and enzymatic activity calculated.

Both single and double stranded DNA can be a target for the assay. Indeed, any DNA molecule that can be made single stranded should work in principle. Furthermore, with some nicking endonucleases, direct detection of RNA will be possible (7). An enzyme that recognizes and cuts RNA/DNA hybrids would work as in FIG. 1 with the substitution of DNA target with RNA target (any kind of RNA). An alternative would be to perform an initial reverse transcriptase step to produce cDNA before the streaming reaction. Yet a third way to detect RNA would be to construct a nicking endonuclease that contains a polynucleotide binding site that binds to RNA/DNA hybrids. These kinds of constructs work well with restriction endonucleases (8) so they should also work when fused with the nicking activity of a nicking endonuclease.

Probes can be of any suitable length as can be chosen by a skilled practitioner with consideration of several factors including the following. Probes will be preferably chosen that are of sufficient length to permit sequence specific hybridization and sufficiently short to permit release of the cleaved probe. The skilled practitioner will recognize that the ideal length will be a function of the melting temperature ($T_m$) of the full-length probe and the $T_m$'s of the two products. That is, the $T_m$ differential will preferably be sufficient to allow initial hybridization of the probe followed by subsequent dissociation of both probe fragments. Where convenient, these considerations can be circumvented by cycling temperatures between a reaction/annealing phase and a dissociation phase. In exemplary embodiments employing temperature cycling, the reaction/annealing phase can be conducted at about 40° C. to about 50° C., preferably about 43° C. to about 47° C., most preferably about 45° C., and the dissociation phase can be conducted at about 50° C. to about 60° C. or at most the limit of stability for the nicking endonuclease, for example preferably at about 53° C. to about 58° C., e.g., at about 55° C. However, in general it is to be expected that assays can be designed by choosing a probe/target/enzyme combination that permits use of a single temperature at which the whole reaction proceeds efficiently without having to cycle temperatures. Indeed, in preferred embodiments, using nicking enzymes at or near their maximum temperature limit (e.g., 58° C. for Nt.Alw I) yields very fast and sensitive assays.

Probes can be labeled with any appropriate labels possessing detectable optical, mass, or resonance signatures and the like for use in any of the techniques described herein and similar measurement methods. In positioning the labels, care is preferably taken to avoid labeling a probe in any position that will substantially impair the functioning of the nicking enzyme.

There are currently several nicking enzymes available. For example, New England Biolabs lists Nb.BbvCI, Nb.Bsml, Nb.BsrDI, Nb.Btsl, Nt.Alwl, Nt.BbvCI, Nt.BsmAI, Nt.BspQI, Nt.BstNBI, and Nt.CviPII in their catalog. Methods of engineering additional specificities have been developed and described. Indeed DNA binding domains other than those from restriction enzymes can be used (8). A temperature resistant nicking endonuclease that would be compatible with PCR can be engineered. One can then perform real-time PCR with a streaming probe and the requirement for an exact sequence match when using these enzymes should reduce false positive rates.

The system is very amenable to multiplexing. In one embodiment, a fluorescent group can be positioned relative to the restriction site in different probes so that different sized fluorescent oligonucleotides are formed from different targets. Alternatively, dyes with different spectral characteristics can be used in probes for different targets.

A streaming assay as described herein works well on DNA amplified by multiple displacement amplification. In exemplary embodiments, amplification occurs first and then the streaming reaction is run. However, it should be relatively simple to perform the two assays simultaneously. The probe can be modified so that it can not act as a primer and is resistant to the 3' to 5' exonuclease of the Phi29 polymerase. In preferable embodiments, both reactions run at the same temperature. Conventionally, MDA is performed at 30° C. And, the streaming assay is preferably performed at about 45 to 59° C. However, judicious modification of annealing temperatures and/or buffer conditions and use of alternative polymerase enzymes should permit use of a single temperature.

These methods can be useful in many applications, including: detection and identification of specific organisms in anti-bioterrorism efforts, medical applications for human and animal health, strain/species analysis e.g., ecological studies; molecular biology methods including in situ creation of a signal in a semi-fixed environment such as on a surface or in a gel, creation of a large amount of a specific oligonucleotide from a larger one, sequence-specific activation—e.g., where cleavage product(s) but not the parent (probe) is biologically active, sequence-specific inhibition—where cleavage removes a biological activity of the probe, detection and quantization of levels of DNA or RNA in any system including biological systems or extracts, in vitro assays and the like; and, genomic analyses including SNP/mutation analysis/genotyping. Test samples can include environmental sources such as air (aerosol sampling) water, soil and the like; biological sources can include serum, ascites fluid, cerebrospinal fluid, amniotic fluid, synovial fluid, pleural fluid, saliva, sputum, stool, urine, semen, tissue, biopsies, swabs, and the like from human and non-human sources. The methods can be used to detect sequences in RNA and the samples can comprise RNA, for example including viruses having RNA genomes. In such cases, the methods described herein can comprise preparing DNA from the sample by reverse transcription. The method can be used to detect a wide variety of bacteria, viruses and parasites, such as fungi, protozoa, helminthes, and the like. Exemplary Protocols for Generating Probes to Detect a DNA Sequence.

To generate NESA probes that detect a DNA sequence, a protocol for generating probes can comprise the following steps.
1. Locate all nicking endonuclease (NE) sites in the sequence of interest, which could be a relatively small piece of DNA or a whole genome. Can restrict search to one NE such as Nt.AlwI or search all.
2. Generate oligonucleotide sequences (in silico) that have the following preferred characteristics:
   a. Contains a specific NE site and its surrounding genomic sequence.
   b. NE site positioned within the oligonucleotide so that:
      i. when hybridized to its cognate sequence 2 fragments are generated.
      ii. NE cutting destabilizes the hybridization complex.
   c. Length usually between 16 and 25 bases.
   d. Melting temperature (Tm) is close is close to the optimum for the temperature used for the assay, e.g. for NtAIwI this is approximately 54° C.
   e. For linear probes, a duplex NE site will not be generated from hairpin formation or sequence homodimerization. For stem—loop probes, a duplex will not permit cleavage of stem structure in absence of target sequence.
   f. For linear probes, the sequence lacks stable predicted structure such as hairpins, dimers etc.
3. Design size of cleavage products. The NESA reaction generates oligos of defined size. Where detection of cleavage is by observing size of cleaved probes, any method that can monitor the generation of these different fragments can be used to quantify the reaction. Examples include but are not limited to:
   a. Sizing using gels such as polyacrylamide gels.
   b. Capillary electrophoresis.
   c. Release of part of the oligo from a solid surface.
   d. Separation of two chemical moieties due to cleavage of the oligo as in FRET analysis.
4. Alternatively, design label arrangement. Although the reaction can be followed using unlabeled oligonucleotides, increased sensitivity can be achieved by labeling with:
   a. One or more fluorescent groups (including fluorescent beads) placed so that they do not inhibit the NE.
   b. Radioactivity.
   c. Raman spectroscopy reporters.

Figure 15:
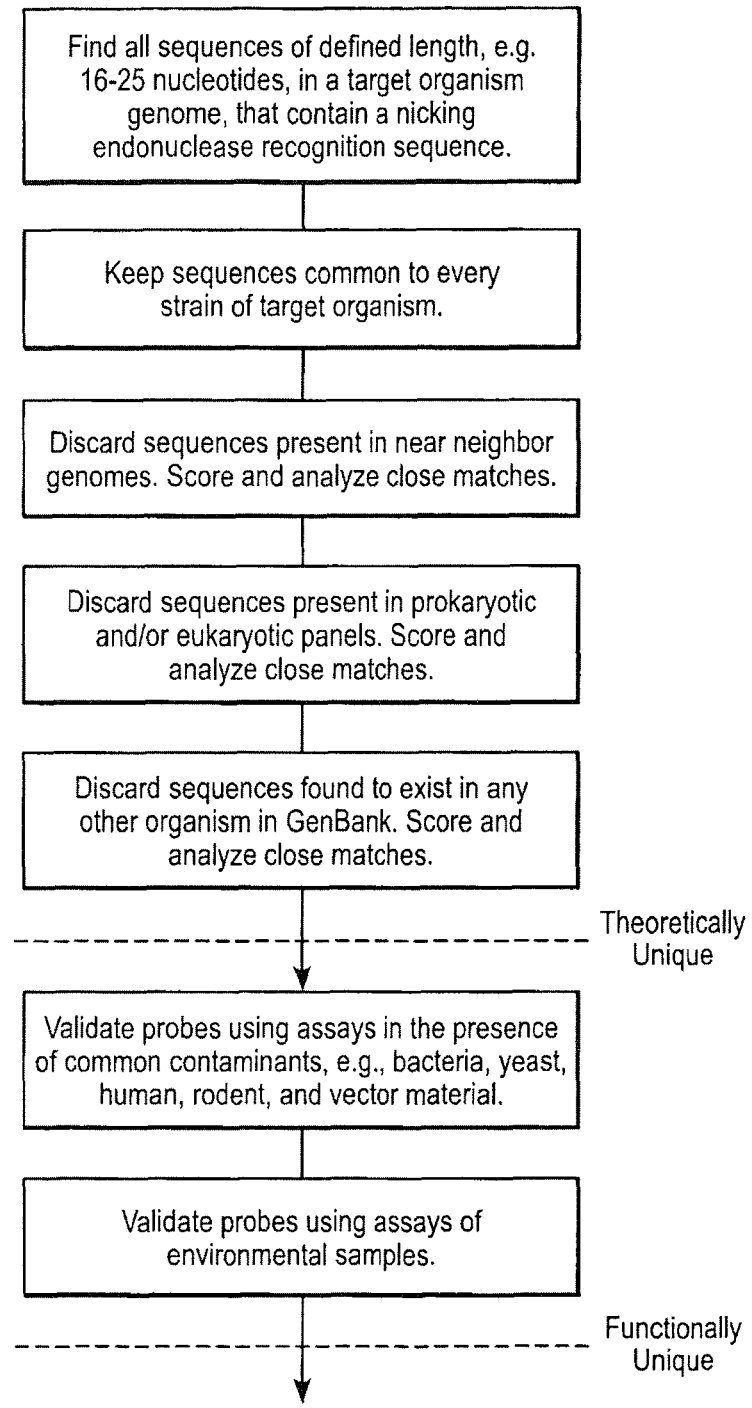
FIG. 15. Illustrates an exemplary procedure for identifying unique probe sequences.

To generate probes that discriminate between two DNA sequences a protocol can comprise the following steps.
1. Locate all nicking endonuclease (NE) sites in the sequences of interest for one or more NE.
2. From each DNA, in silico, generate DNA fragments containing NE sites with enough surrounding sequence to make approximately 16 base sequences. This will generate a group of sequences from each DNA sequence of interest.
3. Perform pattern matching between the fragments using a program such as BLAST.
4. Discard all sequences that are 100% identical and are found in both DNA sequences.
5. The remaining sequences are then designed into probes of length 16 to 25 bases as described above (steps #2 to #5)
6. If desired, multiple computer generated probes from each NE site can be evaluated with respect to length, G:C content, Tm, secondary structure and similarity to DNA from other DNA sequences.
7. Pattern matching on 16 base fragments speed up the analysis. This can be advantageous when designing a probe specific to one genome that does not match any DNA from any other species. The initial matching is not essential. The length of the initial match can be altered depending on the complexity of the two sequences being studied Identifying Unique Probe Sequences. FIG. 15 illustrates a flow diagram of an exemplary protocol for identifying unique sequences. Unique sequences can be theoretically unique by virtue of lack of appearance in any other source in the GenBank database. To identify unique probe sequences a skilled practitioner can use any appropriate bioinformatics search program to find every sequence of defined length, preferably about 16 to 25 nucleotides, that contains a nicking enzyme recognition site. Where a probe is desired to detect multiple strains of an organism, sequences that are common or near matches among target strands can be retained while other sequences are discarded. To identify unique sequences, the potential probe sequences can be screened against a series of increasingly broad panels of known sequence. For example potential probe targets can be screened against near phylogenetic neighbors, then class, and so on until remaining probes are screened against the whole GenBank database. Screening against increasingly larger data sets can save computational time by reducing the set of potential probes at each step before progressing to a screen against the whole database. However, the sequence can be collapsed to a single screen against all of GenBank. At each step, near matches can be scored in terms of mismatch location and Tm to identify potential false positives to be discarded.

After a set of theoretically unique probe sequences comprising a NE recognition site have been identified. Probes having desirable cleavage patterns can be selected for validation. Probes can be validated in assays using samples comprising common contaminants e.g., bacteria, yeast, human, rodent, and vector material. Probes can be further validated in assays utilizing real-world environmental samples. Validation assays can be performed using any NESA assay conditions described herein. Theoretically unique probes which do not produce false positives in validation assays are functionally unique.

Fluor-Quench NESA Probes

Probes comprising a fluorescent moiety and a fluorescence quenching moiety can provide real-time observations of probe cleavage and other advantages. The assay and detection can be performed in a single tube or well of a multi-well plate. Real time assays can be less time consuming than end-point assays and offer the possibility of rate quantification as a function of target concentration. Assays can be performed in parallel. The methods can be less expensive. Methods can be performed in a plate reader or qPCR machine, present in most molecular biology labs.

Linear Fluor-Quench NESA Probes contain at least one fluorescent group and at least one quencher. The fluorescent moiety and quencher can be on either side of the cleavage site. Cleavage separates the fluorescent moiety and quencher increasing overall fluorescence. The fluorescent moiety and quencher can be located on the ends of the probe or can be internally linked.

Hairpin Fluor-Quench NESA Probes contain one or more stem loops to bring the fluorescent moiety and quencher close together. Preferably, the probe should have lower background fluorescence relative to a linear probe due to more efficient quenching. Two forms of stem loop are preferred. The nuclease recognition site can be in the stem section but only one strand comprises a complete nicking enzyme recognition sequence so as to avoid background cleavage. The nuclease recognition site can also be positioned in a single stranded loop.

Figure 13:
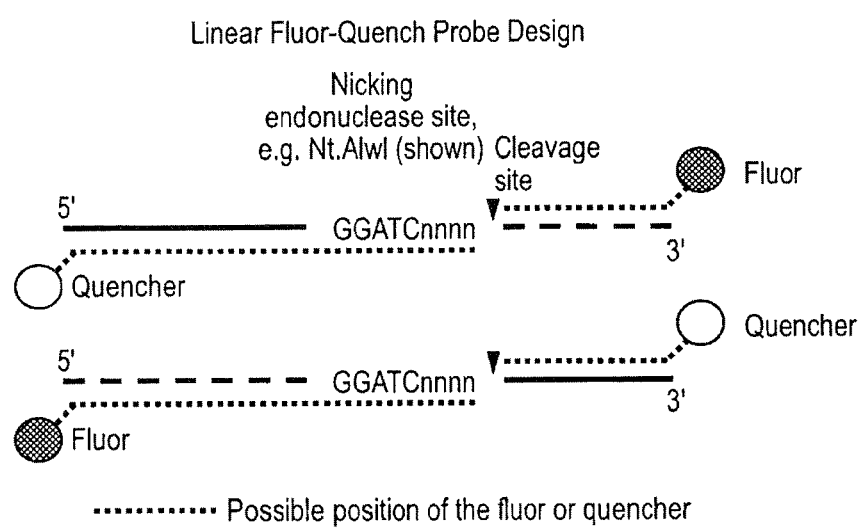
FIG. 13. Exemplary Linear Fluor-Quench Probe Design.

FIG. 13 illustrates an exemplary linear fluor quench probe design. All probes contain a single strand specific nuclease recognition site, a fluorescent residue and a quencher. The quencher reduces the fluorescence of the fluor when the two molecules are in the same oligonucleotide. Cleavage by the endonuclease separates the fluor and quencher by cleaving the oligo between the two groups. These groups can be placed anywhere on the molecule denoted by the dotted blue lines as long as they do not prevent cleavage by the nuclease including between the nuclease recognition and cleavage sites. The most efficient quenching would be expected using a fluor or quencher between the recognition site and the cleavage site and a cognate fluor or quench just the other side of the cleavage site. Any compatible fluor and quencher can be used. In general, most probes that were synthesized used 6-carboxyfluoroscein (FAM) at the ends or dT-fluorescein internally, and either a Black Hole quencher internally or Iowa Black at the ends.

Figure 14A:
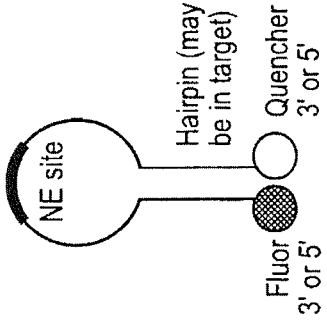
FIGS. 14A-C. A diagrammatic of Stem-Loop Fluor-Quench Probe Design, whereby
Figure 14B:
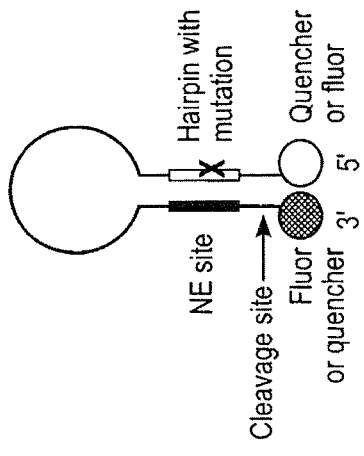
Figure 14C:
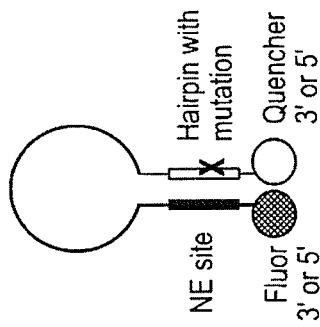

FIG. 14 illustrates exemplary stem-loop fluor-quench probe designs. Illustrated probes contain a single strand specific endonuclease (NE) recognition site, a fluorescent residue and a quencher. The fluor and quencher are held close together by a hairpin. The quencher reduces the fluorescence of the fluor when the two molecules are in the same oligonucleotide. In the presence of target, the hairpin does not form and cleavage by the endonuclease separates the fluor and quencher by cleaving the oligo between the two groups. The NE site can be located in the hairpin (requiring a mutation in the cognate strand) (FIG. 14A) or in the loop (FIG. 14C). The fluor and quencher can be placed on either end of the molecule. The most signal to noise would be expected with a cleavage site that releases the fluor or quencher so that a hairpin fluor-quench pair cannot be reformed (FIG. 14B). In general, most probes that were synthesized used 6-carboxyfluoroscein (FAM) as the fluorescent residue, and Iowa Black as the quencher.

Linear probes can give good signals regardless of the specific arrangement of fluor and quencher. Probes against different targets have can be made to have similar properties. Optimal signal to noise ratio can be obtained when the fluor and quencher were within a few nucleotides of each other. The streaming probe cleavage reaction can occur immediately on addition of enzyme. These probes operate over a wide range of concentrations. Slightly higher sensitivity can be observed with 1 pmol probe compared to 10 pmol.

Hairpin probes can give good signals regardless of the specific arrangement of fluor and quencher. Nicking enzyme recognition sites can be in the stem or loop sections. Endpoint measurement of F/Q probes can increase the signal to noise ratio dramatically.

Surface-Coupled (sc) NESA Probes

Probes coupled to a solid surface can have a number of advantages. If designed so that cleavage removes a fluorescent tag from the surface, just product can be measured by CE, decreasing background. Alternatively, a decrease in bead fluorescence can be monitored. Because the only fluorescence in solution is the product (signal) reactions can be monitored in a fluorometer or qPCR machine.

Many solid surfaces can be used, eg polystyrene beads, surfaces of plastic multi-well dishes, magnetic beads, surface-modified glass slides. Sc-probes containing a fluor and quencher have added advantages (scQ/F probes). The assay and detection can be performed in a single tube or well of a multi-well plate. Real time assays can be performed that are less time consuming than end-point assays and offer the possibility of quantification. Assays can be performed in parallel and are inexpensive. They can be performed in a plate reader or qPCR machine, present in most molecular biology labs. Multiplex is possible. Assays can be set up so that the reaction increases the fluorescence of a solid surface. The use of surface coupled probes allows the production of microarrays.

Standard NESA Probes hybridize specifically to target and contain a nicking endonuclease site such as Nt.Alwl and a fluorescent group attached to the oligonucleotide either at one end or internally. Surface-coupled NESA Probes also have a modification that allows coupling to a solid surface. The sc-probe can be coupled via the 5',3' or an internal residues to a surface as long as the molecule is still cut by a nicking endonuclease. High density coupling can increase the effective concentration of probe. Fluor-Quench sc-NESA Probes, in addition to a fluor and solid surface attachment site, contain one or more quenchers. In some cases the solid surface could act as a quencher e.g. a bead that has inherent quenching activity or a quencher bound to it.

Figure 23:
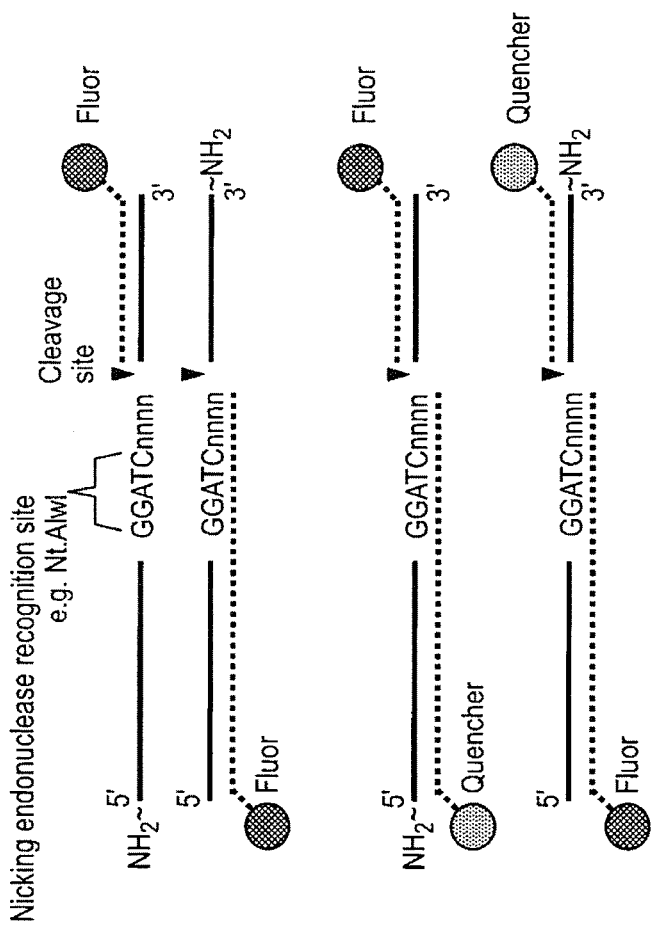
FIG. 23. Illustrates Surface-Coupled Probes (sc-probes) that release a free Fluorescent Oligonucleotide.

FIG. 23 illustrates Surface-Coupled Probes (sc-probes) that release a free fluorescent Oligonucleotide. Exemplary probes contain a nicking endonuclease site (e.g. Nt.ALWI), an $NH_2$ group that that can be attached to a derivatized solid surface, and a fluorescent residue that is released from the solid surface as part of an oligonucleotide on cleavage by the enzyme. Probes C and D contain a fluorescent group and a quencher that straddle the nicking endonuclease site. Cleavage of these probes not only results in release of a fluorescent oligonucleotide fragment into solution, but also results in an overall increase in fluorescence because quenching is relieved. Fragments that are released upon cleavage of a solid-bound probe are indicated in red. The location of the fluor and quencher can be located at the ends of the probe or internally, as indicated by the dotted blue line, as long as the groups do not prevent cleavage by the nicking endonuclease. In general, most probes that were synthesized contained an Nt.Alwl site, used 6-carboxyfluooscein (FAM) as the fluorescent residue, and either a Black Hole quencher internally or Iowa Black at the ends. Probes can be attached either to polystyrene beads or to multi-well plates.

Figure 24:
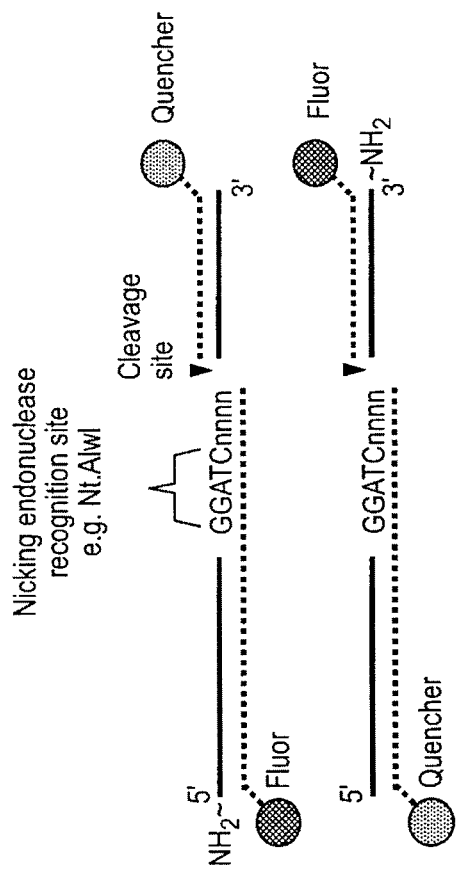
FIG. 24. Illustrates Surface-Coupled Probes (sc-probes) where the solid surface increases in fluorescence upon cleavage by Nt. ALWI.

FIG. 24 illustrates Surface-Coupled Probes (sc-probes) where the solid surface increases in fluorescence upon cleavage by Nt.ALWI. Exemplary probes contain a nicking endonuclease site, an $NH_2$ group that that can be attached to a derivatized solid surface, and a fluorescent group and a quencher that straddle the nicking endonuclease site cleavage site. Cleavage of these probes results in release of a quencher-bound oligonucleotide fragment into solution resulting in increased fluorescence of the solid surface. Fragments that are released upon cleavage of a sc-probe are indicated in red. The location of the fluor and quencher can be at the ends of the probe or internally, as indicated by the dotted blue line, as long as the groups do not prevent cleavage by the nicking endonuclease. In general, most probes that were synthesized used 6-carboxyfluoroscein (FAM) as the fluorescent residue, and either a Black Hole quencher internally or Iowa Black at the ends and contained an Nt.AlwI site.

As described and exemplified herein, a method for detecting the presence of an RNA sequence in a sample of biological material, the method comprising: (a) performing a reverse transcription procedure capable of reverse transcribing RNA into a complementary DNA nucleotide, (b) performing a whole genome amplification technique such as multiple displacement amplification to amplify DNA in the sample of biological material to form an amplified sample product; (c) exposing all or part of the amplified sample product to a DNA probe and a nicking endonuclease under conditions that would permit sequence-specific hybridization of the probe to a complementary target sequence, wherein the probe comprises a sequence complementary to a unique sequence known to be present in the transcript of the RNA sequence that also includes a recognition sequence for the nicking endonuclease; and, (d) observing whether the probe is cleaved by the nicking endonuclease, wherein the presence of probe cleaved by the nicking endonuclease indicates the presence of the RNA sequence in the sample of biological material.

This method can be performed where the RNA sequence is a viral RNA pathogen genome. The method can also be performed in multiplex to permit detection of one or more different RNA and/or DNA genomes by exposing all or part of the amplified sample product to a DNA probe and a nicking endonuclease comprises simultaneously exposing all or part of the amplified sample product to a plurality of DNA probes directed to a plurality of different pathogens and/or pathogen strains, wherein each probe comprises a sequence complementary to a unique sequence known to be present in the transcript of an RNA genome of a pathogen that also includes a recognition sequence for the nicking endonuclease or a unique sequence known to be present in a DNA genome of a pathogen that also includes a recognition sequence for the nicking endonuclease.

As noted above, the sample of biological material can comprise a plurality of unpurified biological contaminants. For example, the sample can be an unpurified environmental air sample washed from a collection device such as an air filter or a liquid sample. The sample can be concentrated and/or buffered, but need not be purified or filtered.

A method for detecting the presence of a target nucleotide sequence in a sample of DNA can alternatively comprise (a) exposing a test sample comprising single stranded DNA to a nicking endonuclease and a substrate surface onto which a DNA probe is affixed under conditions that would permit sequence-specific hybridization of the probe to a complementary target sequence, wherein the probe comprises a sequence complementary to the target sequence that also includes a recognition sequence for the nicking endonuclease; and, (b) observing whether the probe is cleaved by the nicking endonuclease, wherein the presence of probe cleaved by the nicking endonuclease indicates the presence of the target nucleotide sequence in the sample DNA.

Such surface coupled probes provide convenient packaging, storage, and detection. The substrate surface onto which a DNA probe can comprise the surface of a plastic or glass bead. The substrate surface onto which a DNA probe is affixed can also comprise a surface of a well, for example in a multiple well plate. Detection can be by observing the release of a fragment of cleaved probe from the surface. In such a method, the probe can comprise a fluorescent tag that is released from the substrate surface if the probe is cleaved by the nicking endonuclease and observing whether the probe is cleaved by the nicking endonuclease comprises detecting the presence of fluorescent tag released from the surface.

Prior to the assay, the substrate surface onto which the DNA probe is affixed can be kept desiccated. Assays using surface coupled probes can be multiplexed using a plurality of substrate surfaces, each substrate surface comprising a different DNA probe. For example a bead can contain one or more probes, and one or more beads can be used in one NESA reaction. Alternatively, a multiwell plate can be constructed with one or more probes in one or more wells. For example, sixteen wells containing three probes each permit simultaneous screening of 48 samples.

In another aspect, a method for detecting the presence of a target nucleotide sequence in a sample of DNA can comprise: (a) exposing a test sample comprising single stranded DNA to a DNA probe and a nicking endonuclease under conditions that would permit sequence-specific hybridization of the probe to a complementary target sequence, wherein the probe comprises a sequence complementary to the target sequence that also includes a recognition sequence for the nicking endonuclease, a fluorescent tag, and a fluorescence quencher, the tag and quencher being situated on different sides of the recognition sequence for the nicking endonuclease, a first stem portion of the probe being capable of hybridizing to a second stem portion of the probe, the first and second stem portions being separated by a loop portion, the tag and quencher being located in the probe such that the quencher is effective to quench fluorescent emissions of the tag when the stem portions are hybridized to each other; and, (b) observing whether the probe is cleaved by the nicking endonuclease, wherein the presence of fluorescent emissions of the fluorescent tag indicates the presence of the target nucleotide sequence in the sample DNA.

The probe can be designed such that the recognition sequence for the nicking endonuclease is located in the loop portion, or the recognition sequence for the nicking endonuclease can be located in one stem portion where the other stem portion includes a mismatch so that the probe does not comprise a duplex recognition sequence for the nicking endonuclease.

A DNA probe can include a sequence complementary to a unique sequence of a target DNA molecule that also includes a recognition sequence for a nicking endonuclease, a fluorescent tag, and a fluorescence quencher, the tag and quencher being located on different sides of the recognition sequence for the nicking endonuclease, a first stem portion of the probe being capable of hybridizing to a second stem portion of the probe unless the probe is cleaved at a cut site of the nicking endonuclease, the first and second stem portions being separated by a loop portion, the tag and quencher being located in the probe such that the quencher is effective to quench fluorescent emissions of the tag when the stem portions are hybridized to each other. Again, the recognition sequence for the nicking endonuclease can be located in the loop portion or the recognition sequence for the nicking endonuclease can be located in one stem portion and the other stem portion includes a mismatch so that the probe does not comprise a duplex recognition sequence for the nicking endonuclease.

A substrate for surface coupled probes can comprise a surface onto which a DNA probe is affixed where the probe comprises a sequence complementary to a unique sequence of a target molecule sequence that includes a recognition sequence for a nicking endonuclease. The substrate can be a plastic or glass bead, or a multiwell plate where one or more of the wells comprising one or more different DNA probes, each different probe comprising a sequence complementary to a unique sequence of a target molecule sequence that includes a recognition sequence for a nicking endonuclease. The probe can comprise a fluorescent tag that is released from the substrate surface if the probe is cleaved by a nicking endonuclease. The substrate surface onto which the DNA probe is affixed can be stored desiccated, for example when beads or a mutiwell plate is a part of a kit for performing a NESA assay. A kit can comprise a plurality of substrates, e.g. plates, beads, and the like, different substrates comprising one or more different probes.

The following examples serve to further illustrate various aspects and embodiments of the methods described herein. These examples should not be considered limiting in any way.

EXAMPLES

Materials and Methods:

The following materials and methods are used in the examples below unless otherwise indicated.

Genomic DNA. Genomic *E. coli* and *B. subtilis* genomic DNAs were supplied by Molecular Staging Incorporated and were generated using MDA (9) from 100 *E. coli* cells using their REPLI-g® kit. Real-time polymerase chain reaction (PCR) was used to assess the purity of the genomic DNAs (not shown). *B. subtilis* DNA was also generated in house using Qiagen's REPLI-g® kit. Genomic DNA from all other organisms was generated using Qiagen's REPLI -g® kit. The identity of the genomic DNA was confirmed by PCR-sequencing.

PCR Amplified DNA for Use in Streaming Assay Reactions. The 16 S genes from *E. coli* and *S. subtilis* were amplified by PCR using the primers 16Sf (1) and 16Sr (2). Single stranded 16S DNA was prepared using single primer (16Sr) PCR and the amplicon. PCR primers were designed on sequences within the *E coli* (E-oligonucleotides) or *B subtilis* (B -oligonucleotides) 16S RNA genes. PCR reactions were set up using the DyNAzyme PCR reaction kit (MJ Research) with 25 pmoles primers and with 30 cycles (1 min @ 94° C., 1 min @ 55° C., 1 min @ 72° C.) proceeded by a 10 min @ 95° C. denaturation step and followed by a 8 min @ 72° C. extension step.

Oligonucleotides. Oligonucleotides used in these examples are shown in Table 1. Nicking endonuclease sites are in bold, mutations from the wild-type sequence are in lower case. E probes; *E. coli* based; B probes, *Bacillus subtilis* based; c probes, complement of a probe sequence.

TABLE 1

| Oligonucleotide Probes | |
|---|---|
| N .AIw I Probes and Complements (c) | |
| E1 | GT GGATC AGAATGCCA |
| E1c | TGGCATTCT GATCC AC |
| B1 | GC GGATC AGCATGCCG |

TABLE 1-continued

| Oligonucleotide Probes | |
|---|---|
| B1c | CGGCATGCT GATCC GC |
| B2 | CC GGATC TGAGGTAACGATGT |
| E1c m1 | aGGCATTCT GATCC AC |
| E1c m2 | TcGCATTCT GATCC AC |
| E1c m3 | TGcCATTCT GATCC AC |
| E1c m4 | TGGgATTCT GATCC AC |
| E1c m5 | TGGCtTTCT GATCC AC |
| E1c m6 | TGGCAaTCT GATCC AC |
| E1c m7 | TGGCATaCT GATCC AC |
| E1c m8 | TGGCATTgT GATCC AC |
| E1c m9 | TGGCATTCa GATCC AC |
| E1c m10 | TGGCATTCT cATCC AC |
| E1c m11 | TGGCATTCT GtTCC AC |
| E1c m12 | TGGCATTCT GAaCC AC |
| E1c m13 | TGGCATTCT GATcC AC |
| E1c m14 | TGGCATTCT GATCg AC |
| E1c m15 | TGGCATTCT GATCC tC |
| E1c m16 | TGGCATTCT GATCC Ag |
| N.BstNB I probes and Complements (c) | |
| E2 | CTT GAGTC TCGTAGAGGGG |
| E2c | CCCCTCTACGA GACTC AAG |
| B2c | CTCCTCTTCTG CACTC AAG |
| Nt.BbvC I probe | |
| BB-1 | AATTAT CCTCAGC GCCTTT |
| PCR 16 S amplicon Probes | |
| 16Sf | ACTCCTACGGGAGGCAGC |
| 16Sr | GACGGGCGGTGTGTACAA |

Nicking Endonucleases. Table 2 summarizes the nicking endonucleases used in these examples. All nicking endonucleases were obtained from New England BioLabs. Reaction conditions were as suggested by the manufacturer. The amount of enzyme, target DNA, and oligonucleotide probe used, and the length, temperature and volume of the reaction, varied from experiment to experiment and are given in the text and/or figure legends.

TABLE 2

| | | Streaming Assay | |
|---|---|---|---|
| Nicking Enzyme | Recognition Site | Complement | MDA |
| Nt.ALW I | 5 bp | YES | YES |
| Nb.BSM | 6 bp | YES | YES |
| Nt.BbvC I | 7 bp | YES | YES |

PAGE Samples were separated on a 20% polyacrylamide, 7 M urea gel using a standard procedure (3).

Fluorescence Assays Using a FRET Probe. Oligonucleotides were constructed that had a 5' fluorescence quencher (Iowa black, IDT) and a 3' fluorescent group, Alexa 488. Probe streaming reactions were performed in a multi-well plate and analyzed on a SpectraMax Gemini EM, Molecular Devices' fluorescence plate reader using an excitation wavelength of 484 nm and an emission wavelength of 525 nm. The relative fluorescence units shown represent the actual readings minus background fluorescence.

Fluorescence Assays Using Capillary Gel Electrophoresis. Oligonucleotides were constructed that had either a 5 or a 3' fluorescein group. Two instruments were used for this analysis, either a Beckman P/ACE MDQ LIF or an ABI 3130XL. Electrokinetic loading was used in all cases. For the Beckman P/ACE MDQ LIF instrument, the distance from the loading point to the detector was either 20 cm or 10 cm depending on the experiment and the eCAP ssDNA 100-R kit from Beckman was used with voltages between 9,000 and 30,000 volts and loading times of 2 to 10 seconds. In analyses using the ABI 3130XL, the POP6 polymer was used on a 36 cm capillary using ABI's Fragment Analysis Protocol.

Example 1

FRET-Based Streaming Assay

In the streaming assay, as in the non-streaming assay, the oligonucleotide probe is cleaved into two shorter products. There are a number of ways of measuring this cleavage. One way is to measure the change in fluorescence resonance energy transfer between a donor and an acceptor fluorescent moieties, or a fluorescent moiety and a quencher, arranged on opposite side of the cleavage site on a probe, e.g., a FRET assay.

Usually, when a fluorescent molecule is activated by a certain wavelength of light it emits light (fluoresces) at a longer wavelength and this emitted light can be measured using a fluorometer. In FRET, when an acceptor or quencher is present in close proximity to a fluorescent molecule (i.e., a donor), rather than fluoresce, the energy is absorbed by the acceptor or quencher that can or can not (i.e., a dark quencher) emit light at an even longer wavelength.

By arranging a fluor moiety and a quencher moiety in each of the products of parent probe cleavage, i.e., on opposite sides of the probe cleavage site, the parent probe will be quenched due to the proximity of the fluor and quencher but not quenched in the cleaved probe products. That is, cleavage of the probe by a restriction endonuclease physically separates the quencher from the fluor, thereby reducing quenching and causing a measurable increase in fluorescence. This kind of assay is illustrated in FIG. 1. Because the acceptor or quencher can emit at a longer wavelength than the donor fluor, as alternatives to observing an increase, in the fluorescence of the fluor, it is also possible to observe a decrease in emission from an acceptor, or to observe changes in the relative intensities of emission at donor and acceptor emission wavelengths.

Target DNA is first denatured by heating at 95° C. for 10 min in the presence of a molar excess of an oligonucleotide probe (FIG. 1). The target DNA can be any DNA that is, or can be made, single-stranded. We have used oligonucleotides, PCR-amplified DNA, and genomic DNA (Materials and Methods). The probe is an oligonucleotide that has a quencher on the $5^1$ end and a fluor on the 3' end. Although, in this example quencher and fluor are on opposite ends of the probe, either fluor or quencher can be placed anywhere within each of the fragments as long as they do not inhibit enzymatic cleavage and as long as they end up on different cleaved products (below). The probe also contains a nicking endonuclease recognition sequence (black bar) and is complementary to one strand of the target DNA; the probe anneals to the target reforming the nicking endonuclease site. On the addition of nicking enzyme, and incubation at a suitable temperature (discussed below) the probe is cleaved and the reduced affinity of the two resulting oligonucleotides allows them to dissociate from the target. Fresh, full-length probe hybridizes with the target and is cleaved. Cleavage of the probe results in separation of the fluorescent tag and quencher resulting in increased fluorescence.

Theoretically, in the presence of active enzyme the reaction should repeat continuously until near completion. The overall sensitivity of the assay is therefore largely a factor of how much fluorescent probe is available for cleavage and the background (quenched) level of fluorescence.

Example 1.1

Detection of the *E. Coli* 16S rRNA Gene in Per-Amplified DNA Using the FRET-Based Streaming Assay An oligonucleotide probe was developed that hybridizes to *E. coli* t 16S DNA and is cleaved by Nt.Alw I. This probe has reduced binding affinity for *B. subtilis* 16S DNA due to 3 nucleotide differences between the 16 S DNA of the 2 species (Table 1, FIG. 2a). FIG. 2a shows amplification by PCR of 16S rRNA gene DNA from *E. coli* and *B. subtilis* genomic DNA and the design of the *E. coli*-specific probe E1. The forward and reverse primers are designed to amplify 16 S ribosomal DNA from many bacterial species including *E. coli* and *B. subtilis*. (Materials and Methods). The probe was designed based on the presence of a N.Alw I or N.BstNB I site and a melting temperatures between 48 and 54° C. Red letters represent the N.Alw I and N.BstNB I recognition sites. *B. subtilis* sequence that is not identical to *E. coli* sequence is shown in lower case blue.

The utility of this probe was tested using PCR-amplified 16S DNA from *E. coli* and *B. subtilis*. The amplification was performed using a set of universal primers (FIG. 2a).

Figure 2B:
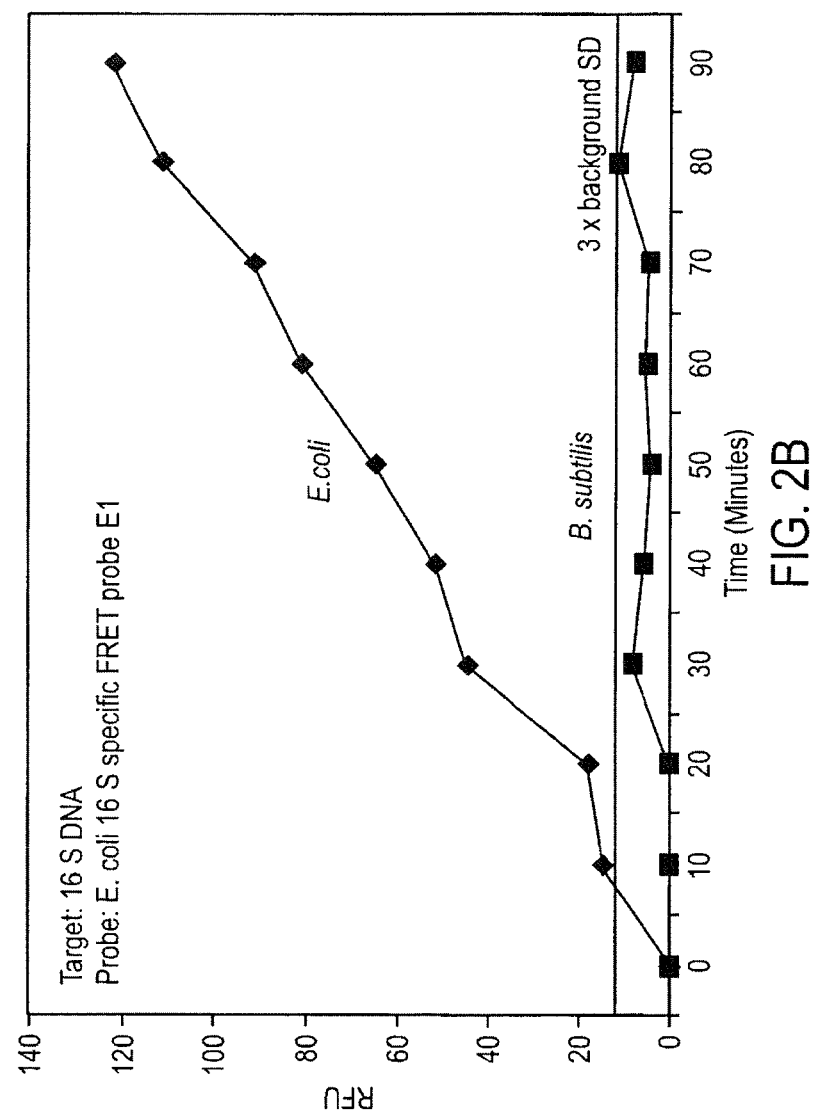
FIG. 2b. Detection of *E. coli* 16S Amplicon using Streaming FRET Probe Strategy.

FIG. 2b shows the detection of *E. coli* 16S Amplicon using a streaming FRET probe strategy. 100 fmole (65 ng) 16 S *E. coli* or *B. subtilis* DNA were incubated with 100 pmole 16S *E. coli* specific FRET probe E1, denatured at 95° C. for 10 minutes and incubated with 50 units N.AIwi at 45° C. in a total volume of 200 μl. Fluorescence was determined at the indicated times.

As can be seen in FIG. 2b, starting with 100 fmoles of *E. coli* 16S amplicon, a signal above background (we used a level of 3-times the standard deviation of the background as our cut off point) can be detected. Whereas with the *B. subtilis* DNA, no signal above the cut off was detected even after 90 min. FIG. 2b also demonstrates that the cleavage reaction and resultant increase in fluorescence can be detected in real-time.

Example 1.2

Detection of *E. Coli* 16S PCR-Amplified DNA in the Presence of Excess Nonspecific DNA Using the FRET-Based Streaming Assay FIG. 3 shows the detection of *E. coli* 16S DNA in the presence of an excess of nonspecific DNA. 100 fmole (65

µg) 16S rRNA *E. coli* amplicon DNA together with the indicated amounts of genomic *B. subtilis* DNA were incubated with 100 pmole 16S *E. coli* specific FRET probe E1, denatured at 95° C. for 10 minutes and incubated with 50 units Nt.Alw I in a total volume of 200 µl at 45° C. Fluorescence was determined at the indicated times.

Figure 3:
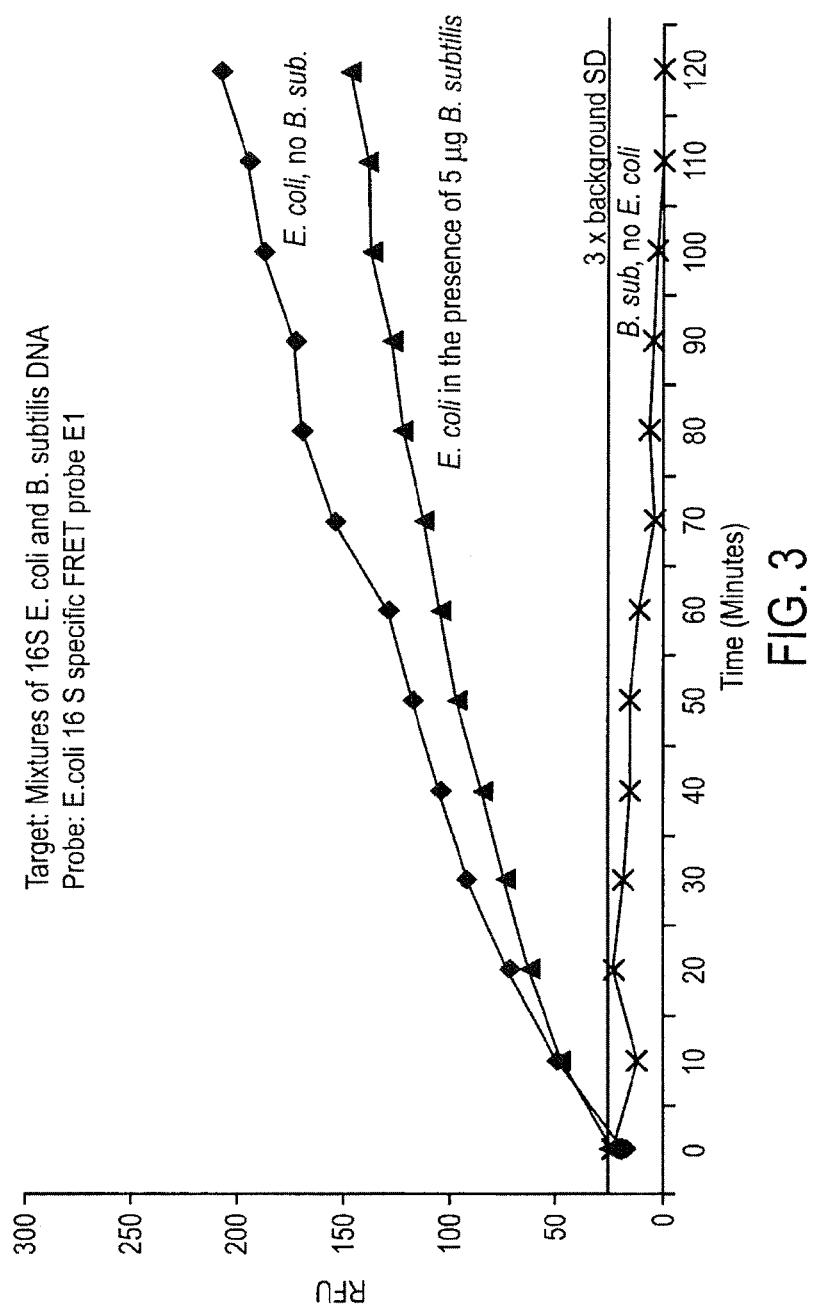
FIG. 3. Detection of *E. coli* 16S DNA in the presence of an excess of nonspecific DNA.

Reactions were set up using the *E. coli* 16S amplicon and increasing amounts of 16S *B. subtilis* genomic (i.e., non-specific) DNA (FIG. 3). We found that the addition of 5 µg of *B. subtilis* DNA to 65 ng of *E. coli* DNA resulted in little inhibition after 10 min but that this inhibition increased to about 25% after two hours. These results demonstrate that specific DNA sequences can be detected in the presence of an excess of nonspecific DNA with only a modest decrease in efficiency. In this demonstration, the excess non-specific DNA is on a weight basis and not a molar ration basis. Due to the difference in target and non-specific DNA molecule sizes the molar ratio of non-specific to target molecules is less than 1, but there is no reason to believe that the same results would not be obtained with a similar molar excess of molecules having similar sizes.

Example 2

A Simple Denaturing-Acrylamide Gel-Based Streaming Assay

For some applications a simple, low cost assay is most appropriate. To demonstrate such an embodiment of the method, a reaction was performed using a probe comprising a fluorescein residue at the 5' end and without a quencher residue (FIG. 4B).

Figure 4A:
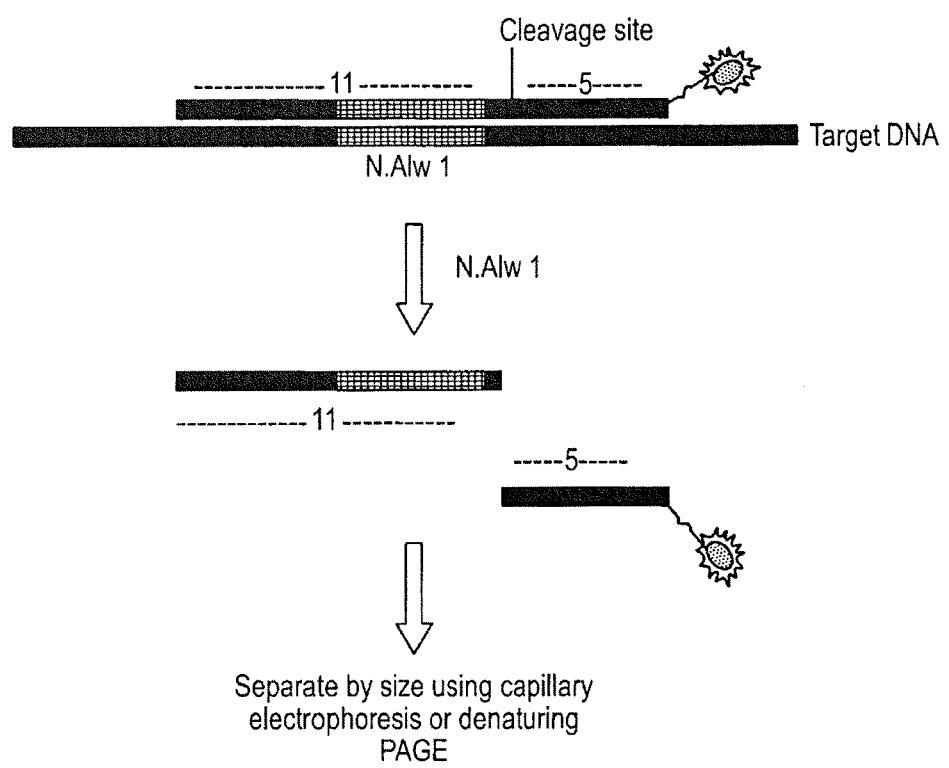
FIG. 4A. Schematic representation of a streaming reaction with Nt.Alw I adapted for CE or gel analysis.
Figure 4B:
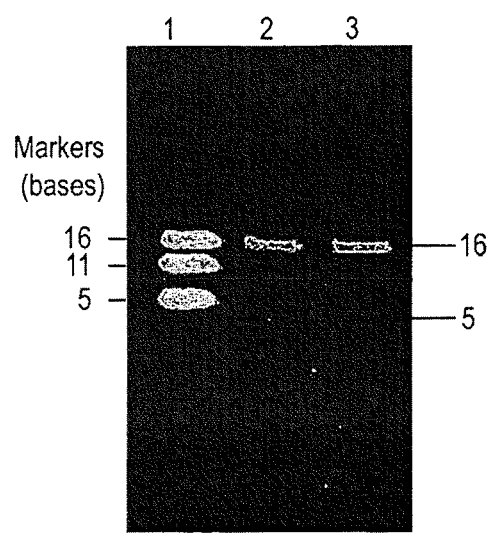
FIG. 4B. PAGE Gel showing the results of mixing 100 pmoles of the E1 probe with 100 fmoles of either *E. coli* (lane 2) or *B. subtilis* (lane 3) oligonucleotides Etc or Blc and 50 units Nt.Alw I in 50 µl buffer.

FIG. 4B shows a schematic representation of a streaming reaction with Nt.Alw I adapted for CE or gel analysis. In this example the probe is 16 nucleotides long with a fluorescein at the 3' end. Nt.Alw 1 cuts 5 residues from the 3' end to give an 11mer and a 5mer. The 5mer retains the fluorescein and can be detected using CE or PAGE (or any other technique that separates according to size).

FIG. 4b shows a PAGE gel showing the results of mixing 100 pmoles of the E1 probe with 100 fmoles of either *E. coli* (lane 2) or *B. subtilis* (lane 3) oligonucleotides E1c or B1c and 50 units Nt.Alw I in 50 µl buffer. After one hour samples were diluted 1:1 with loading buffer and 20 µl was loaded onto a 20% polyacrylamide, 7 M urea gel. Lane 1 contains marker oligonucleotides of 5, 16 and 11 residues. The gel was visualized on a UV light box. The 5mer fragment runs slightly faster than the 5mer standard because it contains a 5' phosphate (the standards do not).

The 5mer probe cleavage product is clearly visible in lane 2 where the sample comprised 100 fmoles *E. coli* complement oligonucleotide (E1c) but not in lane 3 where the sample comprised 100 fmoles *B. subtilis* complement oligonucleotide (B1c). The 11mer cleavage product is not seen because it does not retain the fluorescent label.

Example 3

A Highly Sensitive Capillary Electrophoresis (CE) Assay

Capillary electrophoresis (CE) can be used to detect probe cleavage and can provide a more sensitive alternative to the FRET assays of Example 1. CE separates charged molecules by their size and has long been used to separate DNA fragments. The Beckman P/ACE MDQ LIF system is programmable and has the ability to detect very small oligonucleotides. However, any suitable CE system can be used. The CE assay was set up in the same way as the denaturing acrylamide gel assay shown in FIG. 4B. It differs from the FRET assay in that the probe comprises a single fluorescence molecule at the 3' end of the molecule. That is, a quencher is not required and the position of the single fluorescence residue can be on the 3' or 5' ends, or internal as long as it does not inhibit endonucleolytic cleavage. Cleavage of the 16mer probe results in production of a fluorescently labeled 5mer that can be detected by CE and an unlabelled 11mer that is not observed.

Figure 4C:
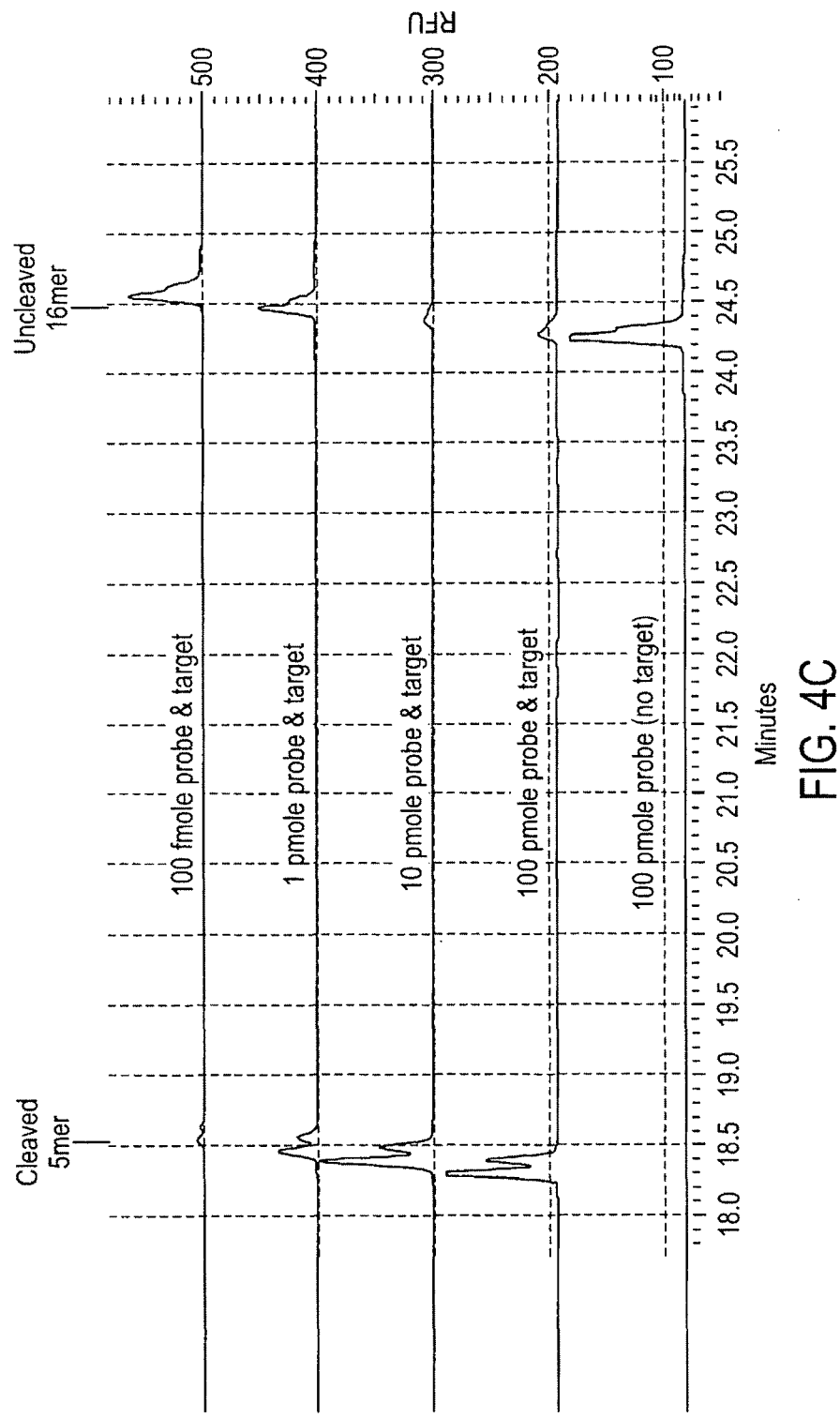
FIG. 4C. Output of a CE instrument in which *E. coli* complement was mixed with fluorescein labeled E1 probe in equimolar concentrations as indicated.

A CE-based assay was also used to examine the effects of varying the levels of target and probe. FIG. 4C shows the output of a CE instrument in which *E. coli* complement was mixed with fluorescein labeled E1 probe in equimolar concentrations as indicated. Samples were denatured for 10 min at 95° C. and cooled to 45° C. 50 units Nt.Alw I were added and the reaction cycled between 45° C. (1 min) and 55° C. (10 sec) for 2 hours. Samples were diluted 1000-fold and electrokinetically (5 s) loaded onto the capillary of a Beckman P/ACE and run at 9,000 volts for the time indicated. The detector was 20 cm from the loading end of the capillary. The doublet seen at the position of the 5mer is most likely a loading artifact.

Figure 4D:
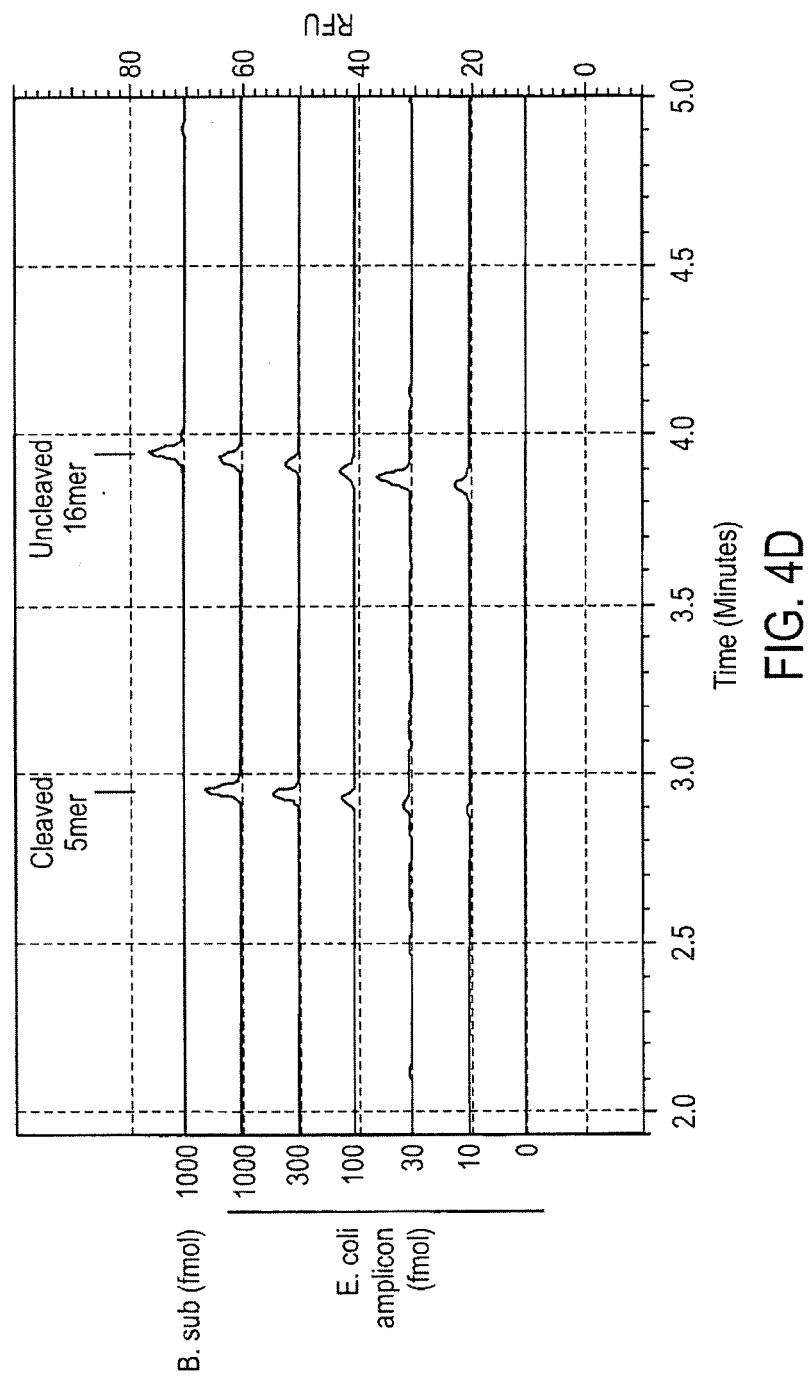
FIG. 4D. Output of a CE instrument in which *E. coli* or *B. subtilis* target 16S rRNA DNA was mixed with 100 pmole fluoroscein-labeled E1 probe as indicated in FIG. 4C.

The 5mer product eluted at about 18.4 minutes and was only seen when *E. coli* 16S amplicon was present. At levels of 100 and 10 pmoles of target and probe, nearly all the E1 probe was cleaved. As levels were reduced further there was a reduced signal but still clearly visible signal with just 100 fmoles of target and probe. The initial reaction was performed in 200 µl, and a 1 µl sample of this reaction was diluted into 100 µl before electrokinetic injection. It is expected that only a fraction of the material present in the sample enters the capillary tube. Thus the 5mer peak seen with the original 100 fmoles probe and target reaction, reflects the signal obtained from far less than 500 attomoles target. This shows a remarkable sensitivity especially given that the probe and target were in equimolar amounts rather than the probe being in excess. We also determined the effects of decreasing the amount of target while retaining a constant level of probe (100 pmoles). As can be seen in FIG. 4D, the reaction is specific. No signal is generated by 1 pmole *B. subtilis* amplicon DNA. However, as little as 10 fmoles of *E. coli* 16 S amplicon gave a positive signal.

In FIG. 4C, the 5mer elutes at approximately 18.3 minutes. To increase the speed of separation we used a 10 cm load to read setting (previously we had used 20 cm) and we increased the voltage to 30,000 from 9,000 volts. Using this set up the 5mer eluted at approximately 2.9 minutes. FIG. 4D shows the output of a CE instrument in which *E. coli* or *B. subtilis* target 16S rRNA DNA was mixed with 100 pmole fluorescein-labeled E1 probe as indicated in FIG. 4C. Samples were denatured for 10 min at 95° C. and cooled to 45° C. Fifty units of Nt.Alw I were added (total volume 200 µl) and the reaction cycled between 45° C. (1 min) and 55° C. (10 S) for 2 hours. Samples were electrokinetically (5 sec) loaded onto the capillary of a Beckman P/ACE and run at 30,000 volts for the time indicated. The detector was 10 cm from the loading end of the capillary.

Example 3.1

Detection of *E. Coli* Genomic DNA (MDA) Using the CE-Based Streaming Assay

The sensitivity of the assay demonstrated in FIG. 4, indicates that the assay can be sensitive enough to detect short specific sequences within genomic DNA. To demonstrate this, we performed the assay using a Nt.Alw I probe on *E. coli* genomic DNA (Materials and Methods).

Figure 5A:
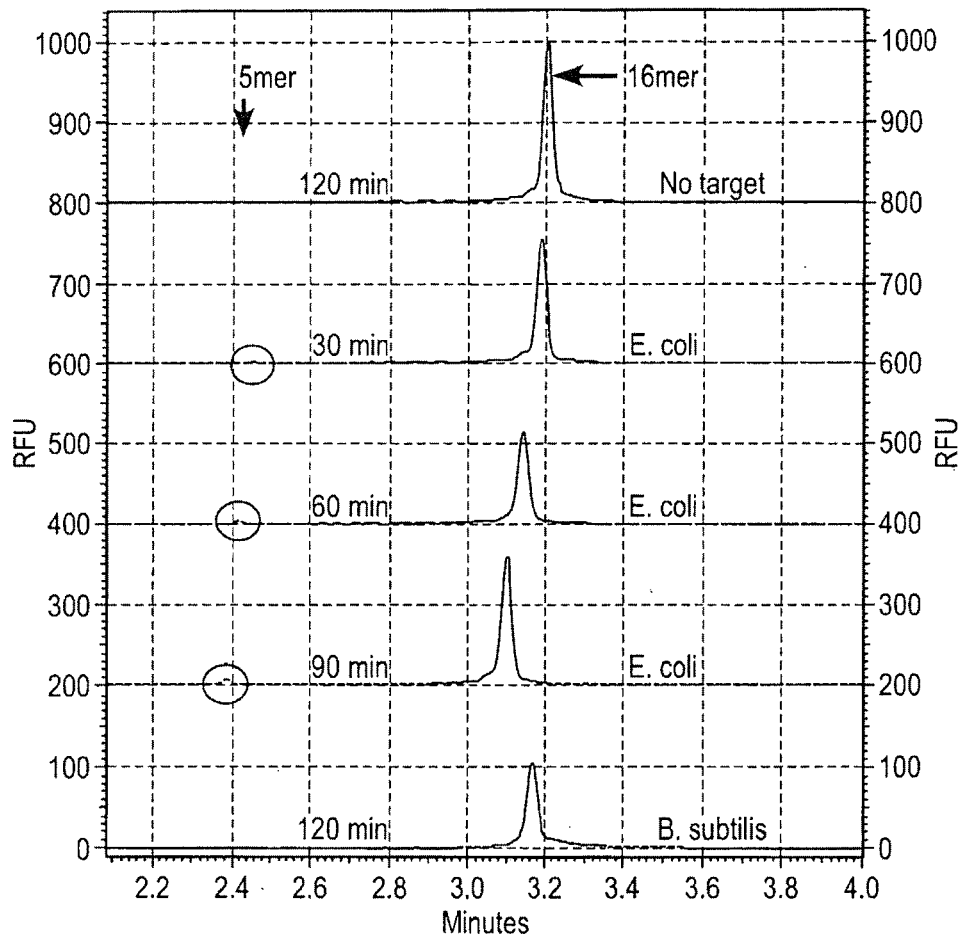
FIGS. 5A and 5B. Detection of specific DNA sequences in *E. coli* genomic DNA. A. Analysis of the reactions using P/ACE MDQ LIF. B. The scale was expanded to more clearly show the peaks corresponding to the 5mers.
Figure 5B:
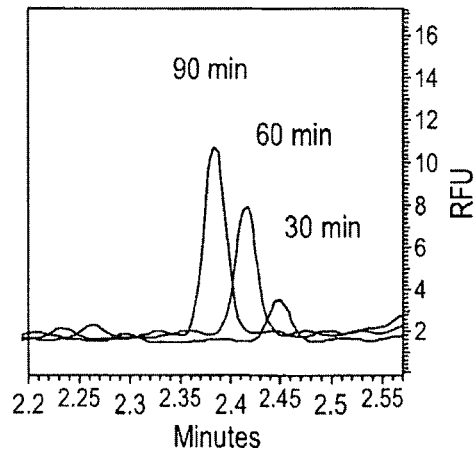

FIG. 5 shows the detection of specific DNA sequences in *E. coli* genomic DNA. Genomic DNA (0.25 µg/µl was denatured at 95° C. for 10 min in the presence of probe E1 (100 pmole). Nt.Alw 1 (50 units) was added (total volume, 200 µl) and the reaction cycled between 45° C. (1 min) and 55° C. (10 sec) for the indicated time. A. Analysis of the reactions using P/ACE MDQ LIF. Samples were diluted 1000-fold and 100 µl (25 ng genomic DNA) were subjected to a 5 sec electrokinetic loading and run at 30,000 volts. B. The scale was expanded to more clearly show the peaks corresponding to the 5mers. The position of 5 mer elution changes somewhat with repetitive CE runs due to the high voltages used. As can be seen in FIG. 5, a positive signal (the 5mer eluting at about 2.4 minutes) can be detected after a 30 min reaction. The probe used gave a positive signal with *E. coli* DNA and did not give a signal with *B. subtilis* DNA even after 120 min. This demonstrates that the streaming assay can be used to determine the presence of DNA from specific organisms.

Example 3.2

Detection of Point Mutations Using a CE-Based Assay

The streaming assay can be used to distinguish between closely related DNA sequences as shown in FIG. 5. To address whether it can also be used to detect single base pair differences, we designed primers identical to the E1 complement used before but introduced a point mutation in individual oligonucleotides at each position. These oligonucleotides were then used in a streaming reaction with the E1 probe and their efficacy determined. FIG. 6 shows the effect of single point mismatches between probe and target on the streaming reaction. Streaming reactions were set up using the *E. coli* E1 probe and targets that consisted of the perfect complement (E1c) oligonucleotide, complementary oligonucleotides each with one mismatch (m1 to m16), and a *B. subtilis* complement that has 3 mismatches (all outside of the N.Alw I binding site). Reactions were performed for 2 h and the products separated by either CE or denaturing PAGE. Black bar, no detectable cutting; vertical hash bar clearly observable product; horizontal hash bar, very low activity (the boundaries were taken as the highest temperature where a reaction was seen to occur); nucleotides in bold, Nt.Alw I site.

As can be seen in FIG. 6, a single missense mutation can be sufficient to substantially decrease the signal. Those oligonucleotides having mutations in the recognition sequence of the enzyme were completely inactive. Thus a streaming probe can be used to measure the presence of single nucleotide mutations/polymorphisms with a properly designed probe.

Example 3.3

Development of a Multiplex Assay Using the ABI 3130XL

CE instruments capable of separating oligonucleotides that differ in size by one nucleotide are available. Such instruments, for example the Beckman P/ACE, can be used to perform a multiplex assay where probes that yield different lengths of cleavage product are used against multiple targets in one reaction. In such a multiplex reaction, each probe can be designed such that the cleavage site for the nicking endonuclease produces a unique sized cleavage product.

The Beckman P/ACE, is a single capillary, one-color machine so its multiplex ability is limited to distinguishing sizes. Another instrument, the ABI 3130XL, has capacity for 16 capillaries and can handle fluors of four different colors. With such a device, multiplexing assays can include probes that are labeled with different colored fluorescent moieties.

Figure 7:
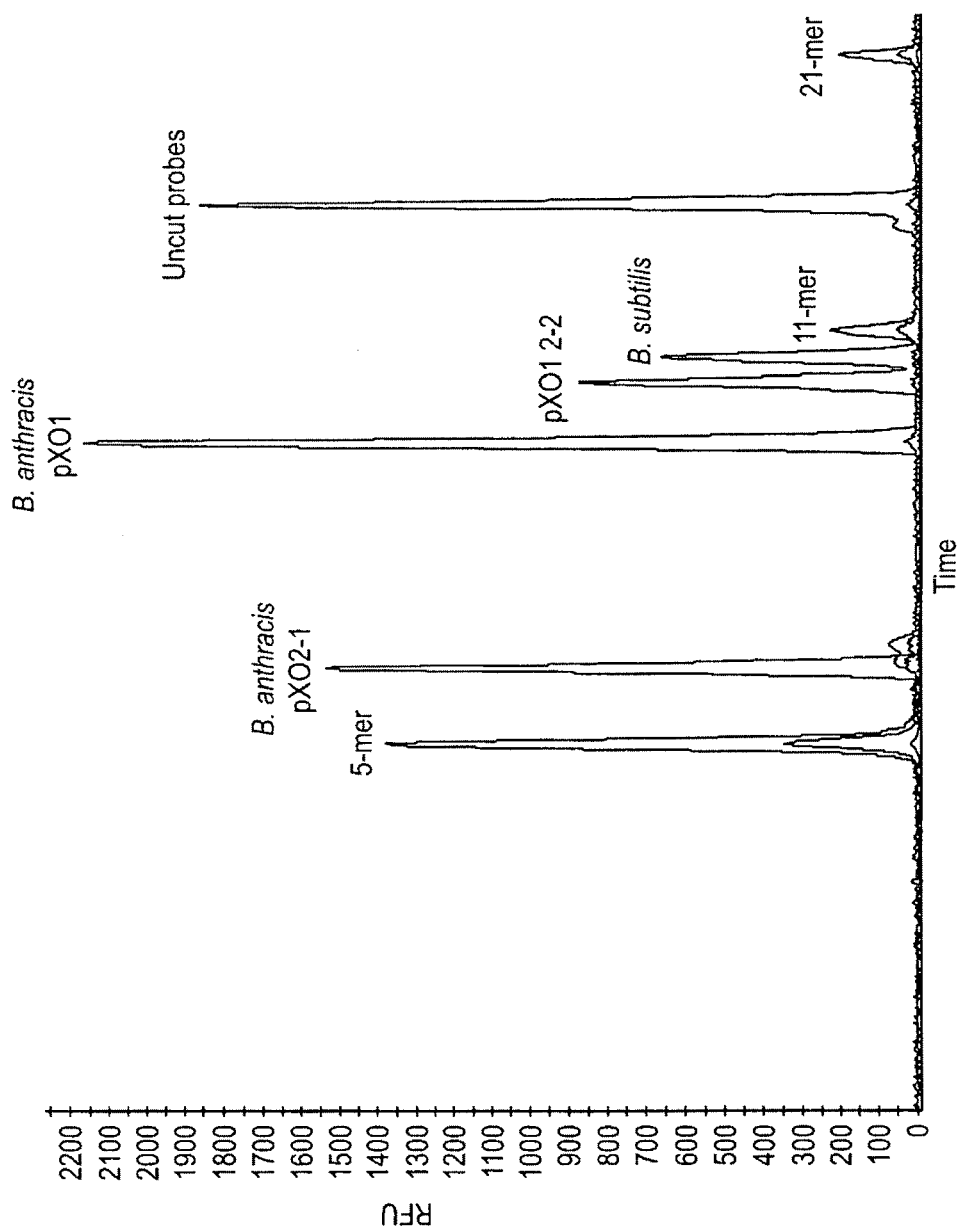
FIG. 7. Results of a four-plex assay. Probes against the four genetic elements shown were designed to give distinguishable fluorescent products using CE on an ABI 3130XL.

The results of a four-plex assay are shown in FIG. 7. In this assay, four different probes were used in one reaction. These probes were specific for the *Bacillus anthracis* plasmids pX01 and pX02 and for *Bacillus subtilis* and were designed to yield different sized cleavage products when cut by a nicking endonuclease upon hybridization. The reaction (10 µl) contained 1 pmole of each probe, 100 fmoles of each complement oligonucleotide, 10 U Nt.Alw I and 1×NEB buffer 2. The reaction was run for 1 hr. at 58° C. before analysis. The green peaks labeled in red are size standards. The *B. subtilis* probe (B2) has a fluorescein at the 5' position and gives an 11-base fragment; pX02-1 (*B. anthracis* pX02 plasmid probe) has a 3' fluorescein and yields an 10-base fragment; pX01 (*B. anthracis* pX01 plasmid probe) has a 5' fluorescein and yields an 10-base fragment; pX01 2-2 (*B. anthracis* pX01 plasmid probe) has a 5' fluorescein and yields a 11-base fragment.

In the presence of the four target DNAs, four distinct signals were generated. These data demonstrate the capability of multiplexing. Since the instrument is capable of using fluors with four different colors, a multiplex assay of 16 probes is an obvious extension. Indeed, the resolving power of the capillaries is such that multiplex assays with more than 16 probes are possible (we estimate, based on the resolving power of the capillaries, that a 40-plex is possible). These data, taken together with the above examples, also show the generality of the streaming probe, because the feasibility of the assay with three different organisms (including *E. coli*) using both chromosomal and plasmid sequences has been demonstrated.

Example 4

Use of a Combination of MDA and Streaming Probe to Detect Approximately 10 Bacteria One of the goals in applications such as detection of bio-warfare agents, is to detect vanishingly small numbers of organisms. To demonstrate that the combination of MDA and streaming probe can be sensitive enough to detect low levels of bacteria, a serial dilution of a culture of *B. subtilis* was performed and the samples split into two. One half was used to quantitate the number of bacteria present; the other half was used to perform MDA.

Figure 8:
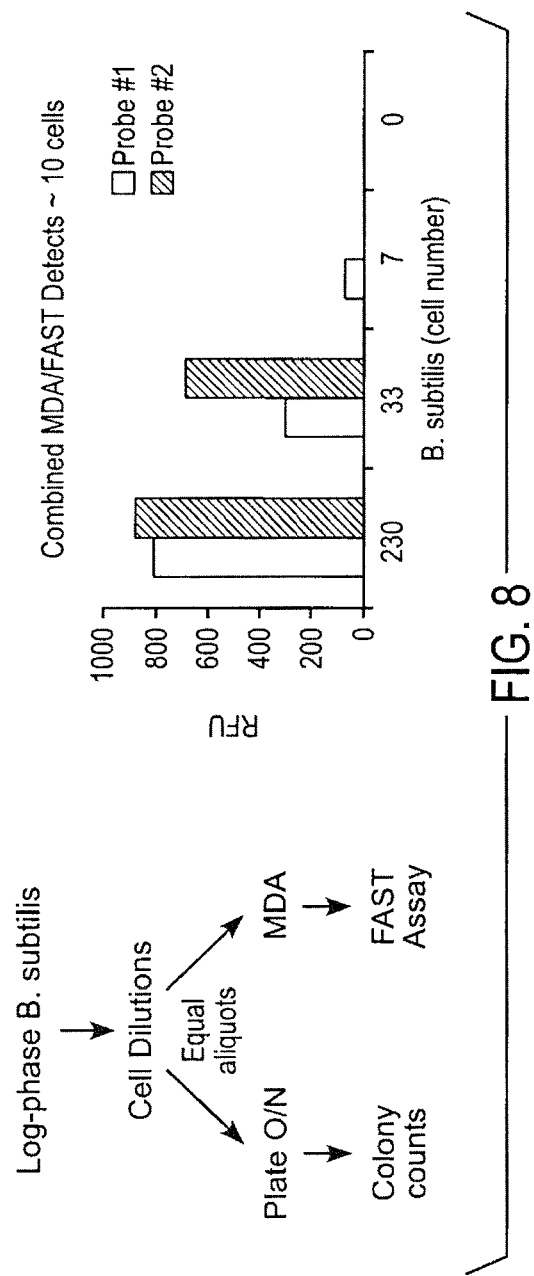
FIG. 8. Results showing the sensitivity of a combined MDA and streaming probe assay.

FIG. 8 shows the sensitivity of the combined MDA and streaming probe assay. Log phase *B. subtilis* were serially diluted and each dilution was split into two. Half the dilution was used for a plating assay, while 1 µl of the other half was used for a MDA reaction (50 µl) using a REPLI-g® kit (Material and Methods). 100 ng of the amplified DNA was then used for each 10 µl streaming reaction (100 ng MDA DNA, 1 pmole probe, 10 U Nt.Alw 158° C.). Probe 1 is B1 and probe 2 is B2 (Table 1).

As can be seen in FIG. 8, approximately 10 *B. subtilis* cells can be detected by this approach. Remarkably, the MDA reaction made enough DNA for at least 500 hundred independent streaming reactions each of which can be multiplexed if desired. These experiments show the feasibility of using this approach to detect low levels of bacteria, they also show that crude DNA produced directly from bacteria can be used for the streaming reaction.

Example 5

Adjustments in the Parameters of the Reaction

Figure 9:
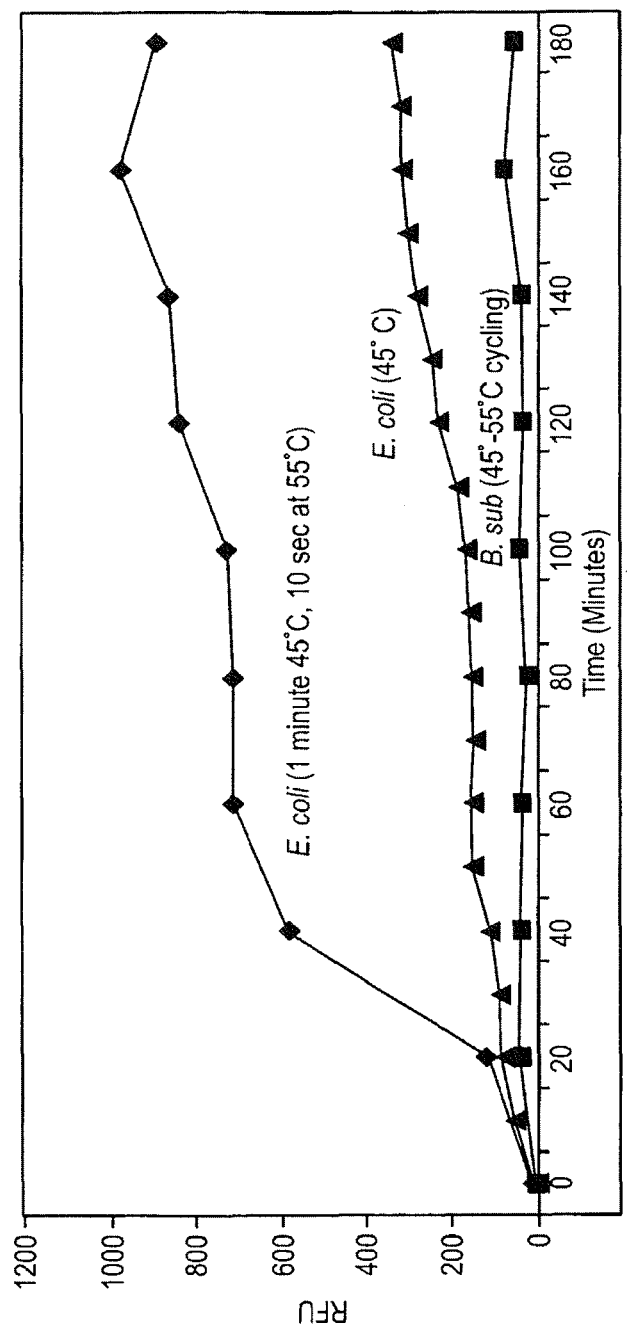
FIG. 9. Results demonstrating that cycling the temperature during annealing, cleavage and dissociation increases the reaction rate.

The Use of Temperature Cycling: One possible rate limiting effect is the dissociation of the probe fragments from the target after the probe has undergone endonucleolytic cleavage. Indeed, as the concentration of cleaved probe increases with time, there could be a significant inhibition of the process. Initially our assays were set up at 45° C. However, cycling between two temperatures, a reaction temperature (45° C.) and a dissociation temperature 55° C. might lead to an increased rate of reaction. The results of this strategy are shown in FIG. 9. 100 fmole (65 µg) 16S *E. coli* or *B. subtilis* amplicon DNA were incubated with 100 pmole 16S *E. coli* specific FRET probe E1, denatured at 95° C. for 10 minutes and incubated with 50 units Nt.Alw 1. At a constant 45° C. or cycled between 45° C. (1 min) and 55° C. for 10 sec. Fluorescence was determined at the indicated times. These values were arrived at empirically. Optimal temperatures can be determined for any probe/target/enzyme combination. The results show that temperature cycling does increase the initial rate of the reaction. Nt.Alw I is stable up to at least 58° C. and at this temperature the reaction is very efficient. Temperature cycling can be of use for enzymes whose denaturation temperature is below the optimum reaction/disassociation temperature.

Use of Excess Probe: Another possible rate-limiting step is the annealing of the probe to the target. This can be mitigated by using high concentrations of probe (pmoles) to drive the reaction forward. Interestingly, as much as practically all of the probe can be seen to be cut in assays containing as little as 1 fmole target, indicating a probe turnover of at least 1000.

Figure 10A:
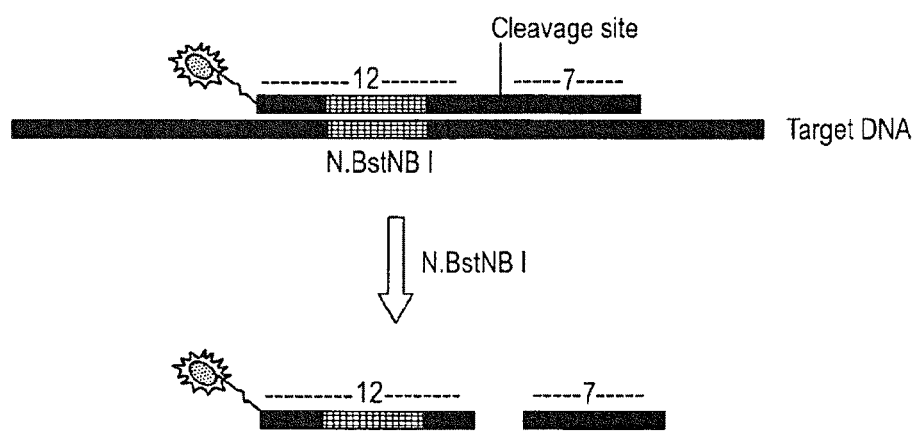
FIG. 10A. Schematic representation of a streaming reaction with N.BstNB I adapted for CE or gel analysis. In this example the probe is 19 nucleotides long with a fluorescein at the 5' end. N.BstNB I cuts 5 residues from the 3' end to give a 12mer and a 7mer.
Figure 10B:
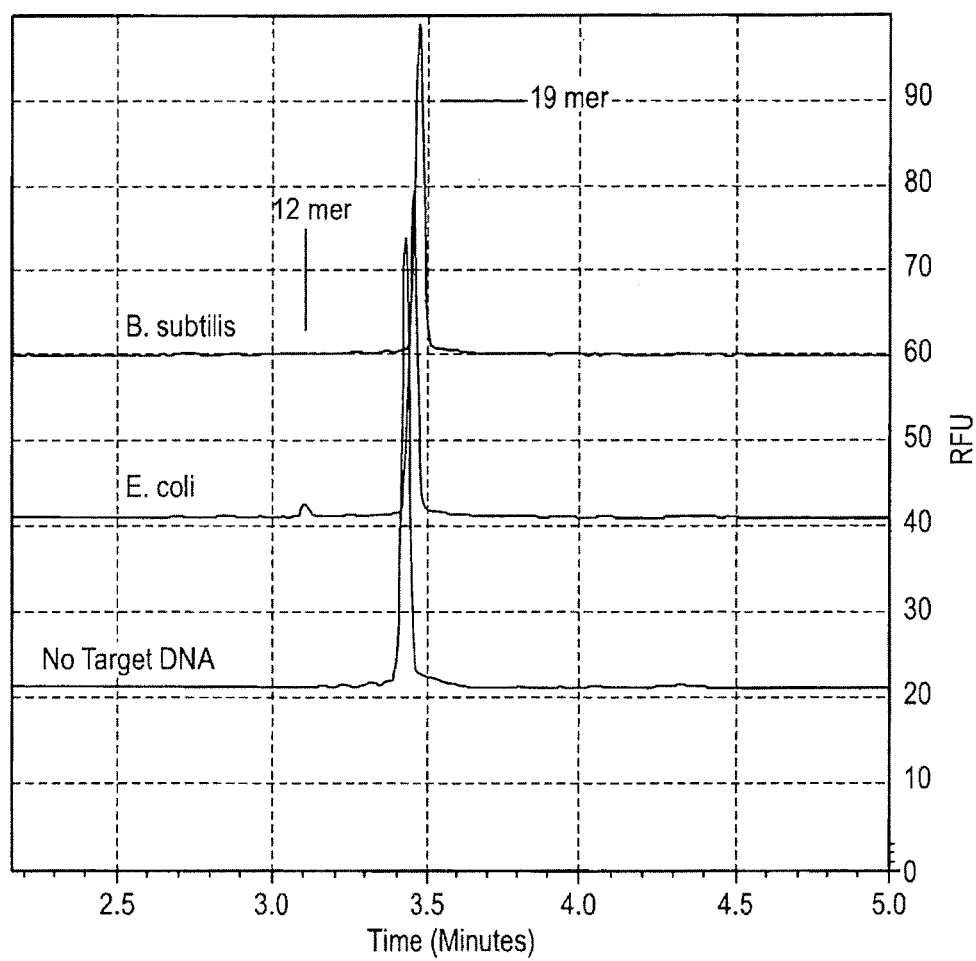
FIG. 10B. Results of a streaming assay using Nt.BstNB I.
Figure 11:
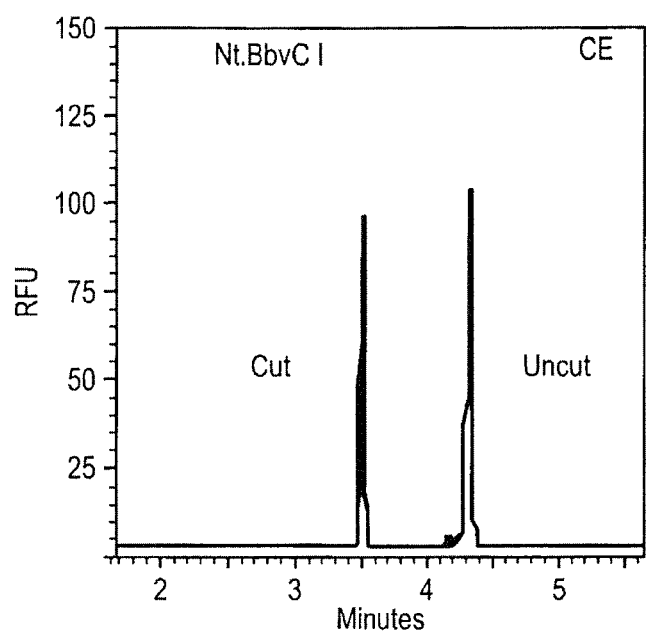
FIG. 11. Results of a Nt. BbvC I streaming assay.

Use of other Nicking Endonucleases: To demonstrate the generality of the method using other nicking endonucleases, a probe, E2 (FIGS. 2a, 10a) was designed to recognize the *E coli* amplicon and to be cleaved by Nt.BstNB I at its recognition site. FIG. 10A shows a schematic representation of the streaming reaction with N.BstNB I adapted for CE or gel analysis. In this example the probe is 19 nucleotides long with a fluorescein at the 5' end. N.BstNB I cuts 5 residues from the 3' end to give a 12mer and a 7mer. A mismatch in the N.BstNB I recognition site between *E. coli* and *B. subtilis* 16 S DNA prevents cleavage of the probe in association with *B. subtilis* DNA. Thus, the probe can be used to identify the *E. coli* target in a *B. subtilis* background. Detection of *E. coli* was tested and the results depicted in FIG. 10B. In a 200 µl reaction, 100 pmoles probe E2 were incubated with the indicated complement B2c or E2c, 100 U Nt.BstNB 1 for 2 h cycling between 45° C. for 1 minute and 55° C. for 10 sec. The sample was separated by CE with a 5 sec electrokinetic injection. The full length probe is 19 nucleotides long and is cleaved into a 12mer and a 7mer. Both the 19mer and the 12mer are seen (the 5mer is not fluorescently labeled) in the reaction containing *E. coli* complement DNA (E2c) but not in control reactions lacking any target or a reaction containing *B. subtilis* complement DNA (B2c). Similar results were obtained with the enzyme Nt.BbvCI (FIG. 11 and Table 2). 1 µg *E. coli* MDA was incubated with 10 pmole Nt.BbvC I probe BB-1 with a fluorescein label on the 5' end (Table 1), 10 U NT.BbvC I, in a final volume of 10 µl for 3 hrs at 54° C. The reaction was analyzed on a Beckman P/ACE.

These data show that the assay is not dependent on one nicking endonuclease but that other nicking endonucleases can be used so long as they cleave just one DNA strand.

Figure 12:
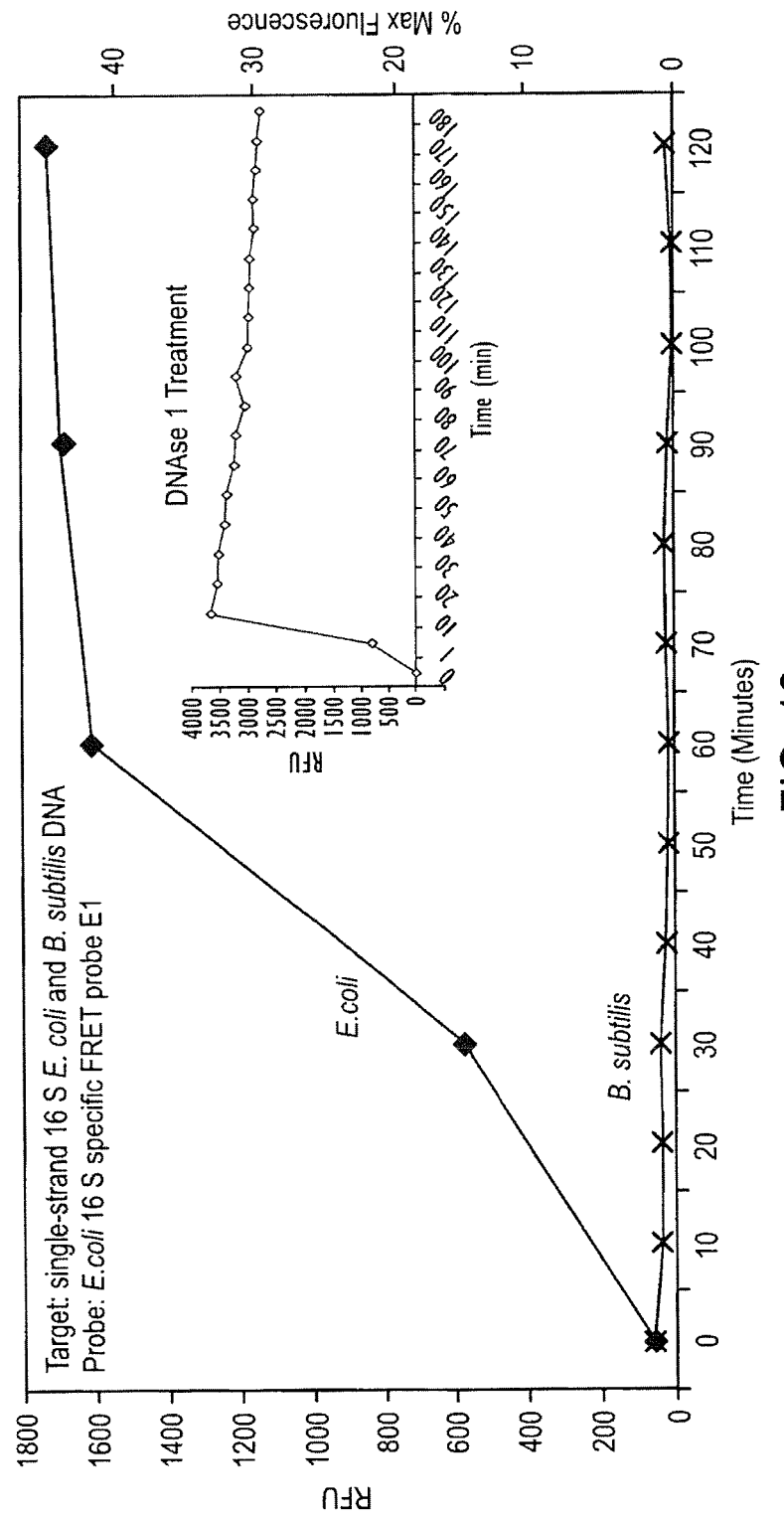
FIG. 12. Results showing that single stranded DNA target can improve sensitivity.

Detection of Single Strand Targets: One-sided PCR was used to create a single-stranded *E. coli* 16 S DNA. 100 fmole (65 ng) 16 S *E. coli* or *B. subtilis* single-stranded DNA was incubated with 100 pmole 16 S *E. coli* specific FRET probe E1, denatured at 95° C. for 10 minutes and incubated with 50 units N.Alw 1 in a total volume of 200 µl. and cycled between 45° C. (1 min) and 55° C. for 10 sec. At the indicated times, fluorescence was determined. Inset: 100 pmole probe was incubated with 50 units of *E. coli* DNAse I at 37° C. Fluorescence was determined at the indicated times. As can be seen in FIG. 12, single-strand DNA works exceptionally well in the assay. To determine the maximum fluorescence possible in the assay, the reaction was treated with DNAse I and fluorescence determined over time. DNAse I cleaves all the DNA and should thus give the maximum signal possible in the reaction. The data shows that in this reaction Nt.Alw I reached a remarkable level of 45% of maximum possible fluorescence.

Example 6

Fluor/Quench Probes

TABLE 2

Exemplary Fluor/Quench Probes

| Name | Sequence (5' to 3') | Type |
|---|---|---|
| Set 1 | | |
| P36.1 | FAM-CG <u>C</u> GGATC <u>TTAA</u>\|<br>GGCTACGTCTT GAACC GCG-IB | Hairpin.<br>Recognition site<br>& point muta-<br>tion on stem,<br>5'F, 3'Q |
| P36.2 | FAM-CGCGTT <u>C</u> GGATC <u>TTAA</u>\|<br>GGCTACTTAAC GCG-IB | Hairpin.<br>Recognition<br>site in loop,<br>5'F, 3'Q |
| P36.7 | FAM-C <u>C</u> GGATC <u>TTAA</u>\|<br>GGCTACGTCTT<br>AAACCTTAATTACCGG-IB | Hairpin<br>Recognition<br>site in stem<br>5'F, 3'Q, tri-<br>ple mutation |
| Set 2 | | |
| P97.3 | GCTAACTTGC GGATC T-F<br>TAA\|GG-IB | Linear, F be-<br>tween recogni-<br>tion & cut<br>site, Q 3' |
| Set 3 | | |
| D2.1 | TT GGATC AT-F AG\|GGTAT<br>TGGATCTA-IB | Linear, F be-<br>tween recogni-<br>tion & cut<br>site, Q 3' |
| D2.2 | IB-TT GGATC AT AG\|GGTA<br>T-F TGGATCTA | Linear, Q 5', F<br>internal |
| D2.3 | FAM-TT GGATC AT AG\|GGTA<br>T TGGATCTA-IB | Linear, F 5',<br>Q, 3' |

TABLE 2-continued

Exemplary Fluor/Quench Probes

| Name | Sequence (5' to 3') | Type |
|---|---|---|
| Set 4 | | |
| D4.1 | AGTGCT-F G GGATC TCAG\| GAAGGA-IB | Linear, internal F, Q 3' |
| D4.2 | FAM-AGTGCT G GGATC TCAG\| GAAGGA-IB | Linear, F 5', Q 3' |

F, FAM; IB, iowa black; |, cut site; blue text, recognition site; red text, fluorescent attachment site; F, fluorescein; FAM, 6-carboxy-fluoroscein. All sequences written 5' to 3'. The targets sequences are underlined in set 1, and are the complement of the probes in sets 2, 3 and 4 with the exception of the T attached to the fluorescein.

Figure 16:
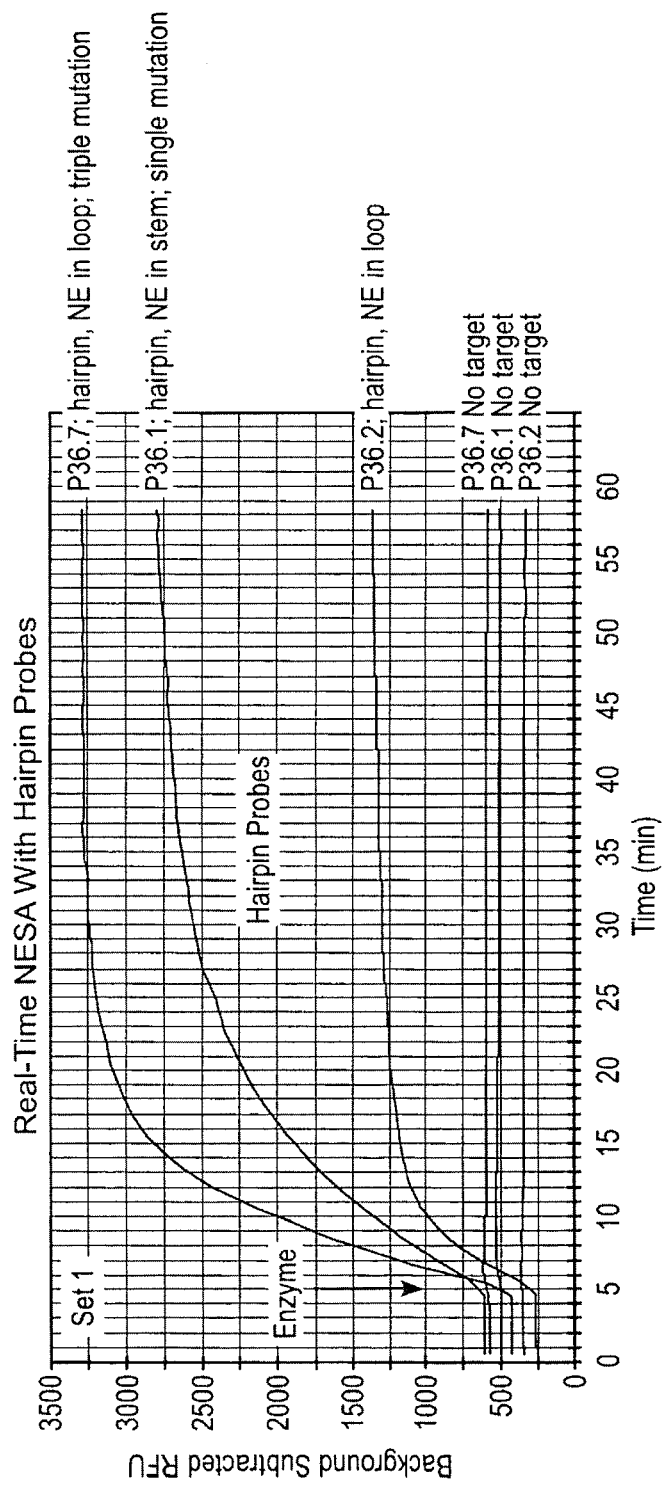
FIG. 16. Exemplary results using stem-loop F/Q probes.

Standard 20 µl NESA reactions were set up in 96-well qPCR plates containing 10 pmol probe, 200 fmol target oligo. Reactions were incubated at 58° C. for 5', 2 µl Nt.Alwl added, and fluorescence measured every minute at 58° C. Results are illustrated in FIG. 16.

Figure 17:
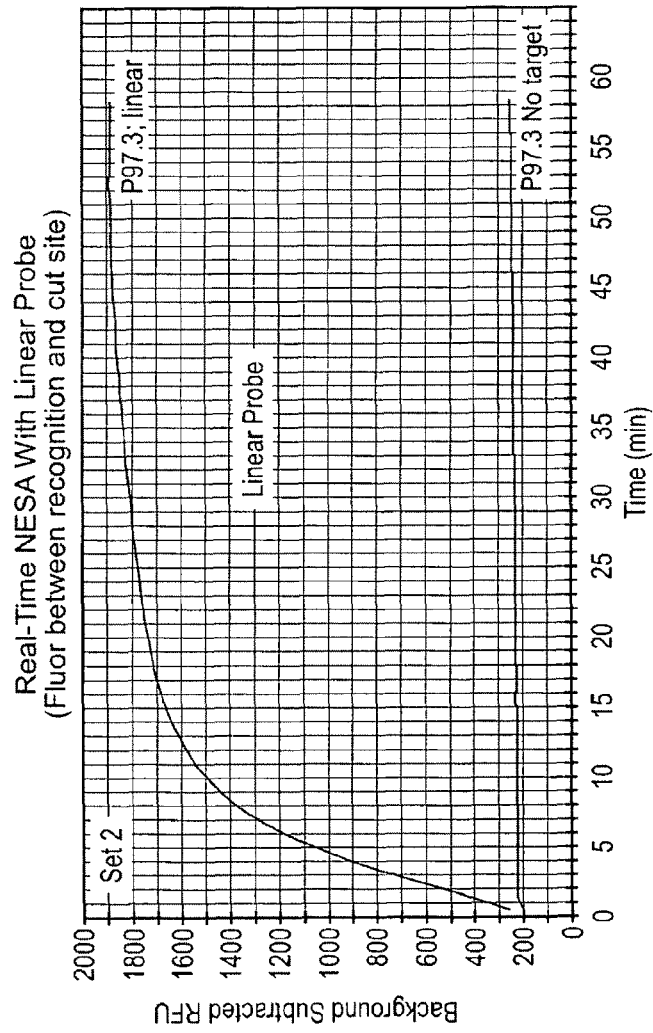
FIG. 17. Illustrates real time results using a stem-loop F/Q probe.

Real time measurements were taken. Standard 20 µl NESA reactions were set up in 96-well to qPCR plates containing 10 pmol probe, 200 fmol target oligo, 2 µl Nt.Alwl. Reactions were incubated at 58° C. and fluorescence measured every minute. Results are illustrated in FIG. 17. Standard 20 µl NESA reactions were set up in 96-well qPCR plates containing 10 pmol probe, 1 pmol target oligo, 2 µl Nt.Alwl. Reactions were incubated at 58° C. and fluorescence measured every minute.

D2.1=Den2-3'BHQ
D2.2=Den2-5EHQ
D2.3=Den2-Opp
D4.1=Den4-3'BHQ
D4.2=Den4-Opp

Figure 18:
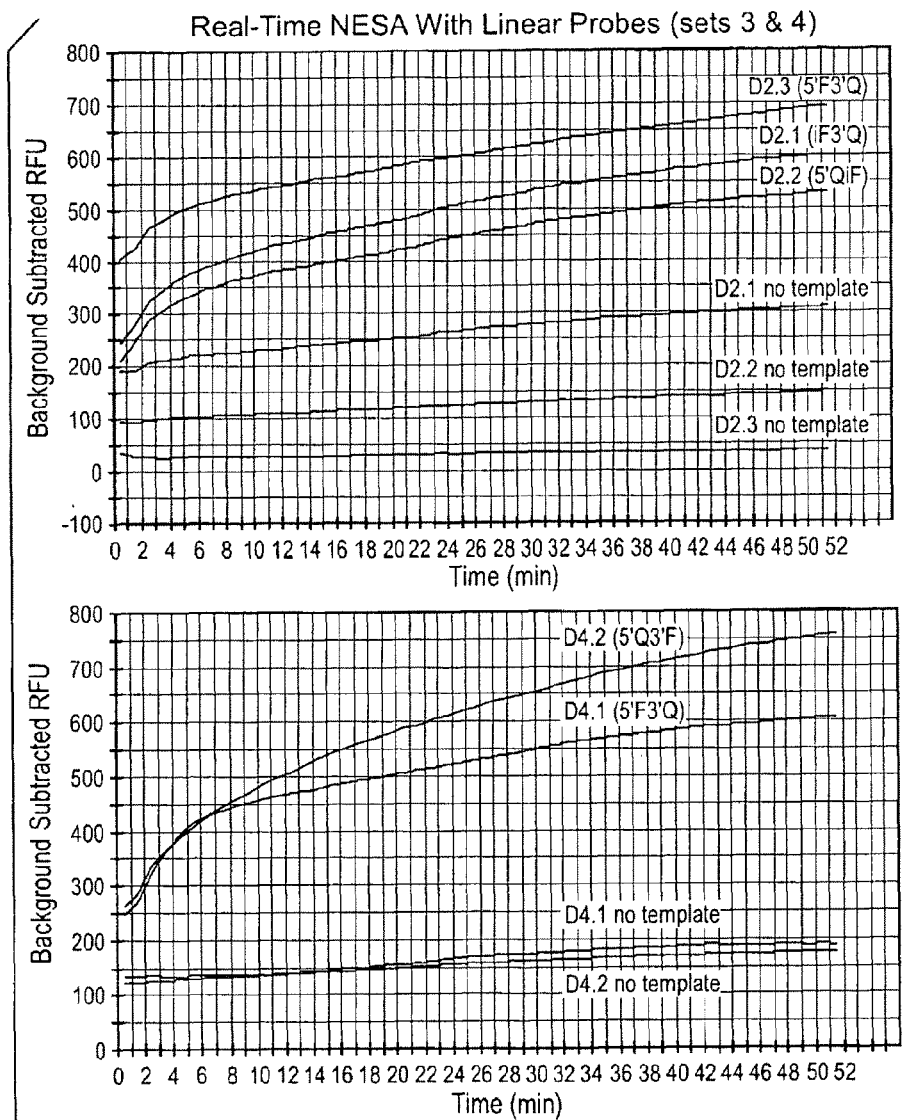
FIG. 18. Illustrates real time results using a linear F/Q probe.

Results are illustrated in FIG. 18.

Figure 19A:
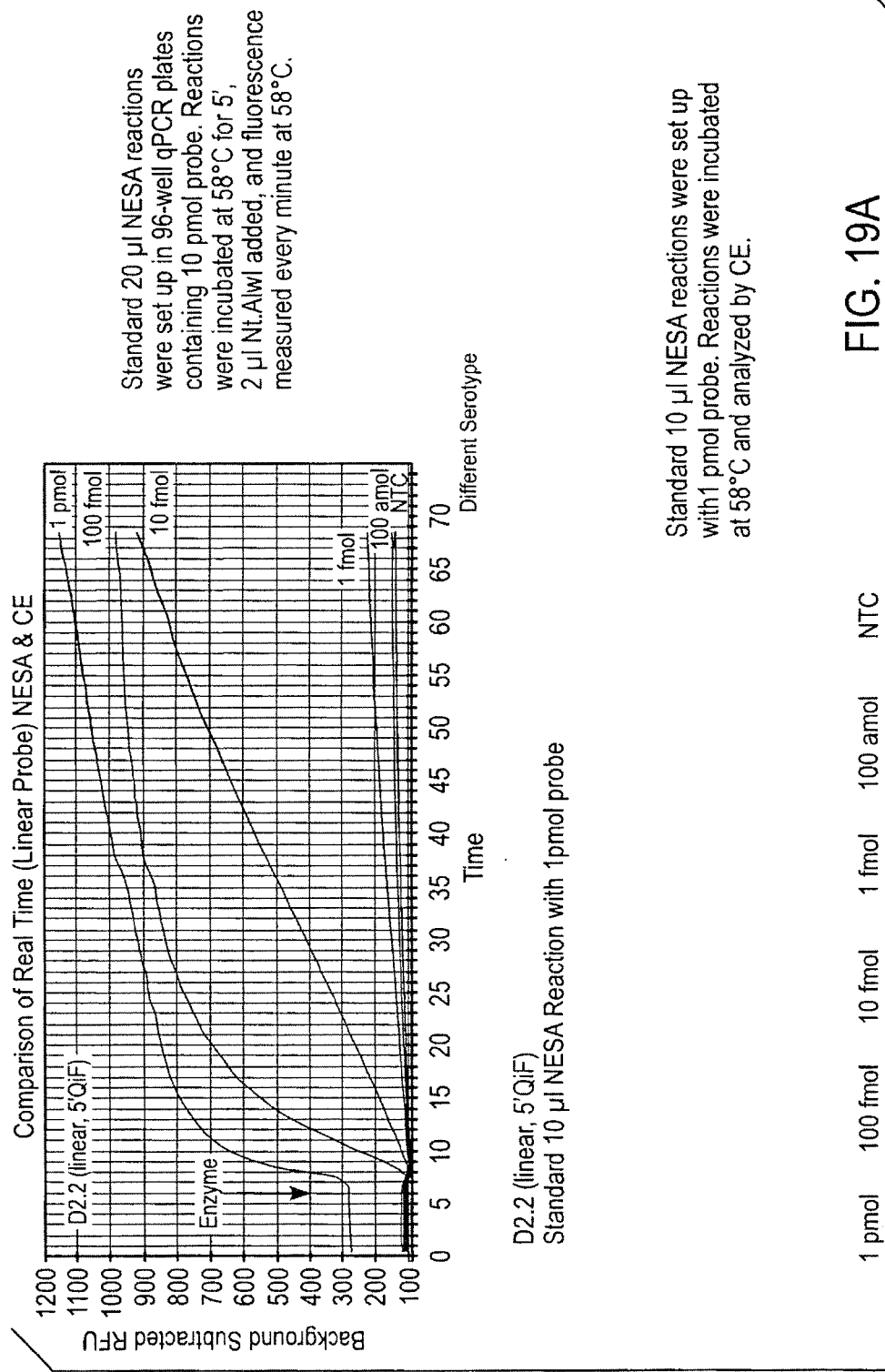
FIG. 19A. Illustrates a comparison of linear probe F/Q assay with capillary electrophoresis assay.
Figure 19B:
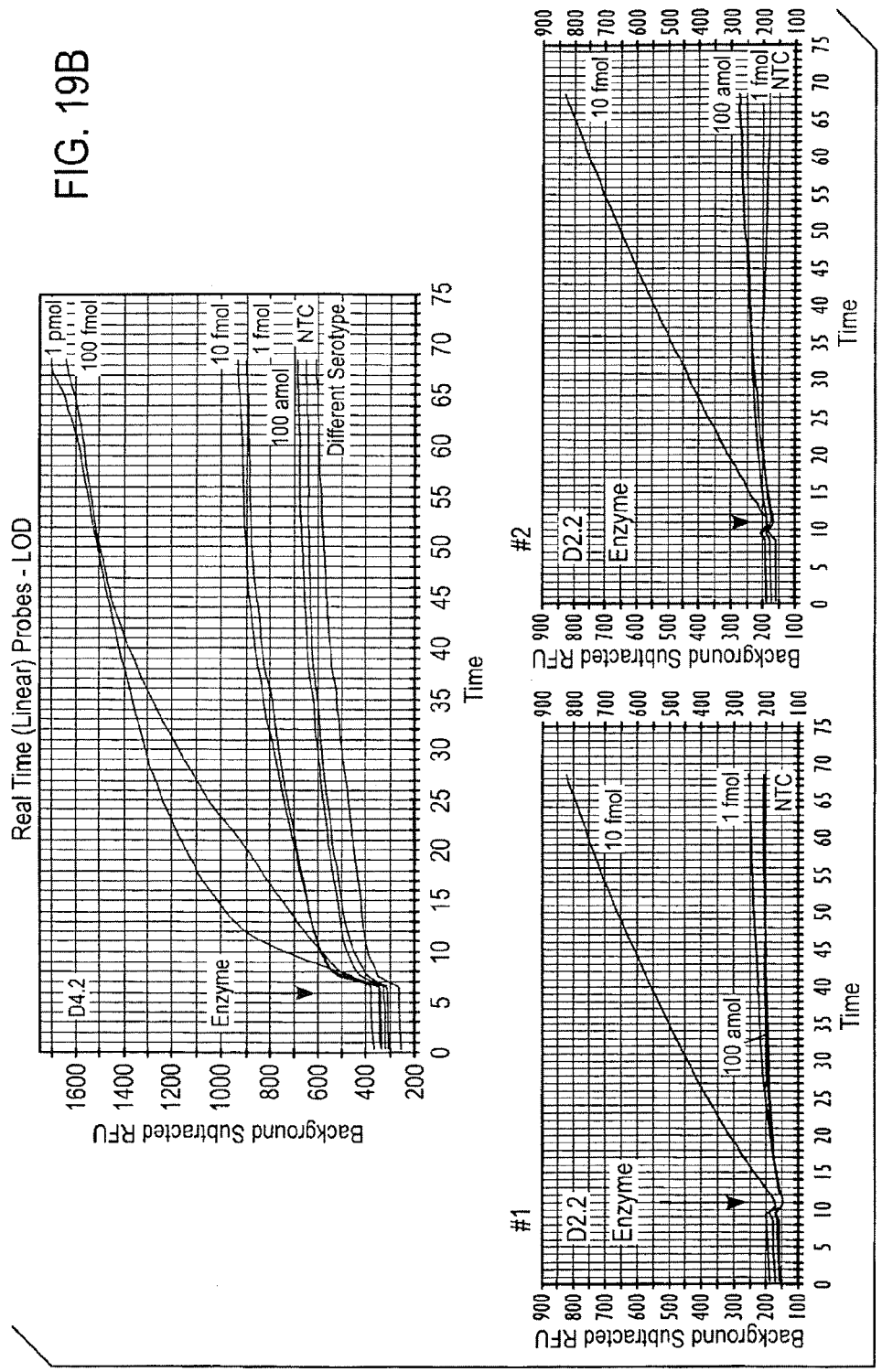
FIG. 19B. Illustrates detection of low concentrations of target using linear F/Q probes.

A linear F/Q probe nicking enzyme streaming assay was compared with an assay employing capillary electrophoresis. For F/Q assay, standard 20 µl NESA reactions were set up in 96-well qPCR plates containing 10 pmol probe. Reactions were incubated at 58° C. for 5', 2 µl Nt.Alwl added, and fluorescence measured every minute at 58° C. For the CE assay, standard 10 µl NESA reactions were set up with 1 pmol probe. Reactions were incubated at 58° C. and analyzed by CE. Results are illustrated in FIG. 19.

Figure 20:
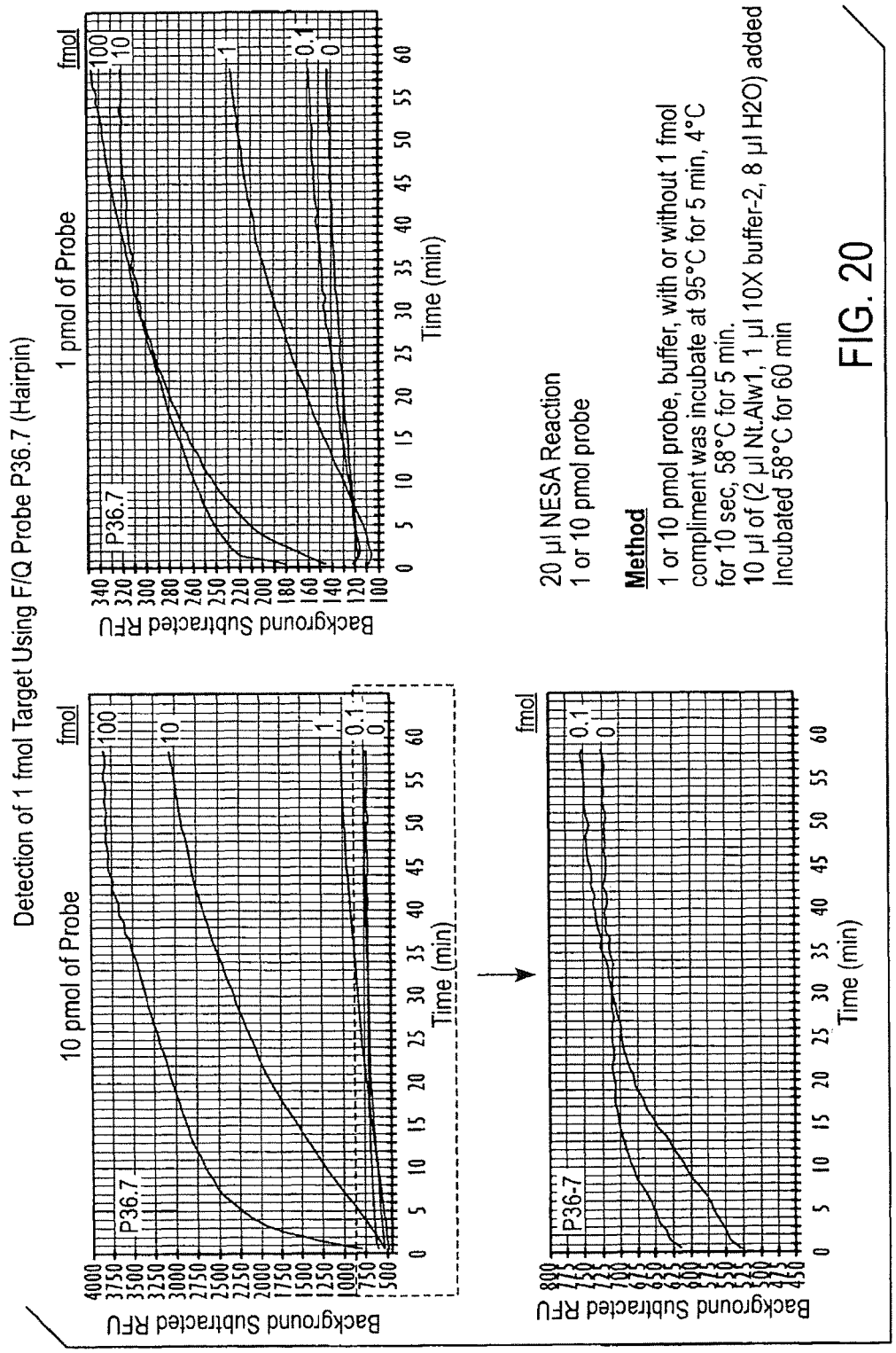
FIG. 20. Illustrates detection of 1 fmol Target using F/Q Probe PChr97.3.
Figure 21:
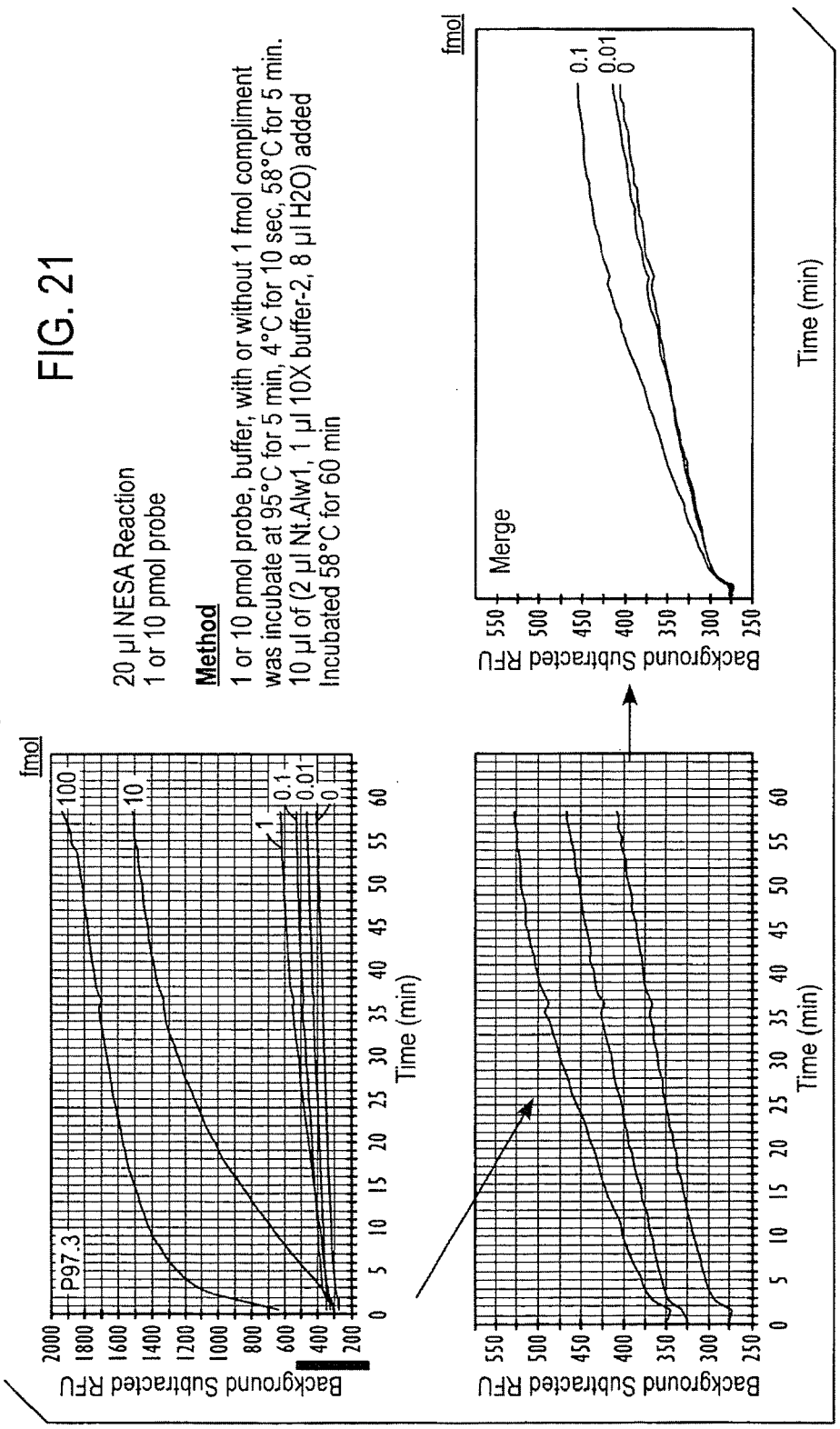
FIG. 21. Illustrates detection of 0.1 fmol Target using F/Q Probe PChr97.3.

FIG. 20 illustrates detection of low concentrations of target using linear F/Q probes. Lowering concentration of the probe can increase signal. FIG. 21 illustrates detection of 0.1 fmol Target using F/Q Probe PChr97.3.

Hairpin F/Q Probes can give very high signal to noise ratios at reduced temperatures. A 20 µl NESA reaction was set up using standard conditions. After 5 min @ 58° C., 2 µl Nt.Alwl was added and the reaction continued at 58° C. The enzyme was heat killed and cooled to 25° C. For the Melt curve, the temperature was then increased 1° C. every 10 sec. Superb signal to background is obtained below 40° C. (background is virtually zero) Results are illustrated in FIG. 22.

Example 7

Surface Coupled Probes

Coupling of 3'-amino modified oligos to Qiagen LiquiChip carboxylated microbeads. A 1 ml suspension of LiquiChip beads was vortexed for 2 min. Aliquots of 125 µl were transferred to microfuge tubes, centrifuged for 3 min at 10,000 g, and the supernatant discarded. The pellet beads were resuspended in 50 µl of 0.1 M MES pH 4.5, and vortexed for 30 sec. One nmol (10 µl of 100 pmol/µl solution) of 3'-Amino modified oligos previously resuspended in 0.1 M MES pH 4.5 were added and vortexed for 30 sec. 10 µl of freshly prepared EDC ([N-(dimethylaminopropyl)-N'-ethylcarbodiimide] Fluka, St Louis, Mo.) were added and the mixture vortexed for 10 sec. Coupling reactions were placed in a light-tight box and agitated every 30 min for 2 hours at 24° C. Coupling reactions were then centrifuged for 3 min at 10,000 g and the supernatant discarded. 1 ml of the wash buffer (PBS pH 7.2, 0.02% Tween-20) was added to each reaction. Pellets were resuspended using a pipette and then centrifuged for 3 min at10,000 g. The supernatant was removed with a pipette and discarded. The washing step was repeated twice. A final rinse of the washed pellet was performed by the addition of 150 µl TE pH 8.0, centrifugation for 3 min at 10,000 g, and removal of the supernatant. The TE equilibrated/washed coupled beads were resuspended in 50 µl TE pH 8.0. These surface-coupled probes (sc-probes) were stored up to four months at 4° C.

Coupling of 3'-amino modified oligos to Maleic Anhydride Coated Polystyrene Plates. Ten µl (100 pmol/µl) of 3'-Amino modified oligos previously resuspended in 0.1 M MES pH 4.5) were added to each well of a reacti-bind amine-binding, maleic anhydride activated plate (clear, 8-well strips) (Thermo Fisher Scientific Inc. Waltham, Mass.). Forty µl of PBS pH 7.4 were added to each well, and mixed by gently pipetting. Wells were sealed with OptiClear (B) film (Biorad, Hercules, Calif.) and incubated in a light tight box for 4 hours at 24° C. Plates were agitated gently every 30 min during incubation. After 4 hours, the supernatants were discarded, and 250 µl of blocking buffer (TE, pH 8.0) were added to each well. Plates were sealed and incubated in the dark with occasional agitation for 1 hour. Following blocking, the supernatants were discarded and the wells washed twice with 250 µl of wash buffer (PBS with 0.05% Tween-20, pH 7.2). Plates were washed twice again with 250 µl of blocking buffer, discarding the buffer each time. To each well, 100 µl of blocking buffer were added and the plates sealed. Plates were stored at 4° C. in the dark. One set of plates was used to test if they could be stored dry. Buffer was completely removed and the plates stored at 4° C. for 48 hours.

Quantifying coupling efficiency of bead coupled probes. To determine the concentration of the beads only, the bead-bound probes were vortexed for 5 sec and diluted 100-fold using MES pH 4.5 and their concentration determined using a hemocytometer. Next, 3 µl of undiluted resuspended probe-beads were added to 7 µl containing 1 µl of 10× DNase I buffer (Promega, Madison, Wis.), 1 µl of DNase 1 (Promega), 5 µl of H2O and incubated at 37° C. for 10 min. 1 µl of stop solution (20 mM EGTA pH 8.0) was added and the reaction incubated at 65° C. for 10 min. Following this DNAse inactivation step, 19 µl of H2O were added to the reaction. Uncoupled beads, and free probe were also DNase treated for use as background controls. Fluorescence was measured using a fluorescent plate reader (excitation 495 nm, emission 520 nm). Sample fluorescence was plotted against a standard curve prepared from serial dilutions of DNAse-treated uncoupled probe. The number of fluorescent oligonucleotides attached to each bead was then calculated for each coupling reaction.

NESA reactions using surface coupled probes (sc-probes). Each NESA reaction contained 1 µl (1 pmol to 10 amol) of target oligonucleotide (the complementary sequence of the probe), 1 µl Restriction Endonuclease Buffer-2 (NEB), 3 µl sc-probes, and 4 µl H2O. The 9-µl mixture was heated to 95° C. for 10 min, 4° C. for 10 sec, then 58° C. for 5 min. Once the reaction had reached 58° C., 1 µl Nt.AlwI (NEB, Ipswich, Mass.) was added followed by incubation at 58° C. for 60 min and then 80° C. for 20 min to stop the reaction.

NESA reactions using sc-probes on plates. Target oligonucleotides (the complementary sequences of the probes) were first denatured for 2 min at 95° C. (5 µl complement (1 pmol/µl), 2.5 µl of 10× NEBuffer-2 (NEB), and 17.5 µl of H2O). Each reaction was added to a well of a plate preheated to 58° C., the plate sealed, and incubated for 5 min at 58° C. 25 µl of preheated diluted Nt.AlwI (2.5 µl 2.5 µl 10×NEBuffer-2 (NEB), 17.5 µl H2O) were then added and incubation continued at 58° C. for 60 min. The reaction was then inactivated by incubating at 80° C. for 20 min. Two µl of each reaction were prepared for CE analysis as described.

Capillary gel electrophoresis (CE). Samples were analyzed using an Applied Biosystems 3130x1 Genetic Analyzer with electrokinetic injection as described previously (6). In brief, NESA reactions centrifuged at 2000 g for 5 min at 24° C. Two µl of the supernatant were diluted 100-fold (20-fold with water and then 5-fold with formamide and then 10 µl were used for injection. A set of Hex™-labeled standards (5, 17, 21, 30, and 50 nucleotides in length) was run with each sample to aid in peak identification.

Real time NESA (rtNESA) using sc-probes. A 10-p l reaction mixture containing 1 µl of diluted complement (1 pmol to 10 amol), 1 µl NEBuffer-2, 3 µl sc -probes, 5 µl H2O was heated to 95° C. for 10 min, 4° C. for 10 sec, then 58° C. for 5 min. Ten µl of diluted Nt.AlwI (2 µl Nt.AlwI, 1 µl of NEBuffer-2, 7 µl of H2O) were added and the mixture incubated for a further 60 min at 58° C. Fluorescence was determined every minute of the 60 min incubation using 5 s reads and excitation/emission wavelengths of 495 nm/520 nm. All rtNESA experiments were run and analyzed using the BioRad iQ5 RT-PCR Detection System. The efficiency of coupling probes to polystyrene beads (4 µm diameter) was investigated. On average, 0.6×10⁶ probes were coupled to each bead. Each bead is supposed to have 10⁸ binding sites, approx 0.5% coupling efficiency. There can be about 3,000 beads per µl. 3 µl sc-probes used per reaction=1.8×10⁹ probe molecules per reaction (~3 fmol).

For capillary electrophoresis the limit of detection can be between 100 and 10 amol (10-17 M) for sc-Probes on polystyrene beads. Samples can be injected for at least 360 s with little increase in background. Samples can be used directly, bead removal is not necessary.

Figure 25:
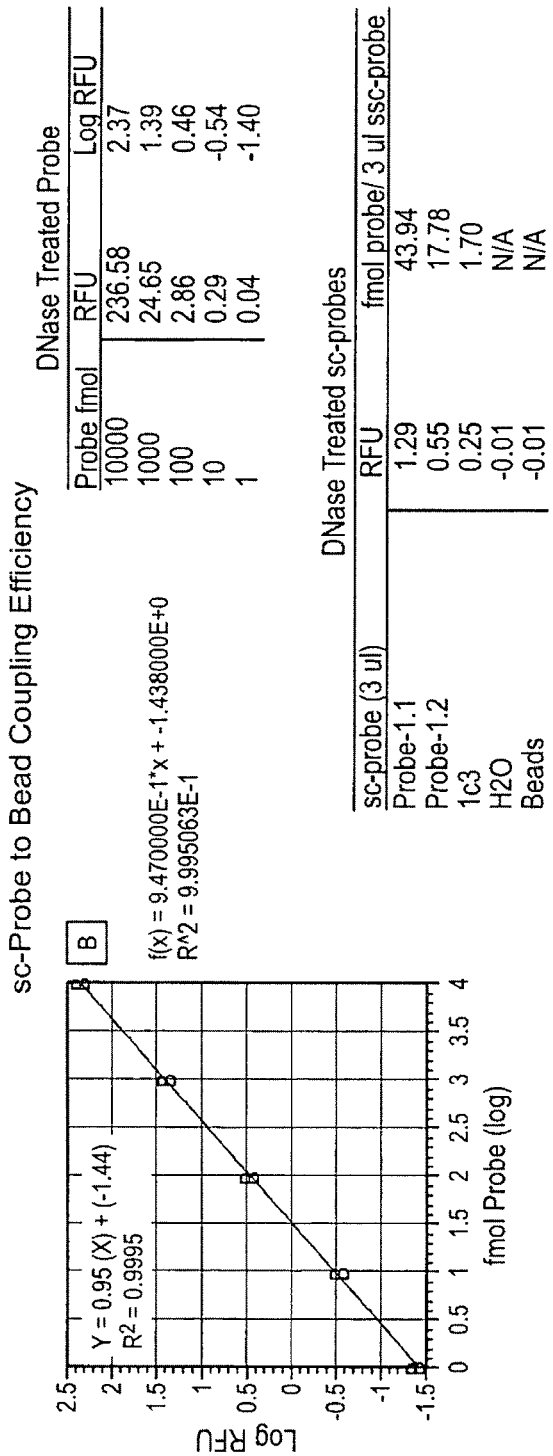
FIG. 25. Illustrates sc-Probe to Bead Coupling Efficiency.

For F/Q sc-Probes on polystyrene beads, real time assays can perform well. Kinetics of sc -probes and uncoupled probes are very similar. There can generally be no increase in background fluorescence during the reaction. For sc-Probes on multi-well plates, very strong signals could be measured by CE. Sc-probe plates are stable desiccated for at least 48 hours and work at least as well as "wet" plates. Desiccated plates are likely a way for long term storage of sc-probes. Results are illustrated in FIG. 25.

TABLE 3

SC probes

| Probe | Sequence (5' to 3') |
|---|---|
| 1 | F-A GGATC TTAC GA AA CTT CGG-AmM |
| 1c3 | F-A GGATC TTAC GA AA CTT CGG-(T12)-AmM |

TABLE 3-continued

SC probes

| Probe | Sequence (5' to 3') |
|---|---|
| 1c12 | AmM(C12)A GGATC TTAC GA AA CTT C-F |
| 1.1 | IB-A GGATC TTAC GAT-FAA CTT CGG-AmM |
| 1.2 | IB-A GGATC TTAC GA AAT-FCTT CGG-AmM |
| 1.3 | IB-A GGATC TTAC GA AA CTTT-FCGG-AmM |
| 1.12 | F-A GGATC TTAC GA AA CTT CGG-BHQ-AmM |
| 1.13 | AmM(C6)-BHQ-A GGATC TTAC GA AA CTT CGGT-F |

These probes have the same base sequence and have been aligned with spaces where necessary. F, FAM; IB, iowa black; AmM, amide linkage, BHQ, black hole quencher 1. Data using the probes in bold are shown in these examples. The other probes gave similar results (data not shown).

Figure 26:
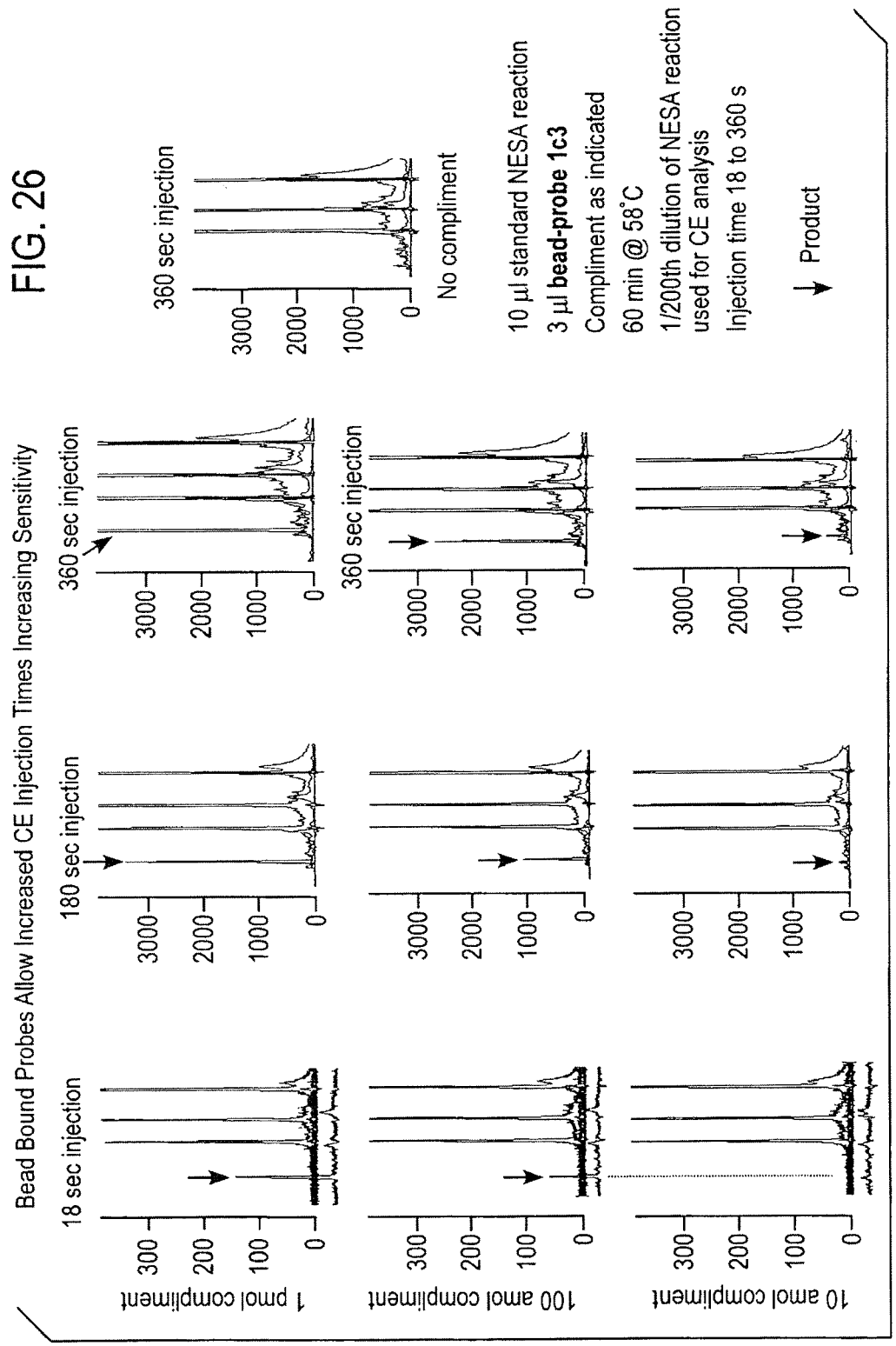
FIG. 26. Illustrates that bead bound probes allow increased CE injection times increasing sensitivity.

FIG. 26: Illustrates that bead bound probes allow increased CE injection times increasing sensitivity.

Figure 27:
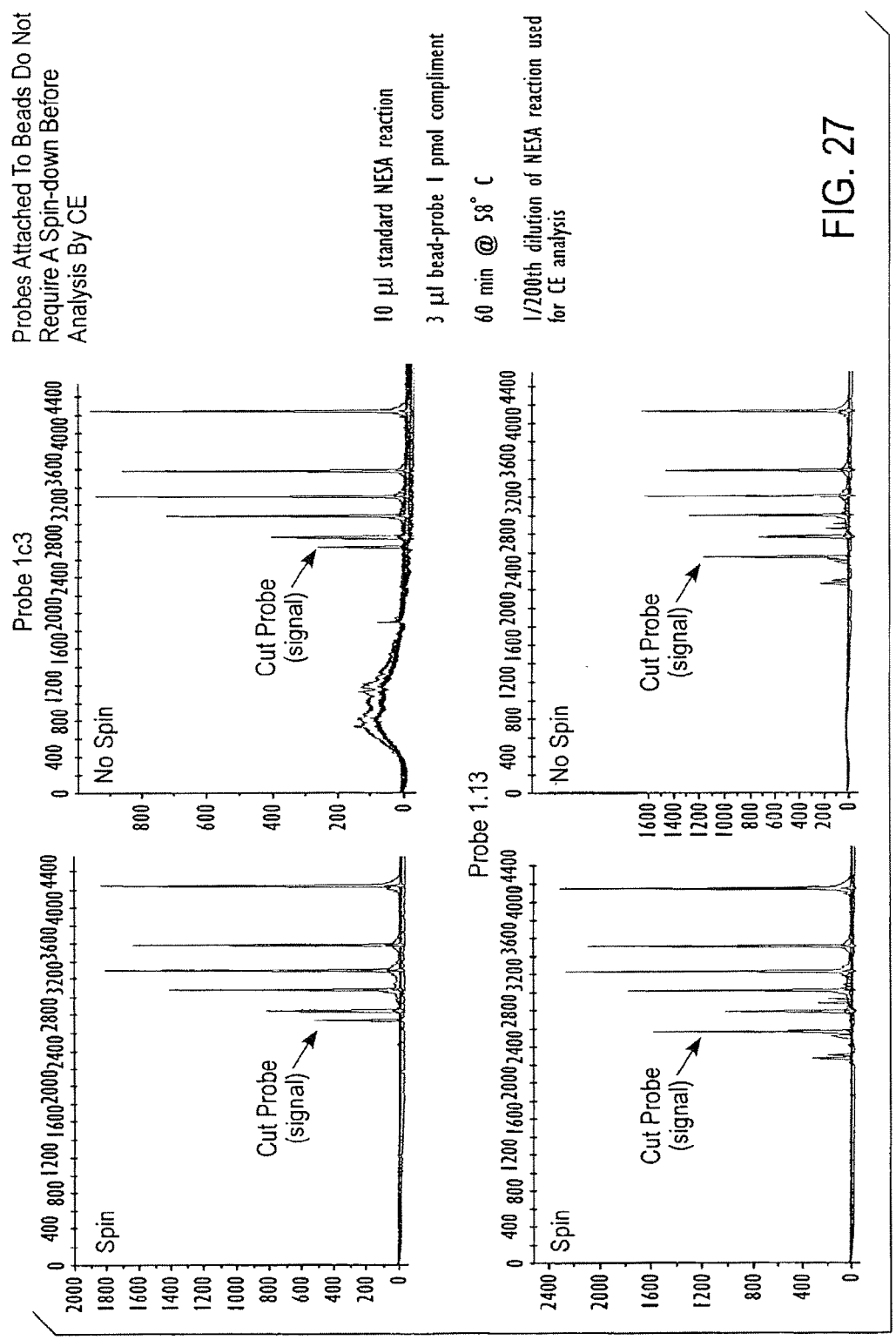
FIG. 27. Illustrates that probes attached to beads do not require a spin-down before analysis by CE.

FIG. 27 illustrates that probes attached to beads do not require a spin-down before analysis by CE.

Figure 28A:
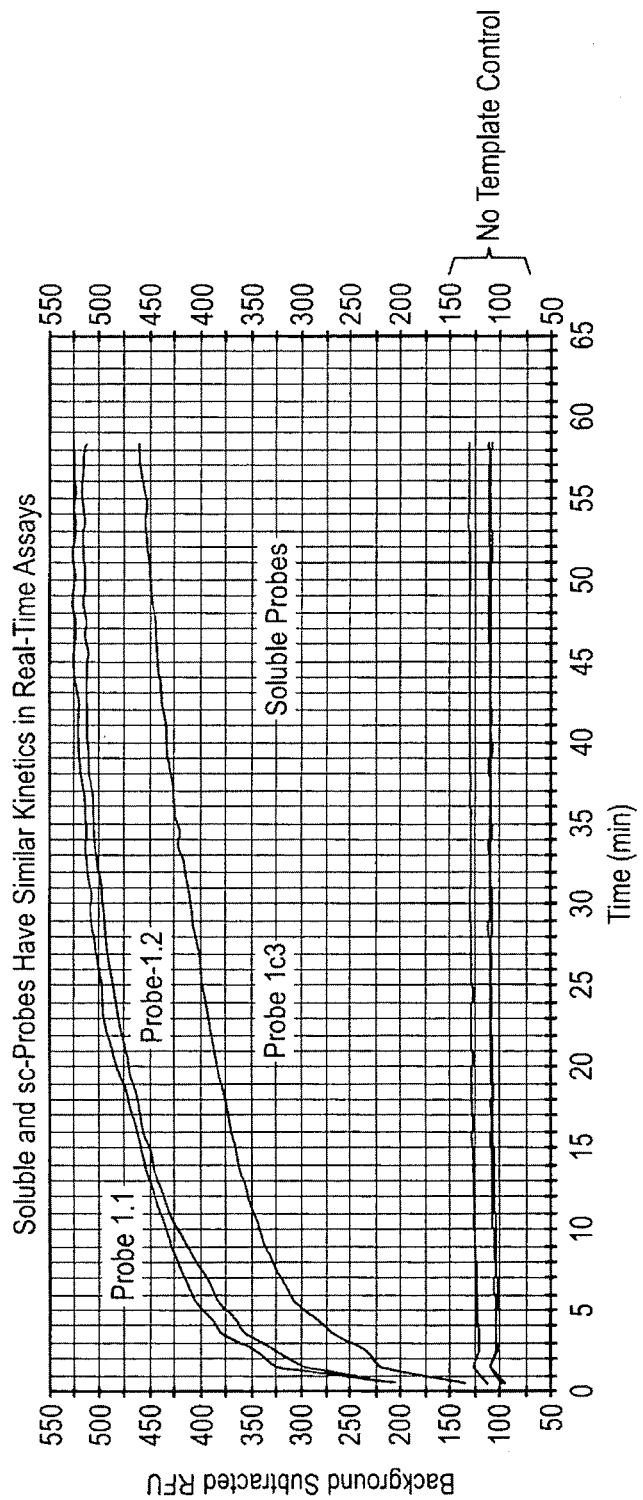
FIGS. 28A-B. Illustrate that (A) soluble and (B) sc-Probes have similar kinetics in real-time assays.
Figure 28B:
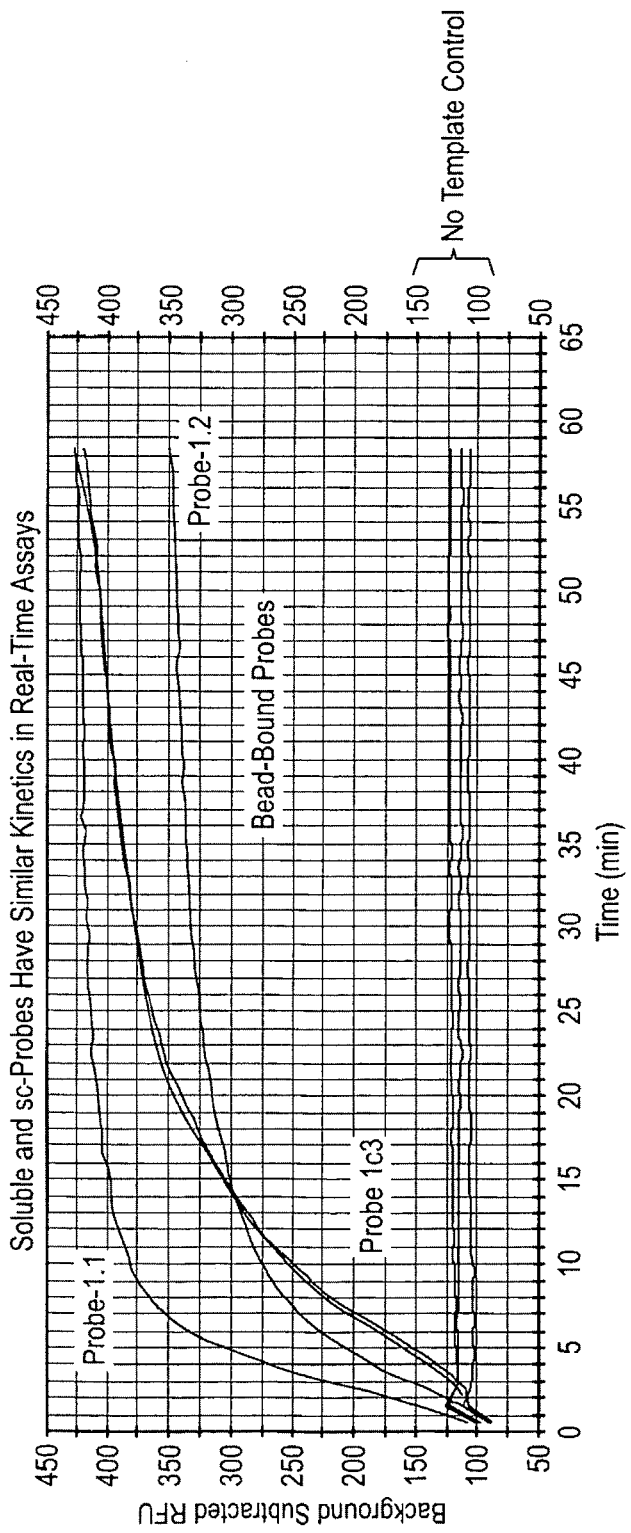

FIG. 28 illustrates that soluble and sc-Probes have similar kinetics in real-time assays. rtNESA Analysis of probes alone versus sc-probes. Briefly, each reaction was done in duplicate +/−1 pmol of compliment. Probe alone reactions contained 2 pmol of probe, sc-probe reactions contained 3 ul of bead-coupled probes. (A). Real time results for probes alone, green—probe1.1, blue—probe 1.2, red—probe 1c3. Three lines at or near the ~100 rfu mark represent no template control reactions, red—probe 1.1, purple—probe 1.2, brown—probe 1c3. (B). Real time results for sc-probes, Green—probe 1.1, light blue—probe 1.2, yellow—probe 1c3. Three lines at or near the ~100 rfu mark represent no template control reactions, pink—probe 1.1, blue—probe 1.2, dark green—probe1C3.

Figure 29:
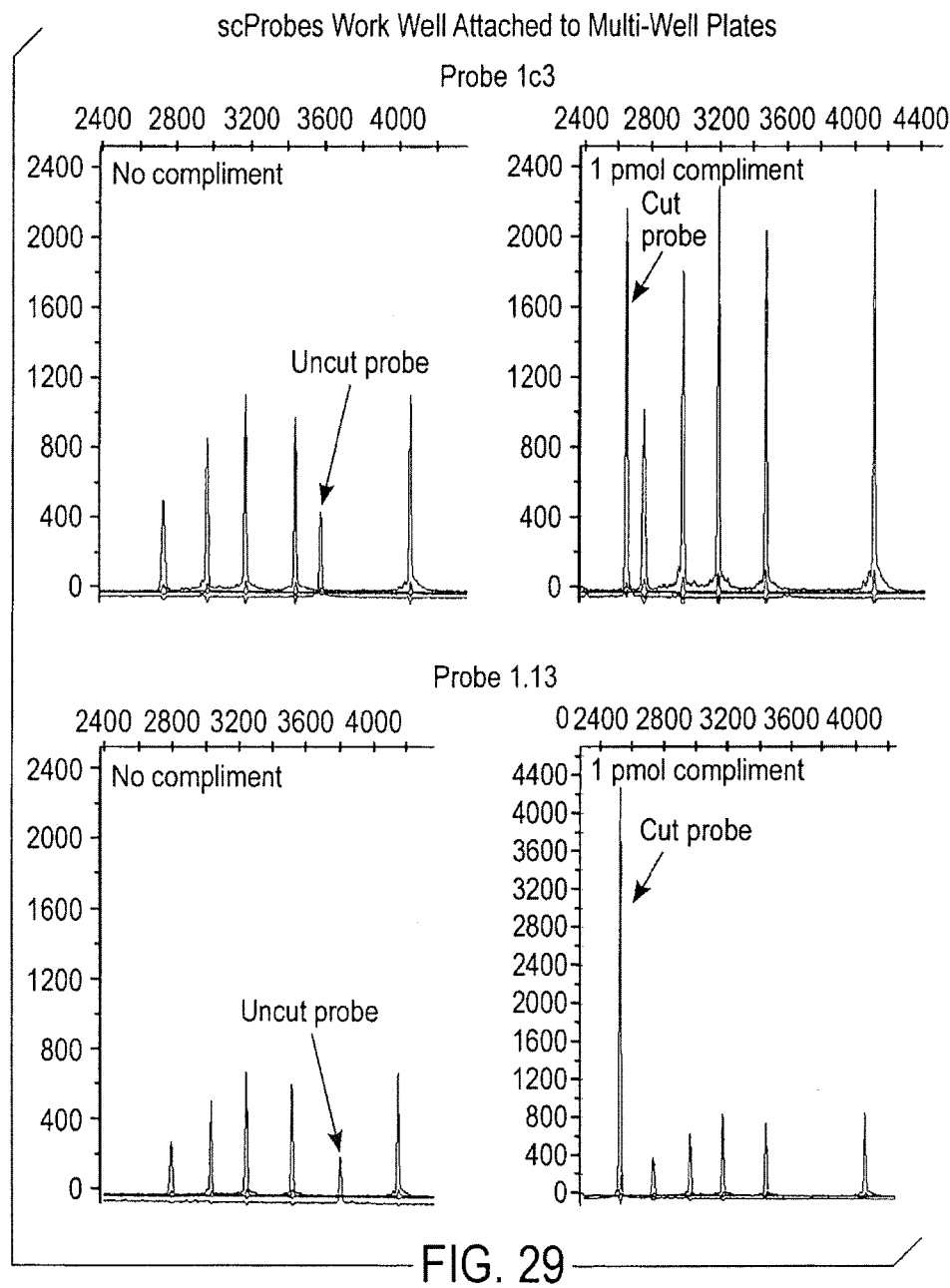
FIG. 29. Illustrates that scProbes work well attached to multi-well plates.
Figure 30:
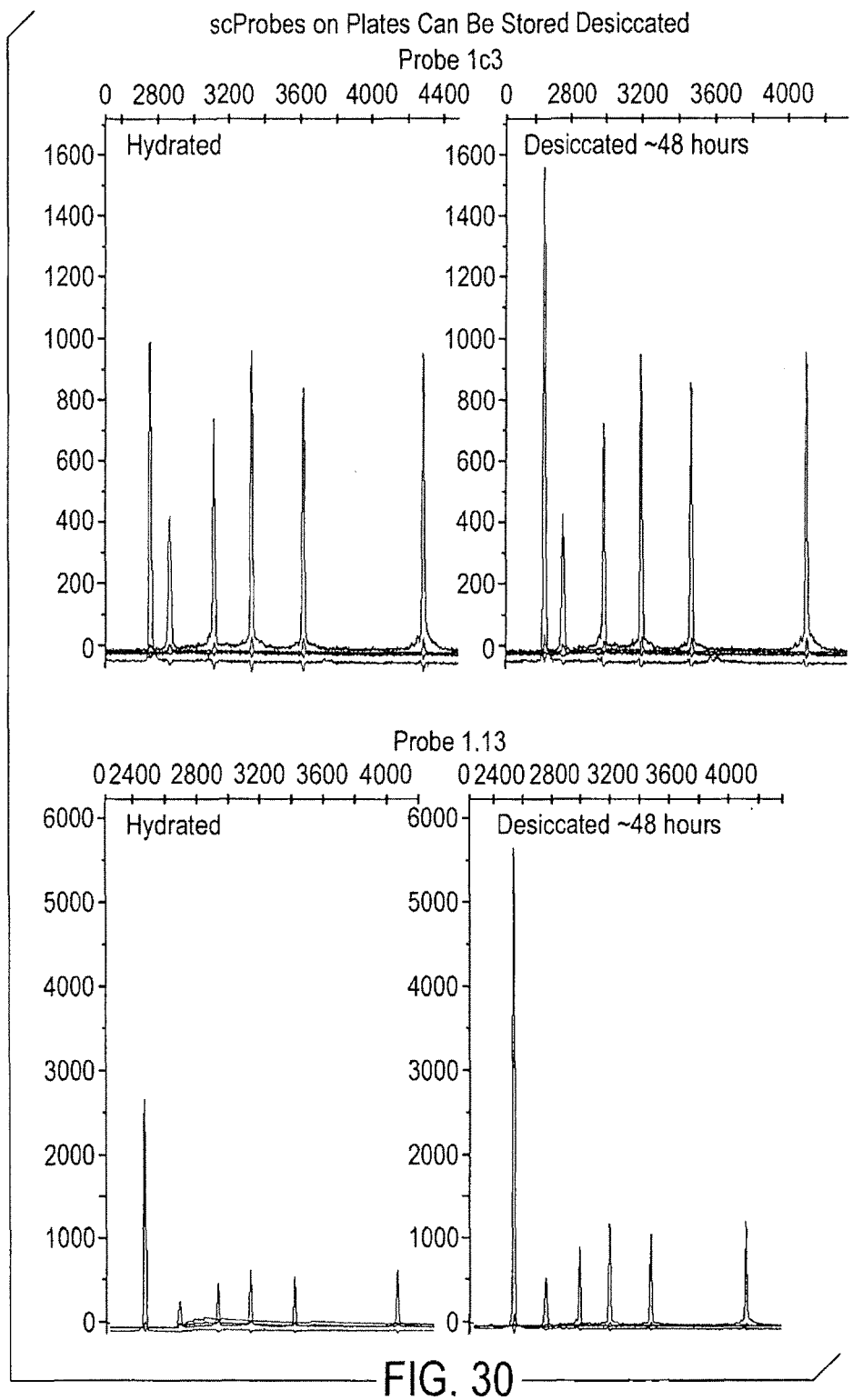
FIG. 30. illustrates that sc-Probes on Plates Can Be Stored Desiccated.

FIG. 29 illustrates that scProbes work well attached to multi-well plates. FIG. 30 illustrates that sc-Probes on Plates Can Be Stored Desiccated.

Example 8

Specific Detection of *B. Anthracis* with a Novel Multiplex Assay Suitable for Crude Environmental Samples Using Whole Genome Amplification and Nicking Endonuclease Signal (References cited in this example are numbered in accordance with the listing at the end of this example.)

Introduction Although culture methods have been used for many years to identify microorganisms, they are not so helpful with very slow growing organisms, with those that are difficult or impossible to grow in vitro, and those organisms that do not survive harvesting methods such as filtration. For these reasons, molecular biological methods have been developed that allow the rapid identification of bacteria (7, 10, 16, 17, 19). The leading technique for this is undoubtedly the polymerase chain reaction (PCR), especially quantitative PCR (qPCR), that can not only identify an organism but can also determine relative bacterial load (15, 22). Although PCR is exquisitely sensitive and can be multiplexed, albeit with a usual decreased sensitivity, there is a caveat to using PCR as a detection method. PCR detection from complex samples, such as environmental or clinical samples, often requires purification of the DNA to remove inhibitors of the PCR reaction such as heme, humic acids, chelating agents, and metals (3, 4, 12, 21). These inhibitors can give rise to false negatives that could be devastating in the case of medical diagnostics and catastrophic in the case of environmental surveillance for biowarfare agents. Unfortunately the isolation and purification processes necessary to obtain pure DNA are often time consuming and difficult with field studies, while the efficiency of recovery from such methods can vary and affect the sensitivity of PCR detection (18). We have recently described a technique called nicking endonuclease signal amplification (NESA) that uses fluorescent oligonucleotide probes in isothermic cycles of hybridization, cleavage, and dissociation to detect the presence of low levels of specific genomic DNA (5). In this report, we show that a combination of multiple displacement amplification and NESA can be used to detect genomic DNA in crude environmental samples without the need for DNA with samples that are refractory to PCR. We show the general utility of the system by developing NESA probes specific for *B. anthracis* chromosomal DNA as well as the *B. anthracis* plasmids pX01 and pX02 that are required for virulence. These probes were combined in a multiplex assay that distinguishes between strains of *B. anthracis*.

Materials and Methods Oligonucleotides, Genomic DNA, Environmental Samples. Oligonucleotides were obtained from Integrated DNA Technologies (Coralville, Iowa). All probes were fluorescently labeled at the 5' position with 6-carboxyfluorescein (FAM™) and were purified by ion exchange HPLC. Five oligonucleotide size standards (5, 17, 20, 30 and 50 bases) were synthesized with hexachlorofluorescein (HEX™) at their 5' ends. Genomic DNAs were obtained from Zyagen, San Diego, Calif. (Bovine, Cat, Dog, Monkey, Mouse, Sheep, Porcine, Equine, Human); Lawrence Livermore National Laboratory (Chicken, *Drosophila melanogaster*, Rabbit, Rat, Flea, Mosquito); Johns Hopkins Bloomberg School of Public Health (Tick, *Ixodes scapularis*); BEI, Manassas, Va., (*B. anthracis* strains Ames BEI D2005259004, Vollum BEI D2005276004, GT68 BEI D2005255003, Δ Sterne BEI D2004322001, GT41 BEI D2004056001, BACI055 BEI D2005027001, GT28 BEI D2006030002A1, Sterne BEI D2005075001, GT3 BEI D2004050007; *Yersinia pestis* strains F361/66 South America 1966 BEI D2005041002, India 1898 BEI D2005056003, 342 15-91 Russia 1960 BEI D2005060001, 338 ZE942122 Zimbabwe 1994 BEI D2005042001, 346 16-34 Vietnam 1970 BEI D2005056002); The Naval Medical Research Center, Silver Spring, Md. (*B. anthracis* Ames); ATCC, Manassas, Va. (*Mycobacterium smegmatis, Thermotoga maritima, Borrelia burgdorferi, Chlorobium tepidum, Bacteroides fragilis, Shewanella oneidensis, Pseudomonas aeruginosa, Staphylococcus lugdunesis, Staphylococcus haemolyticus, Staphylococcus epidermidis, Staphylococcus saprophytics, Staphylococcus schleiferi, Bacillus thuringiensis, Methanosarcina mazei, Spiroplasma ciṛ, Sulfolobus solfatahcus, Lactobacillus plantarum, Pyrococcus funosus, Streptomyces avidinii, Yersinia enterocolitica, Neisseria meningitidis, Paenibacillus sp., Helicobacter pylori, Deinococcus radiourans, Clostridium acetobutylicum, Bacillus cereus, Rhodobacter Saccharomyces cerevisiae, Candida albicans*); U.S. Army Edgewood Chemical Biological Center (ECBC), Aberdeen Proving Ground, Md. (*S. anthracis* strains. Ames, ANR1, NNR-0.1, NNR1- 0.1, VNR1- 0.1,. Sterne; *Yersinia pestis* strains 9108101, A1122, Amal, 9800419, 9808723, Harbin; *Staphylococcus aureus* enterotoxin B positive strains ATCC 13566, 14458, 19095, 27664, 51651, 51811, 51811; *Bacillus cereus* ATCC 14579, *Bacillus subtilis* ATCC 27370, *Bacillus thuringiensis* BGSC 4AZ1, *Bacillus thuringiensis* BGSC 4G1); Molecular Staging Inc. (*E. coli, B. subtilis*). Genomic DNAs from pathogenic organisms were guaranteed not to contain infectious agents by the suppliers and licenses/permits were obtained from the appropriate agencies for purchasing and shipping. The Georgetown University's Institutional Biosafety Committee approved use of the genomic DNAs. BioWatch filter pieces were obtained from Lawrence Livermore National Laboratory. Crude extracts of these environmental filters were made by placing the filters in 2 ml screw cap vials along with 300 µl each of 2 types of acid-washed glass beads, particle size=106 µm (Sigma G4649) and 425-600 µm (Sigma G8772), and 600 µl TE pH 8.0. Tubes were shaken in a mini bead beater (Biospec Products, Inc #3110BX) at 4800 rpm for 3 min. Vials were microfuged at 13,200 rpm for 5 min and 500 µl of the aqueous phase was then transferred to a fresh tube. These crude samples had some colored particulate matter in them and some were viscous. These extracts were used in experiments to compare the ability of NESA and PCR to detect bacteria in crude environmental samples. Two sets of purified DNA were obtained from Lawrence Livermore National Laboratory to be used in the screening of probes. One set consisted of 96 pools of DNA representing 2000 BioWatch filters. The other set consisted of DNAs isolated using the PowerSoil DNA Isolation Kit (MO BIO Laboratories, Inc, Carlsbad, Calif.) from 54 soil samples from geographically diverse regions of the United States.

Whole Genome Amplification of Genomic DNA. Genomic DNAs (10 ng) were amplified by multiple displacement amplification (MDA) (5) using the REPLI-g Kit from Qiagen (Valencia, Calif.) according to the manufacturer's instructions. Reactions were incubated at 30° C. for 16 hours, followed by heat inactivation of the polymerase at 65° C. for 3 minutes. MDA DNA was quantified using the PicoGreen assay using the manufacturer's protocol (Invitrogen), and specificity of amplification by PCR analysis.

Amplification of *E. Coli* Genomic DNA in the Presence of BioWatch Extracts. BioWatch samples were mixed by pipetting up and down to insure resuspension of particulate matter in the samples immediately prior to transfer to a 96-well PCR plate. Approximately, 100,000 *E. coli* cells, in a suspension of 0.5 µl PBS, were added to each sample. Following the addition of the cells to the sample, the protocol for "Whole Genome Amplification from Blood or Cells" (REPLI-g Handbook, Qiagen, January 2005) was followed with the following exception: the volume of nuclease-free water in the master mix was reduced from 27 µl to 24.5 µl to account for the additional volume from the BioWatch samples. MDA reaction products were diluted 40 fold with TE buffer (10 mM Tris-HCl, 1 mM EDTA, pH 7.5). One µl of diluted MDA reaction was quantified using a Quant-iT PicoGreen dsDNA Reagent Kit (Invitrogen) according to the manufacturer's instructions. PicoGreen assays were read on a Tecan GENios microplate reader. BioWatch samples were tested for the ability to interfere with the PicoGreen assay by directly adding un-amplified BioWatch sample to a PicoGreen assay mix; no interference with quantification was observed.

Locus Representation of BioWatch MDA Samples. MDA reaction products were diluted 4000-fold with TE buffer (10 mM Tris-HCl, 1 mM EDTA, pH 7.5). 1 µl of diluted MDA sample was added to a PCR reaction (0.5 units Platinum Taq polymerase (Invitrogen), 0.3 µM each of forward and reverse primers, 0.25 µM TaqMan probe, 20 mM Tris-HCl (pH 8.4), 50 mM KCI, 5 mM MgCl2, 1 mM dNTPs, 1×Rox reference dye (Invitrogen)). Reactions were performed and quantified with an Applied Biosystems 7300 Real Time PCR system under the following conditions: 10 min at 95° C., followed by 40 cycles of 95° C. for 15 sec and 60° C. for 1 min. The sequences of the PCR primers and TaqMan probes for the ExoV and OmpA loci have been published previously (20).

Nicking Endonuclease Signal Amplification (NESA). NESA reactions were performed as previously described (11). In brief, 1 pmole fluorescently labeled probe, 1 µl NEBuffer 2 (New England BioLabs), 1 to 4 µl MDA genomic DNA and dH2O to a total volume of 9 µl were added to thin-walled PCR tubes or microplates. Samples were incubated at 95° C. for 10 min to denature the genomic DNA and then equilibrated at 58° C. for 5 min. One µl (10 U) of Nt.Alwl (New England BioLabs) was added and the reaction incubated at 58° C. for 1 h. The enzyme was denatured by heating the samples to 80° C. for 20 min. Reactions were stored at 4° C. until analysis by capillary electrophoresis (CE) or at −20° C. for long-term storage. Multiplex assays for B. anthracis were set up with 1 pmole each of a chromosomal, pXO1 and pXO2 probe. The reaction was kept at 10 µl by reducing the volume of water added. In the case of large-scale screening, the NESA reactions were processed using a Beckman Biomek® FX robotic workstation.

Capillary Gel Electrophoresis. NESA reactions were analyzed using an Applied Biosystems 3130x1 Genetic Analyzer (Foster City, Calif.) using a 16 capillary array; electrokinetic injection was used in all cases. The distance from the loading point to the detector was 35 cm. POP -6™ polymer from Applied Biosystems was used with an injection voltage of 1.2 kV and a loading time of 18 seconds. Run voltage was 15 kV for 10 minutes; oven temperature was set at 60° C. Prior to loading on the ABI 3130xI, the reactions were diluted 100-fold: a 20-fold dilution with water followed by a 5-fold dilution with formamide. Final loading volume was 10 µl. A set of 5 Hex™-labeled standards was run with each sample to aid in peak identification, which was performed using GeneMapper® software (Applied Biosystems).

Figure 31A:
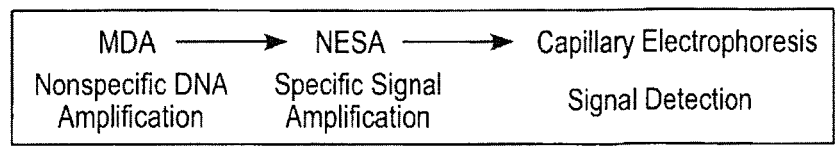
FIGS. 31A-C. Illustrate an exemplary assay: (A) an overall design; (B) nonspecific whole genome amplification using MDA; and (C) specific analysis using NESA.
Figure 31B:
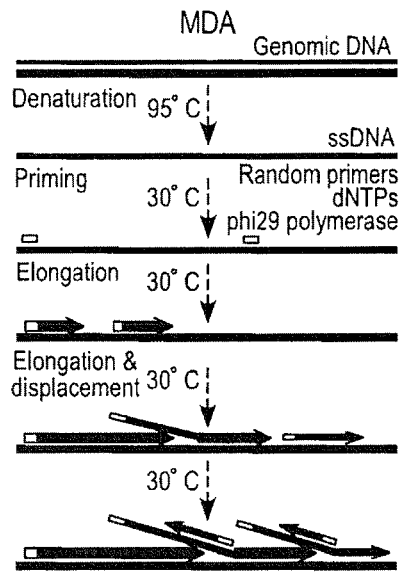
Figure 31C:
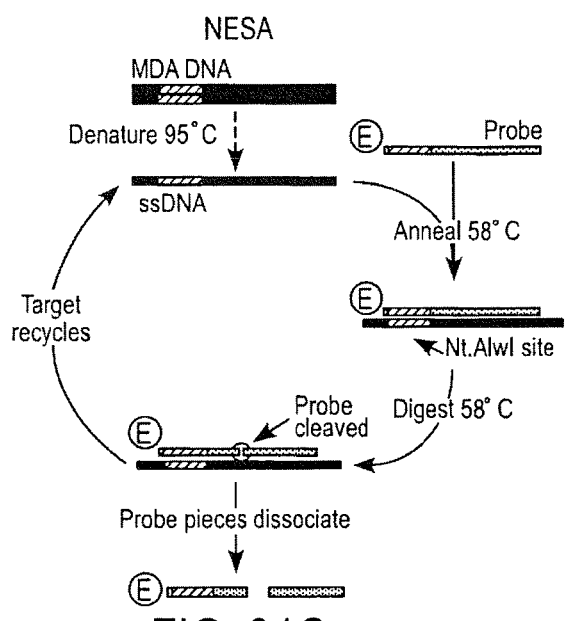
Figure 32:
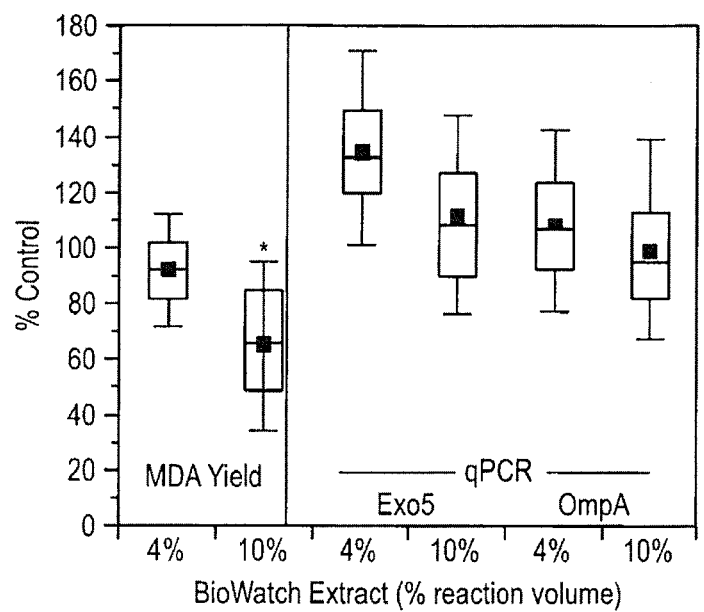
FIG. 32. Illustrates that MDA can amplify DNA from environmental collection filters.
Figure 33:
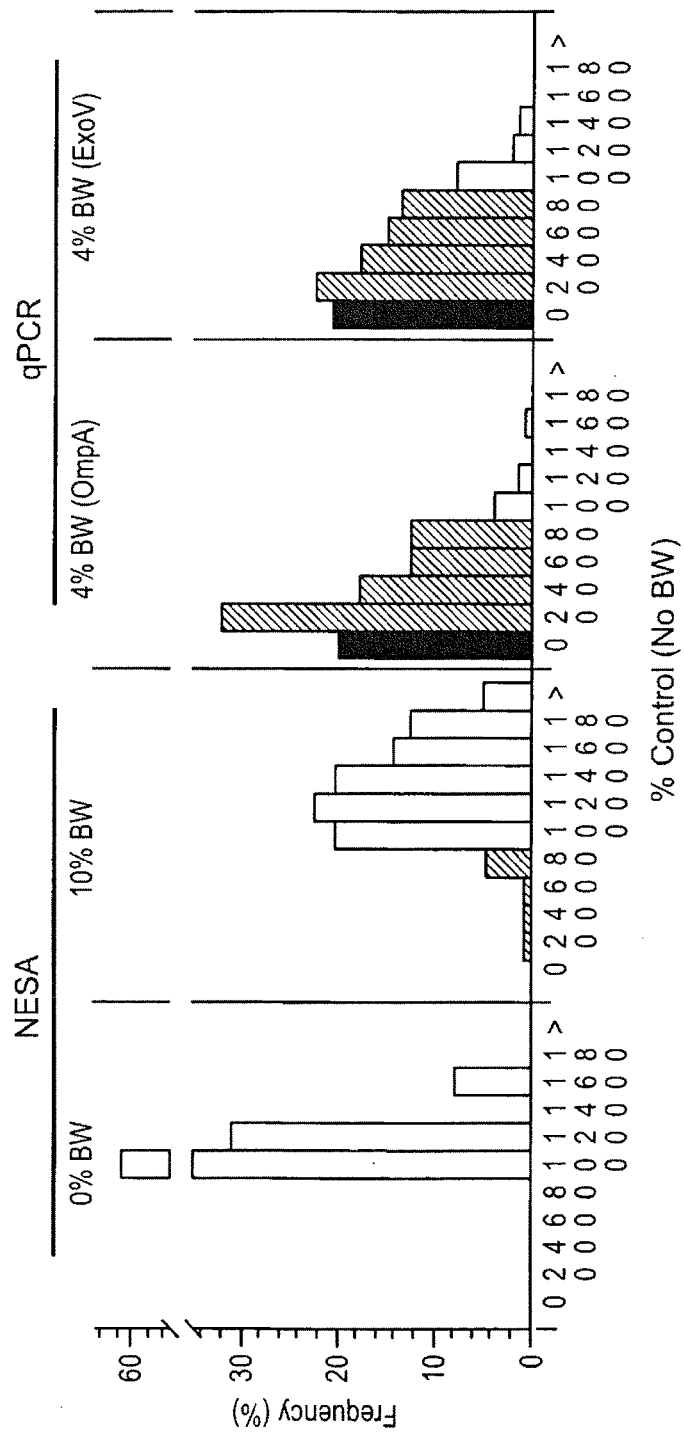
FIG. 33. Illustrates efficient detection of genomic DNA in crude environmental samples by NESA compared with qPCR.

Results. A combination of MDA and NESA reproducibly detects bacterial contamination in crude (BioWatch) environmental samples. Analysis of the DNA in environmental samples is usually constrained by low levels of DNA and the presence of inhibitors of enzymatic reactions (23). We designed our assay to largely overcome both of these constraints by first amplifying DNA nonspecifically using MDA (14) and then detecting specific sequences with NESA (FIG. 31). MDA uses phi29 DNA polymerase to amplify total DNA using random hexamers primers and dNTPs. The product of the reaction is highly concentrated DNA that represents the starting DNA with little loss of complexity (5). This reaction can be performed on crude biological samples such as bacterial cultures and whole blood without the need to first purify DNA (2, 8, 9, 24). It is also highly sensitive, amplifying DNA from as little as one bacterium (13, 20). A schematic of the MDA reaction is shown in FIG. 1A. To determine whether MDA was capable of amplifying DNA from crude environmental samples, we prepared extracts from 204 filters obtained from the BioWatch Program by bead beating and centrifugation (Methods). E. coli (100,000 cells) were added to either 2 µl or 5 µl aliquots of the extracts and MDA performed in a total volume of 50 µl (the filter extracts represented 4% or 10% of the MDA reaction volume respectively). There was no significant effect of adding 4% of the crude extract on the overall synthesis of DNA as measured by PicoGreen assays (FIG. 32). However, when the relative volume was increased to 10%, a significant decrease in overall DNA synthesis occurred. We then used TaqMan qPCR to markers, OmpA and ExoV. No significant amplification bias of these markers was observed in MDA reactions containing either 4% or 10% levels of the crude samples even though the 10% reactions had shown a significant decrease in overall DNA synthesis. We next tested whether NESA could be performed on the MDA samples described above that had been amplified in the presence of the crude environmental samples. MDA DNAs amplified in the presence of 10% of the environmental extracts were subjected to NESA without prior DNA purification (FIG. 3). Of 203 samples tested, one sample essentially failed (0.2% of control), and two samples were inhibited more than 50% (28% and 44%), However, the vast majority of samples showed very little inhibition and overall the samples with added environmental extract averaged 125±34% of the control.

qPCR is Sensitive to Inhibitors in the Environmental Extracts PCR analysis is known to be particularly sensitive to the presence of contaminants. We thus suspected that the crude environmental samples we were using would act as poor templates for PCR. PCR reactions were set up in which 10% of the PCR reaction consisted of the environmental extract, however these reactions all failed to give a signal (not shown) and so the experiment was repeated with 4% extract (FIG. 33). Two genetic markers were used OmpA and ExoV. In both cases, approximately 20% of samples (40 OmpA and 42 ExoV) failed to amplify and only 5 to 11% (10 OmpA and 23 ExoV) of samples gave signals above 80% of control. This is in contrast to the NESA experiments where greater than 94% (191 samples) gave signals over 80% of control.

Development of a Multiplex Assay for B. Anthracis The sensitivity of the MDA/NESA assay and its resistance to environmental contaminants makes it an attractive assay system to detect bacterial contamination. To demonstrate the utility of the assay, we set out to develop a system for designing and screening NESA probes capable of identifying specific microorganisms. Our initial goal in this was to develop probes that could identify individual strains of B. anthracis.

Figure 34A:
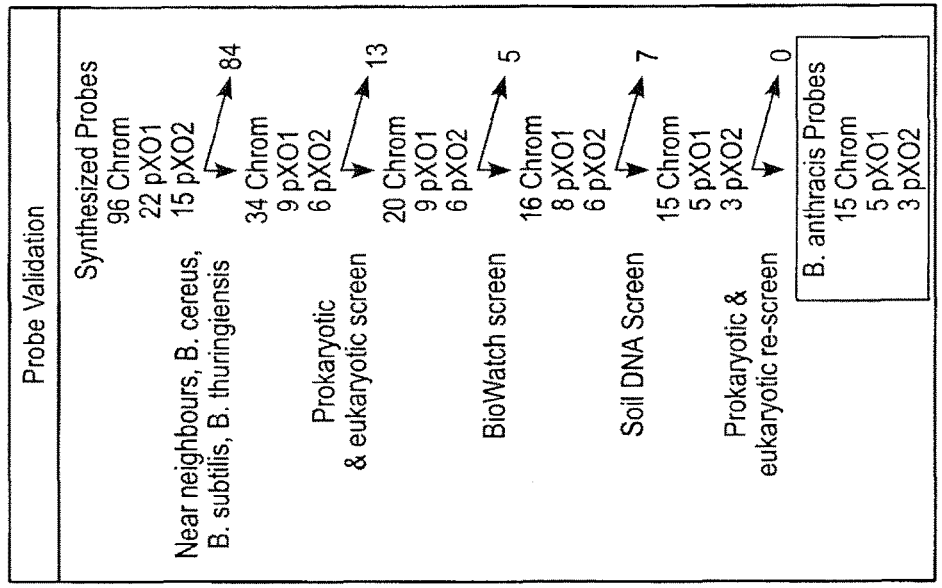
FIGS. 34A-B. Illustrate a probe screening: (A) probe design and (B) probe validation.
Figure 34B:
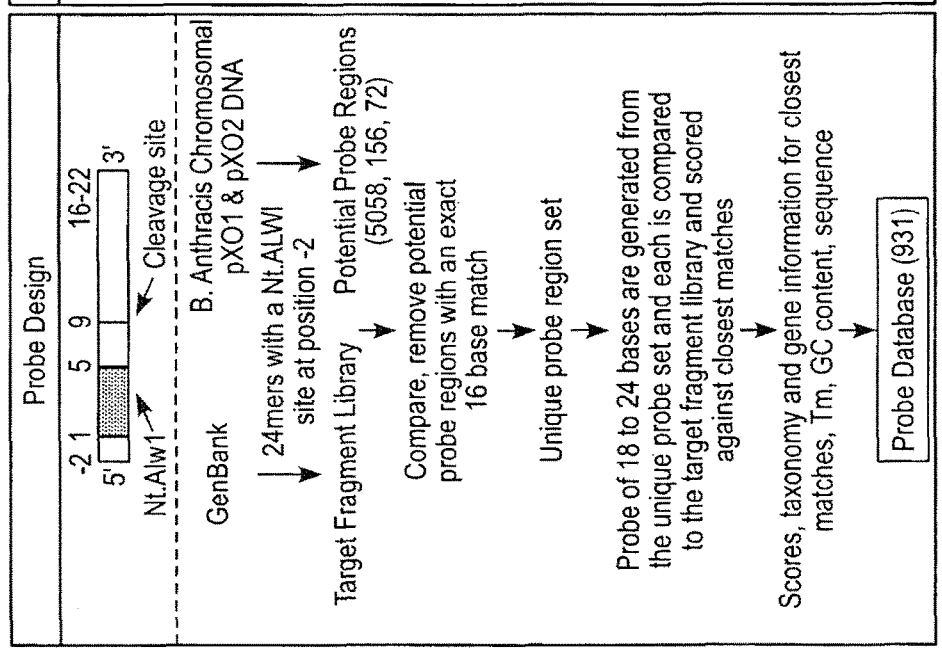
Figure 37A:
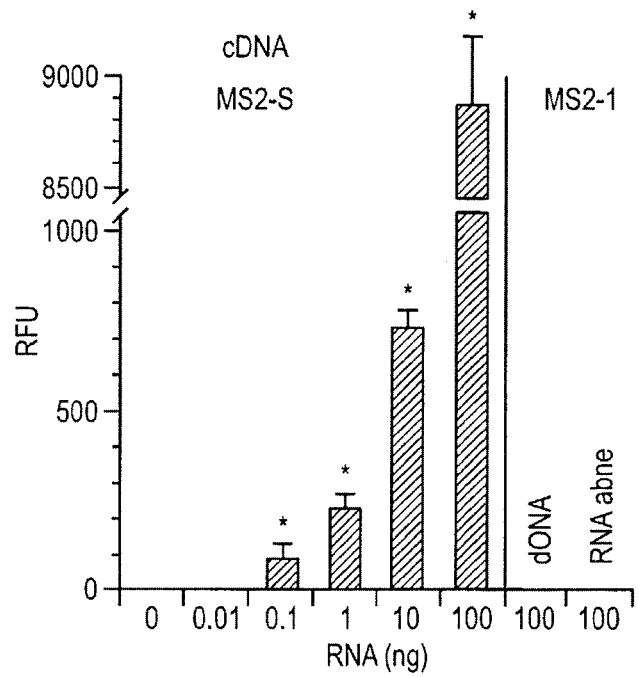
FIGS. 37A-D. Illustrate that the rNESA MS2 assay is more sensitive than rtPCR. A. MS2 RNA was reverse transcribed and subjected to NESA using either a probe specific for the cDNA (MS2-S) or for RNA itself (MS2-1). The sample marked RNA alone was not reverse transcribed. B. MS2 RNA was reverse transcribed and amplified by MDA. 2 μl of the MDA reaction were used in NESA with the MS2-1 probe. C. The MS2 RNA dilutions used in A were amplified using two sets of published primers (Table 1) (O'Connell et al. 2006). N/A, no specific amplification was detected. D. The rtPCR reactions in C were subjected to melting curve analysis. Reactions with starting RNA levels of 10 fg of RNA or more had similar profiles and only the 10 fg reaction is shown. Neither the no RNA control nor the 1 fg reaction had detectable specific amplification. All reactions were performed in triplicate; the standard deviation is shown. * Significantly different from the no RNA control (T-Test, p<0.01)
Figure 37B:
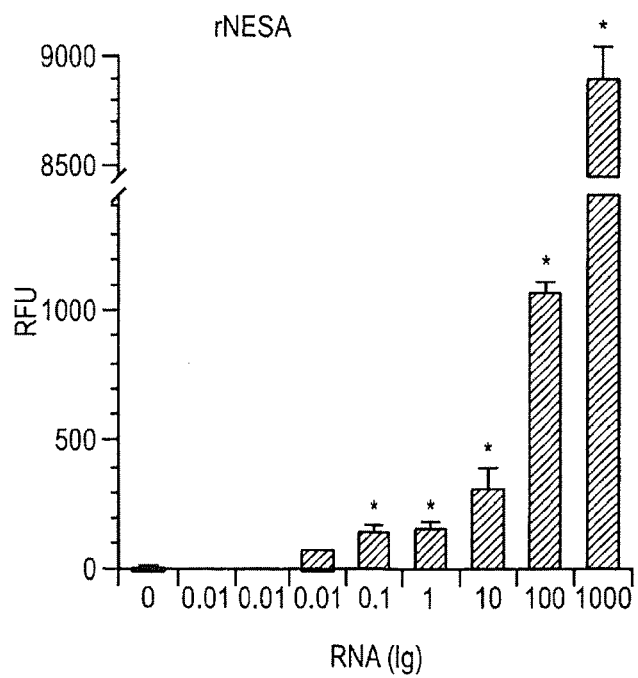
Figure 37C:
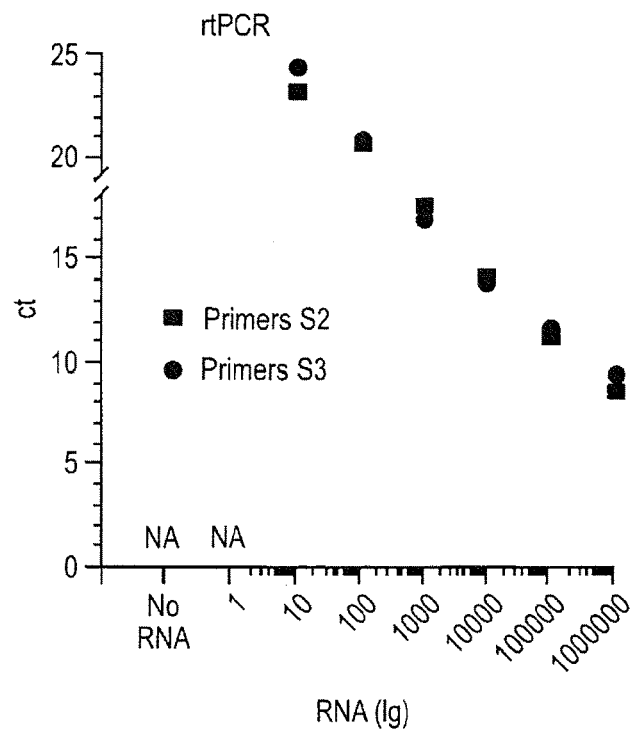
Figure 37D:
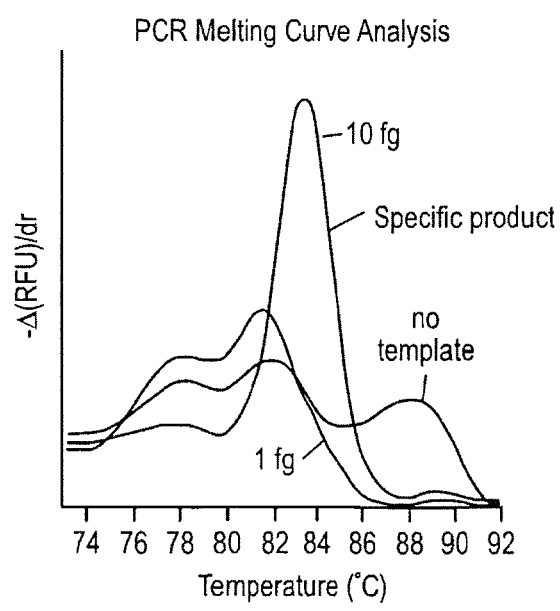

Probe Design—Bioinformatics For the purposes of the bioinformatics screen, the Nt.Alwl site was placed 2 bases from the 5' end of the probe (FIG. 34) placing the restriction site 4 bases 3' of this. The length of the probes varied between 18 and 24 bases. The bioinformatics pipeline is shown in FIG. 34. All Nt.Alwl sites were first identified. For each site the DNA sequence was extended 1 base 5' and 10 bases 3' and the resulting 16 base sequences were compared to the GenBank (non-redundant) database and identical sequences were discarded. Of the 5286 Nt.Alwl sites in B. anthracis (chromosomal and plasmid sites) 133 were unique. These 133 sequences were extended at the 3' side to form all the sequences from 18 to 24 bases. Each of these 931 sequences (7 sequences per unique 16mer) were then compared against the GenBank (non redundant) database and the closest matches ranked using the scoring matrix shown in Table 1. The overall pattern of the scoring matrix was initially based on experiments showing the relative importance of sequences in and near the nicking enzyme recognition site (not shown) but the actual values used were arbitrary. These sequences were placed in a searchable database consisting of the probe sequence, % GC content, Tm to B. anthracis target and a list of closest matches in GenBank together with their score and Tm (target of 54° C.) and the absence of possible intermolecular or intramolecular stem-loop structures.

Probe Screening Candidate probes were first tested against three near neighbors of the *B. anthracis* genome, *B. cereus, B. subtilis*, and *B. thuringiensis*; any candidate probes showing positive results were eliminated from subsequent screening in order to eliminate to false positive detection in assays for *B. anthracis*. In total, all 133 probes were tested against 14 strains from the 3 near neighbors. Surviving probes were then tested against the eukaryote and prokaryote MDA panels, including various strains of *B. anthracis* MDA. Probes showing positive results for the *B. anthracis* strains only and no cross-reactivity with the background panels were then tested against the 96 MDA pools of 4000 environmental aerosol samples, and subsequently the 54 MDA soil samples. All remaining probes were then retested against the *B. anthracis* strains, prokaryote and eukaryote panels.

Figure 35:
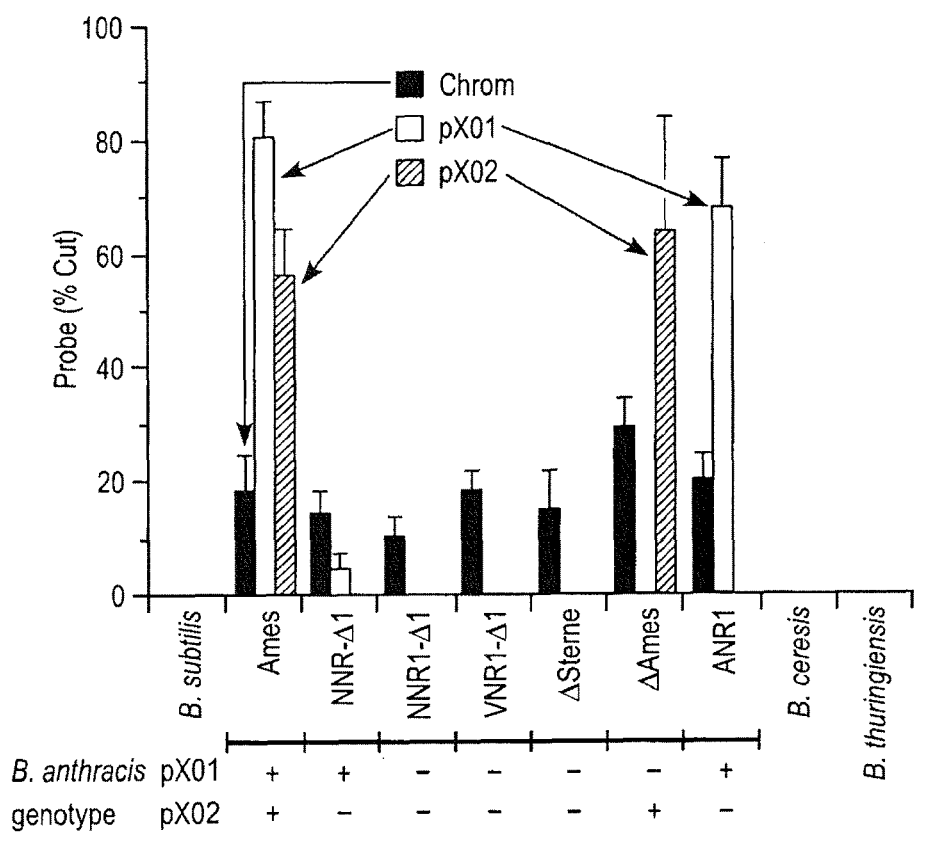

Discrimination between Strains of *B. anthracis* Our large scale screening analysis identified a set of probes that could detect *B. anthracis* chromosomal and plasmid sequences but that did not react with any of the DNAs in our screening panels including over 2000 environmental samples. To test whether these probes could be used to genotype unknown samples correctly, a blinded experiment was performed. DNA samples from a set of *B. anthracis* strains and related *Bacillus* species were coded, amplified, and subjected to NESA at ECBC. These reactions were then analyzed by CE at Georgetown University Medical School, and the results decoded by ECBC. All three related *Bacillus* species tested gave a positive result (FIG. 35). Furthermore, the plasmid content of the strains was determined accurately in all cases.

Parallel and Multiplex NESA For analysis of a large number of probes against one or more organisms, a system that is amenable to parallel, and/or multiplex analysis is essential. For instance, in environmental sampling for pathogens, a whole host of different targets could be envisioned (1). During our large scale screening, analysis was performed with 96 reactions in parallel using 96-well plates and a Beckman Biomek FX robotic liquid handling station. The MDA reaction produces a vast excess of DNA enabling over 100 NESA reactions from a 50 µl MDA reaction and this can be scaled up easily. Although 500 ng of MDA DNA was used in these screening assays, less than 100 ng of MDA DNA is sufficient for NESA (11). To increase the efficiency of the assay even more we developed a multiplex assay using FAM 16 labeled probes specific for *B anthracis* chromosomal and plasmid (pXO1 and pXO2) sequences that could be distinguished from each other by size using capillary electrophoresis. These probes were used in NESA reactions in the presence of MDA amplified genomic DNA from *B. anthracis* and related *Bacillus* species. Capillary electrophoresis readily distinguished cleaved and uncleaved probe both for pXO1 and pX02 and chromosomal DNA in the same assay (FIG. 36). For instance, the Ames strain of *B. anthracis* contains both pX01 and pX02 and thus generates signals from all three probes (chromosomal, pXO1 and pXO2) (FIG. 36 top). In Δ Ames, which contains only pXO2, the pX01, signal is absent. Similarly, the signal for pXO2 is absent in strain NNR-Δ1 that lacks pXO2 (although the pXO1 and chromosomal signals obtained with this strain are lower for an unknown reason). With Δ Sterne, a strain that lacks both plasmids, only the chromosomal signal was observed.

Discussion We have demonstrated that the combination of MDA and NESA can be used to develop fast, sensitive and specific multiplex assays for organism identification. This combination of techniques provides an alternative to PCR, which is sensitive to common environmental inhibitors.

Sensitivity The theoretical sensitivity of our combined MDA/NESA assay is one genome equivalent since it has been shown that MDA can be performed on one bacterium (13, 20). Detection levels of one bacterium are likely to be hard to obtain routinely but we have previously demonstrated the ability to detect 7 cfu of *B. subtilis* in crude samples (11).

Assay Time The slowest step in the assay is the MDA reaction that is routinely run overnight as recommended by the manufacturer. Preliminary results using the new ultrafast kit from Qiagen indicate that a standard MDA reaction yields sufficient DNA for NESA within 90 min. Data provided by Qiagen indicate that sufficient DNA should be produced within 45 min, but we have yet to confirm this. Further increases in speed can be possible by supplementing the reaction with additional enzyme (unpublished) or by using semi-specific primers for the region of the genome under investigation. The sensitivity is also dependent on the type of target DNA since plasmid DNA is usually amplified better in MDA than genomic DNA (6). Plasmid DNA can also give a stronger signal compared to chromosomal DNA due to the higher copy numbers of many plasmids compared to chromosomal DNA. In the case of *B. anthracis*, probes against pXO1 and pXO2 usually gave stronger signals than chromosomal probes.

NESA reactions were run for 1 h here, but have been shown previously to be nearly complete within 30 min (11). Thus a 30 min NESA should be sufficient in all cases except where maximum sensitivity is required. Following NESA, CE separation is complete within 20 min. The use of a 16-capillary machine and a triplex assay would put the through rate at 48 probes in 20 min.

Multiplex Capability We have demonstrated that it is possible to multiplex NESA reactions using size discrimination to detect *B. anthracis* chromosomal, and plasmid (pXO1 and pXO2) DNA in the same assay. Multiplex assays can be designed using different fluors (20), or by placing the fluor on either the 5' (as in this paper) or the 3' end (unpublished) of the probe. Although discrimination by size on CE often has a resolution of less than one base, the small size of the fluorescent oligos used in NESA results in migration that depends on base composition as well as overall length. Multiplex assays must be optimized with regard to the migration pattern of the cleaved probes since fluorescent oligos of different sizes can run at the same position, oligos of the same length can separate into two distinct peaks and oligos of the same length and base composition can resolve into separate peaks when labeled with different fluors (20). For instance, the pX01 and chromosomal probes are cleaved into fluorescent oligonucleotides of identical length yet they resolve on CE (FIG. 6).

Bioinformatics of Probe Selection We designed our bioinformatics pipeline to first identify short regions (24mers) that contained Nt.Alwl sites in *B. anthracis* and then selected against those regions that contained an identical 16 base region, anchored by the Nt.Alwl site, in GenBank. This screening procedure was computationally intense and resulted in a relatively small number of potentially acceptable targets (approximately 2.5%). However, remarkably 17% of these regions yielded probes with absolute specificity in the screening assays conducted suggesting that probe development against other targets is feasible. Indeed, preliminary results with *Y. pestis* chromosomal probes indicate a similar success rate. It should be noted that each Nt.Alwl site can yield multiple probes so that the 136 unique probes analyzed are only a small fraction of what is available. In recent unpublished work, we have successfully made probes against reverse transcribed MS2 bacteriophage (3.85 kb) and Dengue virus genomic RNA (~10.7 Kb) indicating that the MDA/NESA technique can be used on small genomes.

FIG. 31 Design of the Assay The overall design of this exemplary assay is shown in A. DNA first undergoes non-specific whole genome amplification using MDA (5) (B). Following a 95° C. denaturation step the isothermal MDA reaction yields highly concentrated single and double stranded amplified DNA of high molecular weight (Dean et al. 2001). A small fraction of this amplified DNA is then used for specific analysis using NESA (C). MDA DNA is denatured at 95° C. followed by a 58° C. isothermal reaction in which a probe containing a single stranded endonuclease (Nt.Alwl) site anneals to single stranded target DNA and is cleaved by the restriction enzyme. The target remains uncleaved so that upon dissociation of the cut probe, fresh, full-length probe can anneal and be cleaved by the enzyme. This repeated annealing and cleavage of the probe generates a linear amplification of signal from each target sequence (figure adapted from (11).). Cleaved probe is quantified using CE.

FIG. 32 MDA can Amplify DNA from Environmental Collection Filters. *E. coli* (105 cells) in 0.5 μl were added to either 2 μl or 5 μl of 204 BioWatch samples (4% and 10% respectively of the final reaction volume of 50 μl), which were then subjected to MDA. The yield of DNA from the MDA reaction was quantified by PicoGreen assay and compared to controls with 5 μl TE instead of the environmental sample (n=29). Locus representation was determined by TaqMan qPCR on 2 loci, ExoV and OmpA and compared to TE controls (n=29). The upper and lower limits of the box represent the 75th and 25th percentiles, the line within the box is the median value, the filled square is the mean, and the whiskers represent the 90th and 10th percentiles. *Significantly lower than the control p<0.001 (t-test).

FIG. 33 Efficient Detection of Genomic DNA in Crude Environmental Samples by NESA but not by qPCR. The MDA samples generated in FIG. 2 were subjected to NESA (left two panels). The standard 10 μl NESA contained either 1 μl BioWatch sample or 1 μl TE. qPCR reactions were set up containing 4% BioWatch sample as in FIG. 2 and analyzed by qPCR for the OmpA and ExoV markers. The histogram compare the frequency as a percentage of the total with the ranges shown on the figure: 0 represents the number of reactions that gave no detectable signal, > represents reactions that have values above 180, the other values represent the upper limit of a 20% range. Black bar, no signal; grey bar, <80% control; white bar, >80% control.

FIG. 34 Probe Screening. A. Probe Structure and Bioinformatics Screen. Probes contained an Nt.Alwl site 2 bases from the 5' end of the probe. When the probe binds to complementary DNA, Nt.Alwl cuts after 4 bases 3' of the recognition site. The overall length of the probes varied between 18 and 24 bases. The bioinformatics screen yielded a database of 931 potential probes that had a unique 16-base core region. The probes were ordered using a scoring matrix (Table 1) based, in part, on mismatch mutational analysis (not shown). B. Probe validation (experimental screening). Potential probes were screened against MDA genomic DNA as shown in the figure and in Methods. The final 23 probes recognize *B. anthracis* DNA and have never cross-reacted with any other genomic DNA.

FIG. 35 Characterization of Probe Activity on *B. Anthracis* Strains and on Related Species of *Bacillus* Genomic DNA from the Ames strain of *B. anthracis* (our positive control) was amplified by MDA and then analyzed by NESA. Nine genomic DNAs representing 6 *B. anthracis* strains and 3 related *Bacillus* species underwent MDA and NESA at Edgewood Chemical and Biological Command as detailed in Methods except that 4 μl of the MDA reaction was used for NESA. These samples were encoded and then analyzed by CE at Georgetown University. The samples were scored for the presence of *B. anthracis* chromosomal, pXO1 and pXO2 DNA using probes specific for these 3 genetic elements and then the samples were decoded. The genotypes of the *B. anthracis* strains used are shown.

FIG. 36 Performance of a Multiplex Assay for *B. Anthracis* Detection and Genotyping Probes for *B anthracis* chromosomal, pXO1 and pXO2 DNA were used simultaneously in NESA reactions on MDA DNA from the *B. anthracis* strains indicated {methods). The 5-base and 17-base size markers are shown flanking the trace. The uncut probes for chromosomal, pXO1 and pXO2 eluted at 24, 23 and 21 bases The signals from chromosomal, pXOI and pX02 DNA eluted at 24, 23 and 20 bases (not shown) and the cut probes at 10, 9 and 11 bases respectively. The cut pXO1 probe eluted at around 9 bases even though its actual size is 10 bases. The 5mer marker was used as an internal control; the other signals were scaled accordingly.

TABLE 4

| Scoring Matrix | |
|---|---|
| Position | Score |
| 1 | Not scored\ |
| 2 | 0.3 |
| 3-7 | Not scored |
| 8 | 1 |
| 9 | 0.8 |
| 10 | 0.9 |
| 11 | 0.7 |
| 12 | 0.3 |
| 13 | 0.3 |
| Other positions | 0.1 |

The probe design is shown in FIG. 34. Positions 3-7 are the Nt.Alwl site, they are not scored because they have to have an exact match (only exact matches in this region make it through to the scoring matrix).

REFERENCES FOR EXAMPLE 8

1. 2007, posting date. U.S. Government Lists of Bioterrorism Agents and Diseases. Federation of American Scientists. [Online.]
2. Abulencia, C. B., D. L. Wyborski, J. A. Garcia, M. Podar, W. Chen, S. H. Chang, H. W. Chang, D. Watson, E. L. Brodie, T. C. Hazen, and M. Keller. 2006. Environmental whole-genome amplification to access microbial populations in contaminated sediments. Appl Environ Microbiol 72:3291-301.
3. Belec, L., J. Authier, M. C. Eliezer-Vanerot, C. Piedouillet, 1 A. S. Mohamed, and R. K. Gherardi. 1998. Myoglobin as a polymerase chain reaction (PCR) inhibitor: a limitation for PCR from skeletal muscle tissue avoided by the use of *Thermus thermophilus* polymerase. Muscle Nerve 21:1064-7.
4. Bickley, J., J. K. Short, D. G. McDowell, and H. C. Parkes. 1996. Polymerase chain reaction (PCR) detection of *Listeria monocytogenes* in diluted milk and reversal of PCR inhibition caused by calcium ions. Lett Appl Microbiol 22:153-8.

5. Dean, F. B., S. Hosono, L. Fang, X. Wu, A. F. Faruqi, P. Bray-Ward, Z. Sun, Q. Zong, Y. Du, J. Du, M. Driscoll, W. Song, S. F. Kingsmore, M. Egholm, and R. S. Lasken. 2002. Comprehensive human genome amplification using multiple displacement amplification. Proc Natl Acad Sci USA 99:5261-6.
6. Dean, F. B., 3. R. Nelson, T. L. Giesler, and R. S. Lasken. 2001. Rapid amplification of plasmid and phage DNA using Phi 29 DNA polymerase and multiply-primed rolling circle amplification. Genome Res 11:1095-9.
7. Galluzzi, L., M. Magnani, N. Saunders, C. Harms, and I. J. Bruce. 2007. Current molecular techniques for the detection of microbial pathogens. Sci Prog 90:29-50.
8. Gonzalez, J. M., M. C. Portillo, and C. Saiz-Jimenez. 2005. Multiple displacement amplification as a pre-polymerase chain reaction (pre-PCR) to process difficult to amplify samples and low copy number sequences from natural environments. Environ Microbiol 7:1024-8.
9. Hosono, S., A. F. Faruqi, F. B. Dean, Y. Du, Z. Sun, X. Wu, J. Du, S. F. Kingsmore, M. Egholm, and R. S. Lasken. 2003. Unbiased whole-genome amplification directly from clinical samples. Genome Res 13:954-64.
10. Jannes, G., and D. De Vos. 2006. A review of current and future molecular diagnostic tests for use in the microbiology laboratory. Methods MoI Biol 345:1-21.
11. Kiesling, T., K. Cox, E. A. Davidson, K. Dretchen, G. Grater, S. Hibbard, R. S. Lasken, J. Leshin, E. Skowronski, and D. Danielsen. Submitted. Sequence specific detection of DNA using nicking endonuclease signal amplification (NESA). Nucleic acids research.
12. LaMontagne, M. G., F. C. Michel, Jr., P. A. Holden, and C. A. Reddy. 2002. Evaluation of extraction and purification methods for obtaining PCR-amplifiable DNA from compost for microbial community analysis. J Microbiol Methods 49:255-64.
13. Lasken, R. 2005. Multiple displacement amplification from single bacterial cells, p. 119-147. In S. L R. Hughes (ed.), Amplification: Methods Express. Scion Publishing Ltd, Oxford.
14. Lasken, R. 2005. Multiple displacement amplification of genomic DNA, p. 99-118. In S. L. R. Hughes (ed.), Amplification: Methods Express. Scion Publishing Ltd, Oxford.
15. Makino, S., and H. I. Cheun. 2003. Application of the real-time PCR for the detection of airborne microbial pathogens in reference to the anthrax spores. 3 Microbiol Methods 53:141-7.
16. Monis, P. T., and S. Giglio. 2006. Nucleic acid amplification-based techniques for pathogen detection and identification. Infect Genet Evol 6:2-12.
17. Mothershed, E. A., and A. M. Whitney. 2006. Nucleic acid-based methods for the detection of bacterial pathogens: present and future considerations for the clinical laboratory. Clin Chim Acta 363:206-20.
18. Mumy, K. L., and R. H. Findlay. 2004. Convenient determination of DNA extraction efficiency using an external DNA recovery standard and quantitative-competitive PCR. Microbiol. Methods 57:259-68.
19. Peters, R. P., M. A. van Agtmael, S. A. Danner, P. H. Savelkoul, and C. M. Vandenbroucke-Grauls. 2004. New developments in the diagnosis of bloodstream infections. Lancet Infect Dis 4:751-60.
20. Raghunathan, A., H. R. Ferguson, Jr., C. J. Bornarth, W. Song, M. Driscoll, and R. S. Lasken. 2005. Genomic DNA amplification from a single bacterium. Appl Environ Microbiol 71:3342-7.
21. Roh, C, F. Villatte, B. G. Kim, and R. D. Schmid. 2006. Comparative study of methods for extraction and purification of environmental DNA from soil and sludge samples. Appl Biochem Biotechnol 134:97-112.
22. Sachse, K. 2004. Specificity and performance of PCR detection assays for microbial pathogens. MoI Biotechnol 26:61-80.
23. v. Wintzingerode, F., U. B. Gobel, and E. Stackebrandt. 1997. Determination of microbial diversity in environmental samples: pitfalls of PCR-based rRNA analysis. FEMS Microbiology Reviews 21:213-229.
24. Yokouchi, H., Y. Fukuoka, D. Mukoyama, R. Calugay, H. Takeyama, and T. Matsunaga. 2006. Whole-metagenome amplification of a microbial community associated with scleractinian coral by multiple displacement amplification using phi29 polymerase. Environ Microbiol 8:1155-63.

Example 9

Application of Nicking Endonuclease Signal Amplification (NESA) to the Detection of RNA Genomes: Development of a Multiplex Assay for all Four Serotypes of Dengue Virus (References cited in this example are listed at the end of this example.)

Sequence-specific genomic assays for the detection and typing of microorganisms using procedures such as PCR are common. However, in the case of RNA genomes, their small size and the requirement to first copy the RNA into cDNA often limits their sensitivity. We have developed a new assay for organisms with RNA genomes that uses a combination of reverse transcription, multiple displacement amplification (MDA) and nicking endonuclease signal amplification (NESA). This assay, which we term rNESA, achieves high sensitivity, differentiates between viral serotypes, and is insensitive to common environmental and biological contaminants. Using the small RNA virus surrogate MS2 bacteriophage, we were routinely able to detect 100 attograms of genomic RNA with rNESA. At 10 attograms (5genomes) the NESA assay detected MS2 approximately 40% of the time. With the same samples, a published rtPCR assay had a detection threshold of 10 fg genomic RNA (5,000genomes). The presence of a large excess of either human mRNA, or environmental contaminants, had no effect on the specificity of the assay and only a small effect on sensitivity. The utility of the assay for larger RNA viruses was shown by the development of a rNESA multiplex assay specific for the four serotypes of the human pathogenic Dengue virus. These probes had absolute specificity between the Dengue virus serotypes and no cross reactivity with human RNA or with two other members of the Flaviviridae family, West Nile virus and St Louis Encephalitis virus. The Dengue assay detected 2 fg Dengue virus RNA (~345 genome equivalents).

Detection and identification of microorganisms is critical in the areas of medical diagnostics, biodefense and environmental biology. Many detection methods have been used including selective culture in vitro, animal inoculation, mass spectrometry, antibody-dependant assays and assays that use DNA sequence-specific hybridization (Ivnitski et al. 2003; Lim et al. 2005; Peruski and Peruski 2003; Rotz and Hughes 2004). Of the DNA-based techniques, PCR is perhaps most often used because of its high specificity, speed, and its adaptability to new targets. RNA viruses, however, are an exception because there is an additional requirement to first convert the RNA to DNA. This first step, which uses reverse transcriptase, is inefficient and limits the sensitivity of the overall assay (Bustin and Nolan 2004). In qPCR, a relatively small target DNA sequence is amplified using a gene-specific primer pair in sequential rounds of denaturation, annealing, and DNA synthesis using a heat tolerant DNA polymerase. The product of the reaction is detected using fluorescent probes. That is, amplification and detection essentially occur at the same time. We recently separated these two steps by amplifying DNA nonspecifically using MDA and then detecting the presence of specific sequences using NESA (Kiesling et al, 2007). In NESA, a single stranded fluorescent probe containing a nicking endonuclease recognition sequence anneals to the target sequence forming a double stranded recognition and cleavage site. The nicking endonuclease then cleaves the probe but leaves the target intact. The small probe pieces dissociate from the target spontaneously allowing multiple rounds of hybridization and cleavage to occur. The cleaved probe can be detected in a number of ways although we usually use capillary electrophoresis. We have also used FRET-based probes where fluor and quencher are separated upon DNA cleavage (unpublished). A recent paper used cleavage of molecular beacons in their NESA reaction (Li et al. 2008). In this paper, we describe an MDA-NESA protocol (rNESA) that allows detection of RNA viral genomes with a sensitivity that outperforms rtPCR. Remarkably, the assay can also be performed directly on environmental samples such as extracts of BioWatch filters that are refractory to PCR analysis. BioWatch is a US government program that monitors air for biological threat agents using filtration (Report 2003). We demonstrate the power of rNESA by developing a multiplex assay against the four Dengue virus serotypes. Probes against each of the four Dengue serotypes were specific for the respective serotype and did not cross react with other closely related RNA viruses. In addition, the Dengue virus rNESA assays were able to detect low levels of Dengue RNA even in the presence of a large excess of nonspecific (human) RNA.

Results

Detection of Genomic RNA Using Reverse Transcriptase and NESA For the initial experiments, we used MS2 bacteriophage genomic RNA as a target. MS2 is often used as an RNA virus surrogate since there is no risk of infection and it can be handled at biosafety level I (O'Connell et al. 2006). MS2 first strand cDNA was reverse transcribed as detailed in methods. This cDNA was then used in a series of NESA reactions using NESA probes designed to hybridize to either the cDNA (MS2-S) or to the RNA strand itself (MS2-1). As expected, the MS2-S probe recognized the target cDNA and was cleaved by Nt.AlwI as shown by the production of cleaved probe (FIG. 1A). Under these conditions at least 0.1 ng of starting RNA were required. In contrast, the antisense probe MS2-1 failed to detect MS2 RNA either before or after cDNA synthesis. These results were expected since Nt.AlwI is not known to cleave RNA-DNA hybrids. In an attempt to increase the sensitivity of the assay, MS2 cDNA was nonspecifically amplified by MDA and then subjected to NESA. MDA was felt to be a near ideal amplification method since it had been shown previously that MDA using random primers results in low amplification bias and very little loss of specific sequences (Hosono et al. 2003). MDA has even been used to genotype a single bacterium (Raghunathan et al. 2005). The addition of MDA did indeed result in increased NESA sensitivity such that 100 ag of MS2 could be reliably detected (FIG. 1B). At 10 ag, detection varied between replicates. For instance, in FIG. 1B one of three replicates gave a detectable signal. In all, we have performed the analysis on 10 ag MS2 RNA 17 times; a signal was observed in 7 of these, that is approximately 40% of the time. 10 ag corresponds to approximately 5 MS2 genomes. This level of sensitivity is remarkable for an assay using reverse transcriptase. In order to directly compare rNESA with rtPCR, the same MS2 dilutions used in FIG. 1B were subjected to rtPCR with two different primer sets using a recently published protocol (O'Connell et al. 2006). rtPCR reliably detected 10 fg MS2 RNA in this experiment (FIG. 1C). Melting curve analysis indicated specific amplification at 10 fg but not 1 fg of starting RNA. This value is in agreement with the limits of detection shown previously using these primers and it agrees with other primer sets that have been reported independently (Dreier et al. 2005; Rolfe et al. 2007).

rNESA is Resistant to Inhibitors Found in Crude Environmental Samples Detection of genomic DNA or RNA in environmental samples usually requires purification of the genomic material in order to remove contaminants that inhibit enzymatic reactions. In the case of PCR, inhibitors can cause loss of specific signal resulting in false negatives and/or the inappropriate amplification of non-target DNA resulting in false positives (Bustin and Nolan 2004; Lantz et al. 2000; Radstrom et al. 2004). Both scenarios are unacceptable in programs, such as BioWatch (Report 2003), that are designed to detect the release of biowarfare agents in American cities. To compare the effects of contaminants found in crude BioWatch samples on rtPCR and rNESA, a series of MS2 rtPCR and rNESA reactions was set up containing 100 fg MS2 genomic RNA and 10% (v/v) of BioWatch sample. All 14 independent BioWatch extracts inhibited the amplification of MS2 genomic RNA by rtPCR and six of these extracts caused the rtPCR assay to fail completely (FIG. 2A). The BioWatch samples also inhibited rNESA to some extent, but this inhibition was relatively minor (24%) and the rNESA signal was not lost with any BioWatch sample (FIG. 2B). That is, the BioWatch extracts caused dropout (false negatives) in the rtPCR reactions but not in the rNESA reactions.

Sensitivity in a Complex Background (Selectivity) One concern is that a large excess of non-target RNA could decrease rNESA's ability to efficiently amplify and detect some minute quantity of target RNA. To test selectivity, decreasing levels of MS2 genomic RNA (100 fg to 100 ag) were added to rNESA reactions containing 10 or 100 pg of purified total human RNA (FIG. 2C). The MS2-1 probe did not give a signal with human RNA alone as expected. 10 pg of human RNA had little effect on rNESA's ability to detect even the smallest concentration of MS2 RNA (100 ag). Thus rNESA can detect MS2 in the presence of a 100,000-fold excess (w/w) of non-specific RNA. In the presence of 100 pg of human RNA, NESA could again detect MS2 RNA in the presence of a 100,000-fold excess of human RNA but the absolute limit of detection changed to 1 fg (FIG. 2C).

rNESA Probes Specific for Dengue Virus Serotypes To demonstrate that rNESA can be used to detect pathogenic RNA viruses we set out to develop probes specific for each of the 4 Dengue virus serotypes (Chambers et al. 1990). The sequence of the 4 serotype probes and their relationship to the 4 viral serotypes is shown in (FIG. 3A). Each serotype-specific probe was used in a series of rNESA reactions containing 100 fg genomic RNA from each of the viral serotypes. All four serotype-specific probes 1, 2, 3 and 4 were completely specific for DEN-1, DEN-2 and DEN-3, and DEN-4 respectively with no cross reactivity with other serotypes. The specificity of these four probes is further shown by the fact that they do not react with two other members of the *Flavivirus* genus, West Nile virus and Saint. Louis Encephalitis virus. Since the Dengue probes were developed to detect and type Dengue virus in human RNA samples, we repeated the Dengue serotype rNESA assays in the presence of 10 pg or 100 pg of total human RNA (FIG. 4b). As expected, none of the four probes interacted with the human RNA. In addition, added human RNA had little effect on the ability of the probes to detect 100 fg Dengue RNA.

Development of a Multiplex Dengue Virus Assay Initial experiments with the four serotype-specific probes showed that although the signal peaks resolve by capillary electrophoresis (CE), they are not well separated and had some overlap. To obtain signals that are fully separated on CE, two new probes (3T and 4T) were generated that had additional non base pairing residues (T's) at their 3' ends (Table 1) and thus yield larger probe fragments (FIG. 5). All four probes were used in a multiplex rNESA reaction and the signals resolved by CE. All four peaks were distinct from each other. In order to identify peaks and ensure that there was no cross reactivity, a series of reactions were performed that lacked just one of the serotypes. All of the probes could be mapped to a specific peak and there was no cross reactivity (FIG. 5). The sensitivity of the Dengue assay was compared to a published qPCR assay (FIG. 6). Our Dengue rNESA assay detected 2 fg Dengue RNA (approximately 345 Dengue virus genome equivalents) whereas the qPCR assay on the same Dengue virus dilutions had a lower limit of detection of 20 fg. Melting curve analysis showed that there was no detectable specific amplification in the control and 2 fg PCR experiments.

Discussion We have described a new technique that can be used to develop specific assays for the detection of organisms with RNA genomes. The technique, which is a combination of reverse transcription, MDA and NESA, retains the properties of the individual techniques.

For instance the inhibitor-resistant phi29 DNA polymerase in MDA allows detection in dirty backgrounds and fast, nonspecific whole genome amplification while the moderate temperature resistance of Nt.Alwl (up to 60° C.) allows the development of specific DNA probes. Remarkably, the assay is more sensitive than rtPCR both for the small (3.579 kb) virus substitute, MS2 and for the larger (~10.7 kb) Dengue virus.

Sensitivity We have shown that rNESA can detect 100 ag of MS2 RNA routinely and 10 ag about 40% of the time. 10 ag is equivalent to approximately 5 genomes. A surprising finding was that rNESA was more sensitive than published rtPCR MS2 assays (Dreier et al. 2005; O'Connell et al. 2006; Rolfe et al. 2007). This is probably due to the nature of the cDNA synthesized in the reverse transcriptase step. Reverse transcription is dependent on an initial DNA primer that initiates cDNA synthesis. Since the ability of primers to initiate productive cDNA synthesis is highly dependent on the location of hybridization due to folding of the RNA, random primers are often used to sample many initiation sites (Bustin and Nolan 2004). Although this results in relatively efficient cDNA synthesis, most cDNA molecules are not full length. This reduces the ability of PCR to amplify the cDNA because some cDNA molecules will not contain sequences having both forward and reverse priming sites. These sequences will not act as templates for PCR and thus limits of detection will decrease. This is not the case for rNESA because neither amplification of the cDNA with MDA, nor amplification of the signal with NESA, requires a primer pair. It is possible that the NESA target sequence (approximately 20 bases) can be split in two resulting in loss of signal but this will occur far less frequently than separation of the forward and reverse primers of rtPCR that can be 100 or more nucleotides apart. For the same reason, NESA can be less sensitive to degradation of the RNA during analysis. The Dengue virus assay was not as sensitive as the MS2 assay. We do not know if this is related to the larger size of the Dengue virus. However, the Dengue rNESA assay was still approximately 10-fold more sensitive than the qPCR assay.

Specificity We have previously shown that NESA probes can be used to distinguish between bacterial species (Kiesling et al. 2007). Here, we show that it is possible to develop specific probes against the closely related serotypes of Dengue virus. These probes not only distinguish between Dengue serotypes but they also do not interact with West Nile virus and St. Louis Encephalitis virus that are also members of the *Flavivirus* genus. Both the Dengue and MS2 probes are also refractive to total human RNA. We are currently developing probes that are specific for groups of organisms. For instance we are developing a probe that recognizes all Dengue virus serotypes and another that recognizes many of the members of the *Flavivirus* genus.

Selectivity We show that rNESA selectively detects 100 ag of MS2 genomic RNA (~50 genomes) in the presence of 10 pg total human RNA. 10 pg of human RNA is the approximate amount of RNA in 2 to 10 cells, thus the assay can theoretically detect the equivalent of 5 viral genomes per human cell. With 100 pg of human RNA there was a decrease in sensitivity of the assay presumably due to competition between the human RNA and MS2 RNA for reverse transcriptase. It would be interesting to see if the use of MS2-specific reverse transcriptase primers results in increased sensitivity in the presence of such a large excess of human RNA.

Application to Environmental Monitoring and Medical Diagnostics In both of these applications, samples are often contaminated with potential inhibitors. Heme in blood samples, for instance, is a well-known inhibitor of PCR as is humic acid from soil in environmental assays (Radstrom et al. 2004). For this reason, samples often undergo extensive purification before enzymatic analysis. We have shown that crude environmental samples that are refractory to rtPCR analysis can be assayed with rNESA with little loss of sensitivity and no drop out. That is, rNESA is particularly resistant to enzymatic inhibitors and thus the genomic RNA does not need to be extensively purified.

Dengue Multiplex Assay The Dengue multiplex assay we have described discriminates between all four dengue serotypes, does not interact with the related viruses SLE and WNV, and is applicable to samples containing human RNA. The assay should thus be useful to detect acute Dengue virus infection since detectable viral RNA coincides with the onset of viraemia. Saxena In our rNESA Dengue multiplex assay we can detect 345 genome equivalents. Saxena et al. (Saxena et al. 2008) recently described a multiplex assay for Dengue serotypes with a sensitivity of 2,500 copies. However, it is hard to directly compare the two assays since the assay described by Saxena et al (Saxena et al. 2008) is based upon in vitro transcription of a small region of the virus compared to our full-length assays, and supporting evidence for their sensitivity data is not shown. The apparent increased sensitivity of the rNESA multiplex assay over this rtPCR multiplex assay warrants further investigation using clinical samples. Indeed, the ability to use crude RNA samples, and the easily automated MDA and NESA reactions (unpublished) would make this an attractive diagnostic assay.

Non-Viral RNA targets Although the work presented in this paper targets viral RNA, the technique we describe should be amenable to any RNA target that can be reverse transcribed. Indeed, the sensitivity of the assay is such that detection of mammalian mRNA targets should be possible.

Methods

Oligonucleotides, genomic RNA and NtAIw1 Oligonucleotides (Table 1) were from Integrated DNA Technologies (Coralville, Iowa,) except the β-actin PCR primers (Stratagene). Probes contained a FAM group at either the 5' or 3' end and were purified by RNAse-free ion exchange HPLC. Oligonucleotide size standards were synthesized with hexachlorofluorescein (HEXTM) at their 5' ends. MS2 genomic RNA was obtained from Roche Applied Science (Indianapolis, Ind.). Dengue virus serotype-3, West Nile virus, and St Louis Encephalitis virus genomic RNAs were obtained from BEI resources (Manassas, Va.). Human total RNA was from Stratagene (Cedar Creek, Tex.). Dengue viral Serotypes 1, 2, and 4 genomic RNAs were synthesized by in vitro transcription using pRS424 plasmids containing full-length genomic cDNA inserts (Polo et al. 1997; Puri et al. 2000). Briefly, the plasmids were linearized immediately after the last stop codon using SacI. Linearized plasmids were gel purified using Qiagen Qiaex II Gel Extraction Kit. 2 pg of purified linear plasmid was used with the Ambion SP6 Megascript Kit. The in vitro transcription reactions were incubated for 4 hrs following the manufacturers instructions. The in vitro transcribed RNA was purified using Qiagen RNeasy Mini Kit. Purified RNA was run on a 0.7% agarose gel for determination of correct size and lack of degradation. RNA concentrations were determined by A260 and with the Invitrogen Molecular Probes Quant-it RiboGreen RNA Assay Kit. Serotypes of the four Dengue virus RNA samples were confirmed using serotype specific primers in rtPCR (Saxena et al. 2008).

Reverse Transcription RNA was reverse transcribed using the Invitrogen Superscript III first strand synthesis kit following manufacturers protocol with slight adjustments. Briefly 2 μl of the RNA was added to the 8 μl annealing reaction containing 15 μM random hexamers (New England BioLabs), and 1 μl of the annealing buffer, incubated at 65° C. for 5 min, and placed on ice for 2 min. 2 μl of the reverse transcriptase and 10 μl of the 2× reaction buffer were added to the 8 μl annealing reaction while on ice. The 20-μl reaction was heated to 25° C. for 10 min, 45° C. for 50 min, followed by 95° C. for 5 min. 10 μl of the 20-μl reaction were used in the proceeding ligation reactions.

Ligation and MDA Ligation and MDA were performed using the Qiagen Whole Transcriptome Kit following the manufacturers instructions except that an additional enzyme inactivation step (95° C. for 5 min) was added following the completion of the ligation reaction. The MDA reaction was performed for eight hours NESA Reaction 2 μl of the 50-μl MDA reaction were used in each 10-μl NESA reaction. The NESA reaction contained 1 μl Restriction Endonuclease Buffer-2 (NEB), 1 μl (1 pmol) probe, 2 μl of target MDA, 5 μl H2O. The 9-μl mixture was heated to 95° C. for 10 min, 4° C. for 10 sec, then 58° C. for 5 min. Once the reaction had reached 58° C., 1 μl Nt.Alwl (NEB, Ipswich, Mass.) was added followed by incubation at 58° C. for 60 min and then 80° C. for 20 min to stop the reaction.

Capillary Gel Electrophoresis Samples were analyzed using an Applied Biosystems 3130x1 Genetic Analyzer with electrokinetic injection as described previously (Kiesling et al. 2007). In brief, NESA reactions were diluted 100-fold with formamide and then 10 μl were used for injection. A set of Hex™-labeled standards (5, 17, 21, 30, and 50mer) was run with each sample to aid in peak identification.

rtPCR and Melting Curve Analysis 2 μl of RNA was mixed with 20 μM of each forward and reverse primer, 25 μl 2× BioRad iScript One-Step Sybr Green Mix, 2 μl of Reverse Transcriptase, and RNAse-free H2O for a total reaction volume of 50 μl. Thermocycling parameters were as follows for the following RNA templates: MS2 RNA: 48° C. for 10 min, 95° C. for 5 min, 40 cycles of 95° C. for 10 sec, 62° C. for 30 sec 72° C. for 30 sec, Dengue viral RNA: 50° C. for 10 min 95° C. for 5 min 40 cycles 95° C. for 10 sec 55° C. for 30 sec 72° C. for 30 sec, Human RNA: 94° C. for 5 min 60° C. for 5 min 72° C. for 1.5 min 35 cycles of 94° C. for 45 sec 60° C. for 45 sec 72° C. for 1.5 min followed by final extension of 72° C. for 10 min. All completed rtPCR runs were followed by a melting curve analysis consisting of the following steps: 95° C. for 1 min 55° C. for 1 min, followed by 80 cycles starting at 55° C. for 10 sec increasing in 0.5° C. increments each cycle. All rtPCR experiments were run and analyzed using the BioRad iQ5 RT-PCR Detection System with iQ5 Optical System Software v1.1.

FIG. 37 rNESA MS2 Assay is More Sensitive than rtPCR. A. MS2 RNA was reverse transcribed and subjected to NESA using either a probe specific for the cDNA (MS2-S) or for RNA itself (MS2-1). The sample marked RNA alone was not reverse transcribed. B. MS2 RNA was reverse transcribed and amplified by MDA. 2 μl of the MDA reaction were used in NESA with the MS2-1 probe. C. The MS2 RNA dilutions used in A were amplified using two sets of published primers (Table 1) (O'Connell et al. 2006). N/A, no specific amplification was detected. D. The rtPCR reactions in C were subjected to melting curve analysis. Reactions with starting RNA levels of 10 fg of RNA or more had similar profiles and only the 10 fg reaction is shown. Neither the no RNA control nor the 1 fg reaction had detectable specific amplification. All reactions were performed in triplicate; the standard deviation is shown. * Significantly different from the no RNA control (T-Test, p<0.01)

Figure 38A:
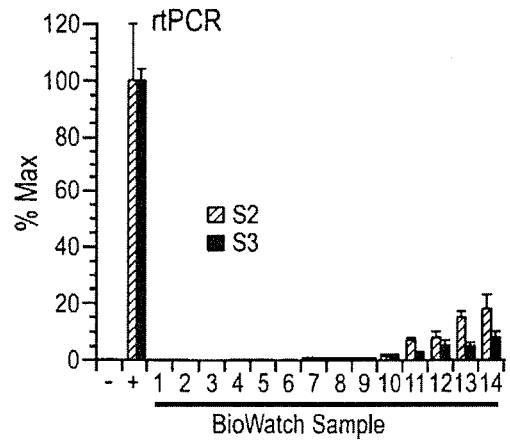
FIGS. 38A-C. Illustrate that rNESA but not rtPCR is resistant to environmental contaminants. rtPCR reactions were set up using 100 fg MS2 RNA and either primer set S2 or S3. A. 10% of the final volume of the reaction contained either TE (−) or an independent crude BioWatch extract (1 to 14). B. rNESA reactions were set up using 100 fg MS2 RNA and probe MS2-1.10% of the final volume of the reaction contained either TE (−) or an independent crude BioWatch extract (1 to 14). C. rNESA reactions were set up containing decreasing concentrations of MS2 RNA and the MS-1 probe and either 1 or 10 pg of human RNA. All reactions were performed in triplicate; standard deviation is shown.* Significantly different (T-Test) from the no RNA control (p<0.01).
Figure 38B:
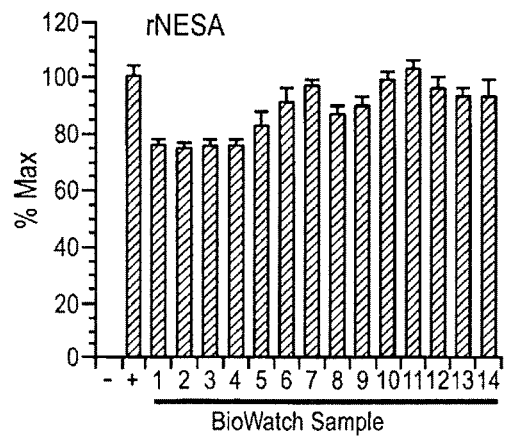
Figure 38C:
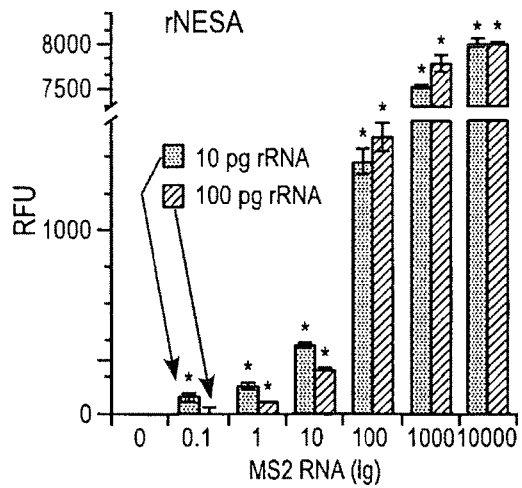

FIG. 38. rNESA but not rtPCR is Resistant to Environmental Contaminants. A. rtPCR reactions were set up using 100 fg MS2 RNA and either primer set S2 or S3.10% of the final volume of the reaction contained either TE (−) or an independent crude BioWatch extract (1 to 14). B. rNESA reactions were set up using 100 fg MS2 RNA and probe MS2-1. 10% of the final volume of the reaction contained either TE (−) or an independent crude BioWatch extract (1 to 14). C. rNESA reactions were set up containing decreasing concentrations of MS2 RNA and the MS-1 probe and either 1 or 10 pg of human RNA. All reactions were performed in triplicate; standard deviation is shown.* Significantly different (T-Test) from the no RNA control (p<0.01).

Figure 39:
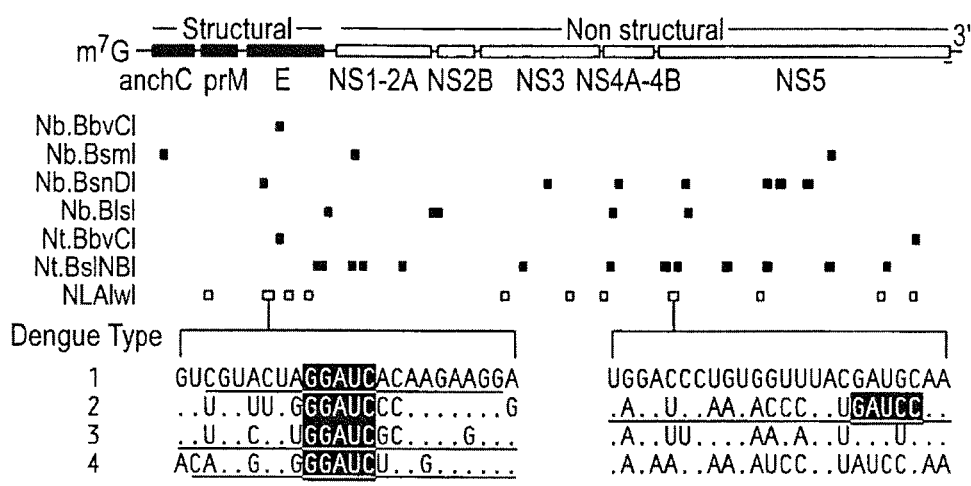
FIG. 39. Illustrates the dengue virus genome organization and exemplary probe location.

FIG. 39. Dengue Virus Genome Organization and Probe Location. Locations of selected nicking endonuclease recognition sites are shown relative to the gene structure of the Dengue genome. The two regions used for Nt.Alwl probe development are shown together with the RNA sequence of the four Dengue serotypes. Underlined blue and green underlined regions were used as sense and antisense DNA probes respectively (Table 1). Nt.Alwl sites are shown in red. AnchC, anchored capsid protein; prM, membrane precursor protein; E envelope (E) protein; NS, nonstructural protein (1, 2A, 2B, 3, 4A, 4b, 5).

Figure 40A:
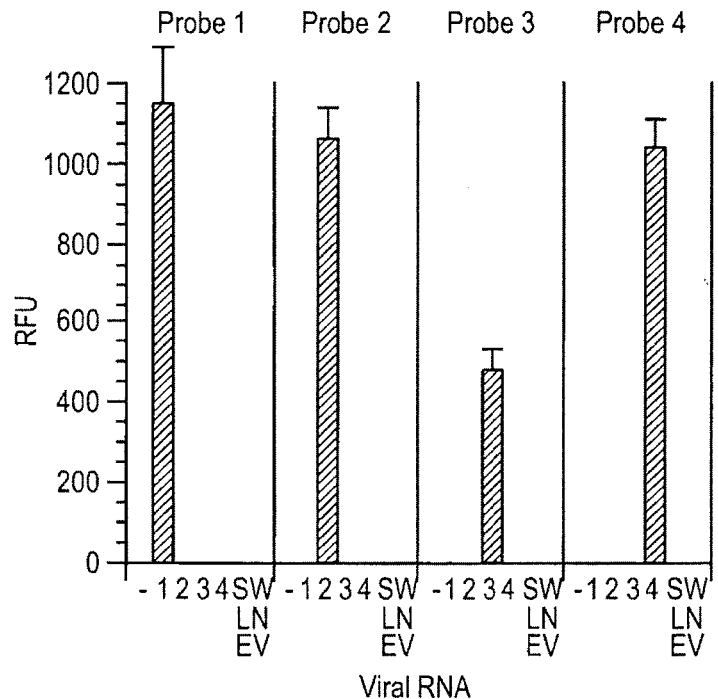
FIG. 40. Illustrates a dengue virus serotype-specific rNESA assay. A. Each serotype-specific probe (probes 1 to 4) were used independently in a set of rNESA reactions containing no RNA (−), 100 fg genomic RNA from Dengue serotypes 1 to 4 (1-4), St Louis Encephalitis virus (SLE) or West Nile virus (WNV) genomic RNA. B. Each serotype-specific Dengue probe was used with its cognate Dengue RNA in rNESA reactions containing 0, 10 or 100 pg total human RNA.
Figure 40B:
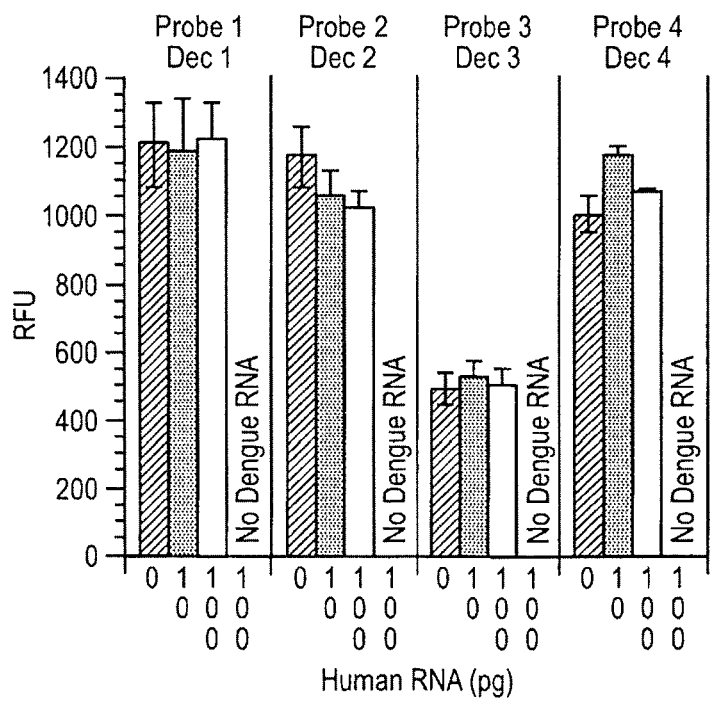

FIG. 40. Dengue Virus Serotype-Specific rNESA Assay. A. Each serotype-specific probe (probes 1 to 4) were used independently in a set of rNESA reactions containing no RNA (−), 100 fg genomic RNA from Dengue serotypes 1 to 4 (1-4), St Louis Encephalitis virus (SLE) or West Nile virus (WNV) genomic RNA. B. Each serotype-specific Dengue probe was used with its cognate Dengue RNA in rNESA reactions containing 0, 10 or 100 pg total human RNA.

Figure 41:
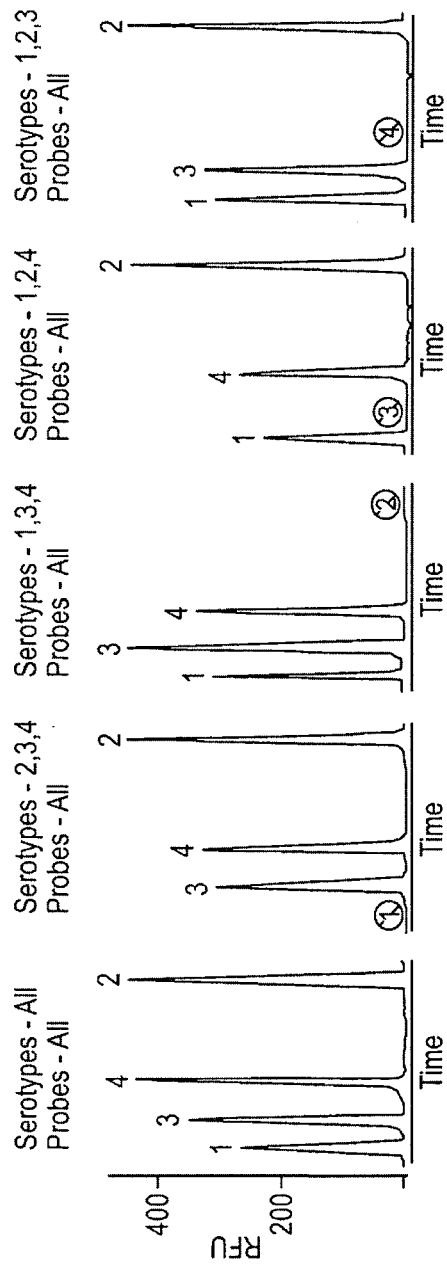
FIG. 41. Illustrates a dengue multiplex assay.

FIG. 41. Dengue Multiplex Assay Dengue serotype-specific multiplex probes (Dengue 1, 2, 3T, 4T) were used in a multiplex assay containing all four Dengue serotypes (first panel) or in assays missing one of the serotypes. The peak locations corresponding to each probe are shown underneath traces of the capillary electrophoresis analysis. The data has been normalized to a 5 bp HEX-labeled size and loading control oligonucleotide (not shown).

Figure 42A:
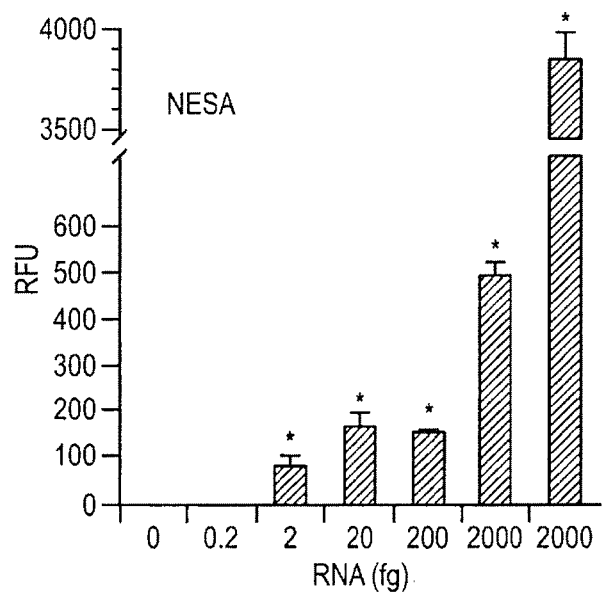
FIG. 42. Illustrates the sensitivity of the example Dengue rNESA assay. Serial dilutions of Dengue serotype 4 RNA were subjected to rNESA using the DEN4 probe (A) or to rtPCR using primers described by Saxena et al. (Saxena et al. 2008) (B). All reactions were performed in triplicate; averages and standard deviations are shown. After rtPCR, samples were subjected to melting curve analysis; the absence of specific amplification is denoted by N/A. *, significantly different from control (T-Test, p<0.01).
Figure 42B:
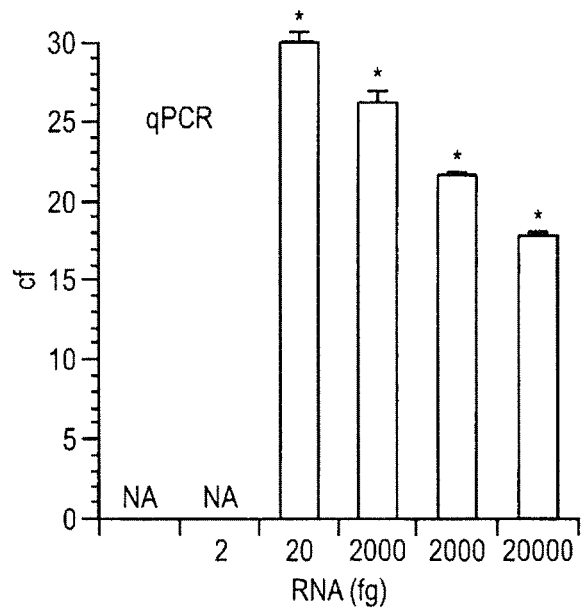

FIG. 42. Sensitivity of the Dengue rNESA Assay Serial dilutions of Dengue serotype 4 RNA were subjected to rNESA using the DEN4 probe (A) or to rtPCR using primers described by Saxena et al., (Saxena et al. 2008) (B). All reactions were performed in triplicate; averages and standard deviations are shown. After rtPCR, samples were subjected to melting curve analysis; the absence of specific amplification is denoted by N/A. *, significantly different from control (T-Test, p<0.01).

TABLE 5

Oligonucleotide Sequences

NESA Probes

MS2-1    5'-FAM-TGGATCTGACATACCTCCGA-3'

MS2-S    5'-CCGTGGATCAGACACGC-FAM-3'

Dengue-1  5'-CGTACTAGGATCACAAGAAGGA-FAM-3'

Dengue-2  5'-FAM-TTGGATCATAGGGTATTGGATCTA-3'

Dengue-3  5'-GTTGTCCTTGGATCGCAAGAGGGA-FAM-3'

Dengue-3T 5'-GTTGTCCTTGGATCGCAAGAGGGATT-FAM-3'

Dengue-4  5'-AGTGCTGGGATCTCAGGAAGGA-FAM-3'

Dengue-4T 5'-AGTGCTGGGATCTCAGGAAGGATTTT-FAM-3'

PCR Primers

MS2 Set 2 F: 5'-TGCGTTGCGTAAAGGCGATGAAGA-3'

R: 5'-TTTCCGGCACCAGGTTAATGGTGGTT-3'

MS2 Set 3 F: 5'-TGAACTTACACCAGCCCAGCACTT-3'

R: 5'-TTCCGGCACCAGGTTAATGGTGGTTT-3'

Den-universal F: 5-TCAATATGCTAAAACGCGCGAGAAACCG-3'

DEN-1 R: 5'-CGTCTCAGTGATCCGGGGG-3'

DEN-2 R: 5'-CGCCACAAGGGCCATGAACAG-3'

DEN-3 R: 5'-TAACATCATCATGAGACAGAGC-3'

DEN-4 R: 5'-TGTTGTCTTAAACAAGAGAGGTC-3'

β-actin F: 5'-TGACGGGGTCACCCACACTGTGCCCATCTA-3'

R: 5'-CTAGAAGCATTTGCGGTGGACGATGGAGGG-3'

REFERENCES FOR EXAMPLE 9

Bustin, S. A. and T. Nolan. 2004. Pitfalls of quantitative real-time reverse-transcription polymerase chain reaction. *J Biomol Tech* 15: 155-166.

Chambers, T. J., C S. Hahn, R. Galler, and C M. Rice. 1990. Flavivirus genome organization, expression, and replication. *Annu Rev Microbiol* 44: 649-688.

Dreier, J., M. Stormer, and K. Kleesiek. 2005. Use of bacteriophage MS2 as an internal control in viral reverse transcription-PCR assays. *J Clin Microbiol* 43: 4551-4557.

Hosono, S., A. F. Faruqi, F. B. Dean, Y. $Du_1$ Z. Sun, X. Wu, J. Du, S. F. Kingsmore, M. Egholm, and R. S. Lasken. 2003. Unbiased whole-genome amplification directly from clinical samples. *Genome Res* 13: 954-964.

Ivnitski, D., D J. O'Neil, A. Gattuso, R. Schlicht, M. Calidonna, and R. Fisher. 2003. Nucleic acid approaches for detection and identification of biological warfare and infectious disease agents. *Biotechniques* 35: 862-869.

Kiesling, T., K. Cox, E. A. Davidson, K. Dretchen, G. Grater, S. Hibbard, R. S. Lasken, J. Leshin, E. Skowronski, and M. Danielsen. 2007. Sequence specific detection of DNA using nicking endonuclease signal amplification (NESA). *Nucleic Acids Res* 35: e117.

Lantz, P. G., W. Abu al-Soud, R. Knutsson, B. Hahn-Hagerdal, and P. Radstrom. 2000. Biotechnical use of polymerase chain reaction for microbiological analysis of biological samples. *Biotechnol Annu Rev* 5: 87-130.

Li, J. J., Y. Chu, B. Y. Lee, and X. S. Xie. 2008. Enzymatic signal amplification of molecular beacons for sensitive DNA detection. *Nucleic Acids Res* 36: e36.

Lim, D. V., J. M. Simpson, E. A. Kearns, and M. F. Kramer. 2005. Current and developing technologies for monitoring agents of bioterrorism and biowarfare. *Clin Microbiol Rev* 18: 583-607.

O'Connell, K. P., J. R. Bucher, P. E. Anderson, C J. Cao, A. S. Khan, M. V. Gostomski, and J. J. Valdes. 2006. Real-time fluorogenic reverse transcription-PCR assays for detection of bacteriophage MS2. *Appl Environ Microbiol* 72: 478-483.

Peruski, L F., Jr. and A. H. Peruski. 2003. Rapid diagnostic assays in the genomic biology era: detection and identification of infectious disease and biological weapon agents. *Biotechniques* 35: 840-846.

Polo, S., G. Ketner, R. Levis, and B. Falgout. 1997. Infectious RNA transcripts from full-length dengue virus type 2 cDNA clones made in yeast. *J Virol* 71: 5366-5374.

Puri, B., S. Polo, C G. Hayes, and B. Falgout. 2000. Construction of a full length infectious clone for dengue-1 virus Western Pacific, 74 strain. *Virus Genes* 20: 57-63.

Radstrom, P., R. Knutsson, P. Wolffs, M. Lovenklev, and C. Lofstrom. 2004. Pre-PCR processing: strategies to generate PCR-compatible samples. *Mol Biotechnol* 26: 133-146. Raghunathan, A., H. R. Ferguson, Jr., C J. Bornarth, W. Song, M. Driscoll, and R. S. Lasken. 2005. Genomic DNA amplification from a single bacterium. *Appl Environ Microbiol* 71: 3342-3347.

Report, C. R. S. 2003. The BioWatch Program: Detection of Bioterrorism. Congressional Research Service Report Rolfe, K J., S. Parmar, D. Mururi, T. G. Wreghitt, H. JaIaI, H. Zhang, and M. D. Curran. 2007.

An internally controlled, one-step, real-time RT-PCR assay for norovirus detection and genogrouping. *J Clin Virol* 39: 318-321.

Rotz, L. D. and J. M. Hughes. 2004. Advances in detecting and responding to threats from bioterrorism and emerging infectious disease. *Nat Med* 10: S130-136.

Saxena, P., P. K. Dash, S. R. Santhosh, A. Shrivastava, M. Parida, and P. L. Rao. 2008. Development and evaluation of one step single tube multiplex RT-PCR for rapid detection and typing of dengue viruses. *Virol J* 5: 20.

While the methods and articles described herein have been described with reference to specific embodiments, this application is intended to cover those various changes and substitutions that can be made by those of ordinary skill in the art.

REFERENCES

The following publications, as well as all others referenced in the disclosure, are incorporated herein by reference in their entirety:

1. Amann, R. I., Krumholz, L., and Stahl, D. A. (1990) J Bacteriol 172(2), 762-770
2. Zheng, D., Aim, E. W., Stahl, D. A., and Raskin, L. (1996) Appl Environ Microbiol 62(12), 4504-4513
3. Sambrook, J., and Russell, D. (2001) Molecular Cloning: A Laboratory Manual, Third Ed., Cold Spring Harbor Press
4. Higgins, L. S., Besnier, $C_1$ and Kong, H. (2001) Nucleic Acids Res 29(12), 2492-2501
5. Morgan, R. D., Calvet, C, Demeter, M., Agra, R., and Kong, H. (2000) Biol Chem 381(11), 1123-1125
6. Xu, Y., Lunnen, K. D., and Kong, H. (2001) Proc Natl Acad Sci USA 98(23), 12990-12995
7. Molloy, P. L., and Symons, R. H. (1980) Nucleic Acids Res 8(13), 2939-2946
8. Kim, Y. G., Shi, Y., Berg, J. M., and Chandrasegaran, S. (1997) Gene 203(1), 43-49
9. Lasken R S and Egholm M (2003) Whole genome amplification: abundant supplies of DNA from precious samples or clinical specimens. Trends Biotechnol 21, 531-535

What is claimed is:

1. A method for detecting the presence of a target DNA sequence in a single stranded DNA in a test sample, the method comprising:

(a) exposing the test sample to a nicking endonuclease and a full-length DNA probe comprising a recognition sequence for the nicking endonuclease and affixed onto a substrate surface under conditions that would permit sequence-specific hybridization of the full-length DNA probe to the target DNA sequence, wherein the recognition sequence is completely complemented to a fragment in the target DNA sequence, and wherein the complete complementation of the recognition sequence in the full-length DNA probe to the fragment in the target DNA sequence in the hybrid of the full-length DNA probe and the target sequence creates a recognition site for the nicking endonuclease;

(b) cleaving the hybridized full-length DNA probe at the recognition site by the nicking endonuclease, whereby the target DNA sequence remains intact; and (c) detecting the cleaved DNA probe, wherein the presence of the cleaved DNA probe indicates the presence of the target DNA sequence in the test sample.

2. The method of claim 1, wherein the substrate surface onto which the DNA probe is affixed comprises a surface of a plastic or glass bead.

3. The method of claim 1, wherein the substrate surface onto which the DNA probe is affixed comprises a surface of a well in a plate.

4. The method of claim 1, wherein the probe comprises a fluorescent tag that is released from the substrate surface if the probe is cleaved by the nicking endonuclease and the step of observing whether the probe is cleaved by the nicking endonuclease comprises detecting the presence of fluorescent tag released from the substrate surface.

5. The method of claim 1, wherein prior to exposing the test sample comprising single stranded DNA to the nicking endonuclease and the substrate surface onto which the DNA probe is affixed, the substrate surface onto which the DNA probe is affixed is desiccated.

6. The method of claim 1, wherein exposing the test sample comprising single stranded DNA to the nicking endonuclease and the substrate surface onto which a DNA probe is affixed comprises exposing the test sample to a plurality of different beads, each comprising a substrate surface, each different substrate surface comprising a different DNA probe.

7. A method for detecting the presence of a target DNA sequence in a single stranded DNA in a test sample, the method comprising:
(a) exposing the test sample to a full-length DNA probe and a nicking endonuclease under conditions that would permit sequence-specific hybridization of the full-length DNA probe to the target DNA sequence, wherein the probe comprises a recognition sequence for the nicking endonuclease, a fluorescent tag, and a fluorescence quencher, the tag and quencher being situated on different sides of the recognition sequence, wherein the full-length DNA probe includes a first stem portion, a second stem portion, and a loop portion, the first and second stern portions being capable of hybridizing to each other, the first and second stem portions being separated by the loop portion, and the tag and the quencher being located in the full-length DNA probe such that the quencher is effective to quench fluorescent emissions of the tag when the first and second stem portions are hybridized to each other, wherein the recognition sequence is completely complemented to a fragment in the target DNA sequence, and wherein the complete complemented of the recognition sequence in the full-length DNA probe to the fragment in the target DNA sequence in the hybrid of the full-length DNA probe and the target sequence creates a recognition site for the nicking endonuclease;
(b) cleaving the hybridized full-length DNA probe at the recognition site by the nicking endonuclease, whereby the fluorescent emissions are released and the target DNA sequence remains intact; and
(c) detecting the presence of the released fluorescent emissions, wherein the presence of the released fluorescent emission indicates the presence of the target DNA sequence in the sample.

8. The method of claim 7, wherein the recognition sequence for the nicking endonuclease is located in the loop portion.

9. The method of claim 7, wherein the recognition sequence for the nicking endonuclease is located in one stem portion and the other stem portion includes a mismatch so that the probe does not comprise a duplex recognition sequence for the nicking endonuclease.

10. The method of claim 1, wherein the target DNA sequence is unique to a DNA genome of a pathogen, and wherein the presence of the target DNA sequence indicates the presence of the pathogen in the test sample.

11. The method of claim 1, wherein the target DNA sequence corresponds to a RNA sequence unique to a RNA genome of a pathogen, and wherein an RNA molecule in a pathogen sample is used to prepare the single stranded DNA in the test sample in accordance with a method comprising:
(i) performing a reverse transcription procedure capable of reverse transcribing the RNA molecule in the pathogen sample into a complementary DNA molecule; and
(b) performing multiple displacement amplification to amplify the complementary DNA molecule from step (i) to form the single stranded DNA in the test sample;
wherein the presence of the target sequence in the test sample indicates the presence of the pathogen in the pathogen sample.

\* \* \* \* \*

SEQUENCE LISTING

```
<160> NUMBER OF SEQ ID NOS: 55

<210> SEQ ID NO 1
<211> LENGTH: 22
<212> TYPE: DNA
<213> ORGANISM: Artificial Sequence
<220> FEATURE:
<223> OTHER INFORMATION: Synthetic

<400> SEQUENCE: 1
cgtactagga tcacaagaag ga                                          22

<210> SEQ ID NO 2
<211> LENGTH: 24
<212> TYPE: DNA
<213> ORGANISM: Artificial Sequence
<220> FEATURE:
<223> OTHER INFORMATION: Synethtic

<400> SEQUENCE: 2
ttggatcata gggtattgga tcta                                        24

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3
gttgtccttg gatcgcaaga ggga                                        24

<210> SEQ ID NO 4
<211> LENGTH: 26
<212> TYPE: DNA
<213> ORGANISM: Artificial Sequence
<220> FEATURE:
<223> OTHER INFORMATION: Synthetic

<400> SEQUENCE: 4
gttgtccttg gatcgcaaga gggatt                                      26
```

<210> SEQ ID NO 5
<211> LENGTH: 22
<212> TYPE: DNA
<213> ORGANISM: Artificial Sequence
<220> FEATURE:
<223> OTHER INFORMATION: Synthetic

<400> SEQUENCE: 5
agtgctggga tctcaggaag ga                                              22

<210> SEQ ID NO 6
<211> LENGTH: 26
<212> TYPE: DNA
<213> ORGANISM: Artificial Sequence
<220> FEATURE:
<223> OTHER INFORMATION: Synthetic

<400> SEQUENCE: 6
agtgctggga tctcaggaag gatttt                                          26

<210> SEQ ID NO 7
<211> LENGTH: 16
<212> TYPE: DNA
<213> ORGANISM: Artificial Sequence
<220> FEATURE:
<223> OTHER INFORMATION: Synthetic

<400> SEQUENCE: 7
gtggatcaga atgcca                                                     16

<210> SEQ ID NO 8
<211> LENGTH: 16
<212> TYPE: DNA
<213> ORGANISM: Artificial Sequence
<220> FEATURE:
<223> OTHER INFORMATION: Synthetic

<400> SEQUENCE: 8
tggcattctg atccac                                                     16

<210> SEQ ID NO 9
<211> LENGTH: 16
<212> TYPE: DNA
<213> ORGANISM: Artificial Sequence
<220> FEATURE:
<223> OTHER INFORMATION: Synthetic

<400> SEQUENCE: 9
gcggatcagc atgccg                                                     16

<210> SEQ ID NO 10
<211> LENGTH: 16
<212> TYPE: DNA
<213> ORGANISM: Artificial Sequence
<220> FEATURE:
<223> OTHER INFORMATION: Synthetic

<400> SEQUENCE: 10
cggcatgctg atccgc                                                     16

<210> SEQ ID NO 11
<211> LENGTH: 21
<212> TYPE: DNA
<213> ORGANISM: Artificial Sequence
<220> FEATURE:
<223> OTHER INFORMATION: Synthetic

```
<400> SEQUENCE: 11
ccggatctga ggtaacgatg t                                               21

<210> SEQ ID NO 12
<211> LENGTH: 16
<212> TYPE: DNA
<213> ORGANISM: Artificial Sequence
<220> FEATURE:
<223> OTHER INFORMATION: Synthetic

<400> SEQUENCE: 12
aggcattctg atccac                                                     16

<210> SEQ ID NO 13
<211> LENGTH: 16
<212> TYPE: DNA
<213> ORGANISM: Artificial Sequence
<220> FEATURE:
<223> OTHER INFORMATION: Synthetic

<400> SEQUENCE: 13
tcgcattctg atccac                                                     16

<210> SEQ ID NO 14
<211> LENGTH: 16
<212> TYPE: DNA
<213> ORGANISM: Artificial Sequence
<220> FEATURE:
<223> OTHER INFORMATION: Synthetic

<400> SEQUENCE: 14
tgccattctg atccac                                                     16

<210> SEQ ID NO 15
<211> LENGTH: 16
<212> TYPE: DNA
<213> ORGANISM: Artificial Sequence
<220> FEATURE:
<223> OTHER INFORMATION: Synthetic

<400> SEQUENCE: 15
tgggattctg atccac                                                     16

<210> SEQ ID NO 16
<211> LENGTH: 16
<212> TYPE: DNA
<213> ORGANISM: Artificial Sequence
<220> FEATURE:
<223> OTHER INFORMATION: Synthetic

<400> SEQUENCE: 16
tggctttctg atccac                                                     16

<210> SEQ ID NO 17
<211> LENGTH: 16
<212> TYPE: DNA
<213> ORGANISM: Artificial Sequence
<220> FEATURE:
<223> OTHER INFORMATION: Synthetic

<400> SEQUENCE: 17
tggcaatctg atccac                                                     16

<210> SEQ ID NO 18
<211> LENGTH: 16
```

```
<212> TYPE: DNA
<213> ORGANISM: Artificial Sequence
<220> FEATURE:
<223> OTHER INFORMATION: Synthetic

<400> SEQUENCE: 18
tggcatactg atccac                                                          16

<210> SEQ ID NO 19
<211> LENGTH: 16
<212> TYPE: DNA
<213> ORGANISM: Artificial Sequence
<220> FEATURE:
<223> OTHER INFORMATION: Synthetic

<400> SEQUENCE: 19
tggcattgtg atccac                                                          16

<210> SEQ ID NO 20
<211> LENGTH: 16
<212> TYPE: DNA
<213> ORGANISM: Artificial Sequence
<220> FEATURE:
<223> OTHER INFORMATION: Synthetic

<400> SEQUENCE: 20
tggcattcag atccac                                                          16

<210> SEQ ID NO 21
<211> LENGTH: 16
<212> TYPE: DNA
<213> ORGANISM: Artificial Sequence
<220> FEATURE:
<223> OTHER INFORMATION: Synthetic

<400> SEQUENCE: 21
tggcattctc atccac                                                          16

<210> SEQ ID NO 22
<211> LENGTH: 16
<212> TYPE: DNA
<213> ORGANISM: Artificial Sequence
<220> FEATURE:
<223> OTHER INFORMATION: Synthetic

<400> SEQUENCE: 22
tggcattctg ttccac                                                          16

<210> SEQ ID NO 23
<211> LENGTH: 16
<212> TYPE: DNA
<213> ORGANISM: Artificial Sequence
<220> FEATURE:
<223> OTHER INFORMATION: Synthetic

<400> SEQUENCE: 23
tggcattctg aaccac                                                          16

<210> SEQ ID NO 24
<211> LENGTH: 16
<212> TYPE: DNA
<213> ORGANISM: Artificial Sequence
<220> FEATURE:
<223> OTHER INFORMATION: Synthetic

<400> SEQUENCE: 24
```

```
tggcattctg atcgac                                                  16

<210> SEQ ID NO 25
<211> LENGTH: 16
<212> TYPE: DNA
<213> ORGANISM: Artificial Sequence
<220> FEATURE:
<223> OTHER INFORMATION: Synthetic

<400> SEQUENCE: 25
tggcattctg atcctc                                                  16

<210> SEQ ID NO 26
<211> LENGTH: 16
<212> TYPE: DNA
<213> ORGANISM: Artificial Sequence
<220> FEATURE:
<223> OTHER INFORMATION: Synthetic

<400> SEQUENCE: 26
tggcattctg atccag                                                  16

<210> SEQ ID NO 27
<211> LENGTH: 19
<212> TYPE: DNA
<213> ORGANISM: Artificial Sequence
<220> FEATURE:
<223> OTHER INFORMATION: Synthetic

<400> SEQUENCE: 27
cttgagtctc gtagagggg                                               19

<210> SEQ ID NO 28
<211> LENGTH: 19
<212> TYPE: DNA
<213> ORGANISM: Artificial Sequence
<220> FEATURE:
<223> OTHER INFORMATION: Synthetic

<400> SEQUENCE: 28
cccctctacg agactcaag                                               19

<210> SEQ ID NO 29
<211> LENGTH: 19
<212> TYPE: DNA
<213> ORGANISM: Artificial Sequence
<220> FEATURE:
<223> OTHER INFORMATION: Synthetic

<400> SEQUENCE: 29
ctcctcttct gcactcaag                                               19

<210> SEQ ID NO 30
<211> LENGTH: 19
<212> TYPE: DNA
<213> ORGANISM: Artificial Sequence
<220> FEATURE:
<223> OTHER INFORMATION: Synthetic

<400> SEQUENCE: 30
aattatcctc agcgccttt                                               19

<210> SEQ ID NO 31
<211> LENGTH: 18
<212> TYPE: DNA
<213> ORGANISM: Artificial Sequence
```

<220> FEATURE:
<223> OTHER INFORMATION: Synthetic

<400> SEQUENCE: 31
actcctacgg gaggcagc                                                 18

<210> SEQ ID NO 32
<211> LENGTH: 18
<212> TYPE: DNA
<213> ORGANISM: Artificial Sequence
<220> FEATURE:
<223> OTHER INFORMATION: Synthetic

<400> SEQUENCE: 32
gacgggcggt gtgtacaa                                                 18

<210> SEQ ID NO 33
<211> LENGTH: 29
<212> TYPE: DNA
<213> ORGANISM: Artificial Sequence
<220> FEATURE:
<223> OTHER INFORMATION: Synthetic

<400> SEQUENCE: 33
cggatcttaa ggctacgtct tgaaccgcg                                     29

<210> SEQ ID NO 34
<211> LENGTH: 30
<212> TYPE: DNA
<213> ORGANISM: Artificial Sequence
<220> FEATURE:
<223> OTHER INFORMATION: Synthetic

<400> SEQUENCE: 34
cgcgttcgga tcttaaggct acttaacgcg                                    30

<210> SEQ ID NO 35
<211> LENGTH: 38
<212> TYPE: DNA
<213> ORGANISM: Artificial Sequence
<220> FEATURE:
<223> OTHER INFORMATION: Synthetic

<400> SEQUENCE: 35
ccggatctta aggctacgtc ttaaacctta attaccgg                           38

<210> SEQ ID NO 36
<211> LENGTH: 21
<212> TYPE: DNA
<213> ORGANISM: Artificial Sequence
<220> FEATURE:
<223> OTHER INFORMATION: Synthetic

<400> SEQUENCE: 36
gctaacttgc ggatcttaag g                                             21

<210> SEQ ID NO 37
<211> LENGTH: 20
<212> TYPE: DNA
<213> ORGANISM: Artificial Sequence
<220> FEATURE:
<223> OTHER INFORMATION: Synthetic

<400> SEQUENCE: 37
aggatcttac gaaacttcgg                                               20

<210> SEQ ID NO 38
<211> LENGTH: 18
<212> TYPE: DNA
<213> ORGANISM: Artificial Sequence
<220> FEATURE:
<223> OTHER INFORMATION: Synthetic

<400> SEQUENCE: 38
aggatcttac gaaacttc                                                 18

<210> SEQ ID NO 39
<211> LENGTH: 21
<212> TYPE: DNA
<213> ORGANISM: Artificial Sequence
<220> FEATURE:
<223> OTHER INFORMATION: Synthetic

<400> SEQUENCE: 39
aggatcttac gataacttcg g                                             21

<210> SEQ ID NO 40
<211> LENGTH: 21
<212> TYPE: DNA
<213> ORGANISM: Artificial Sequence
<220> FEATURE:
<223> OTHER INFORMATION: Synthetic

<400> SEQUENCE: 40
aggatcttac gaaatcttcg g                                             21

<210> SEQ ID NO 41
<211> LENGTH: 21
<212> TYPE: DNA
<213> ORGANISM: Artificial Sequence
<220> FEATURE:
<223> OTHER INFORMATION: Synthetic

<400> SEQUENCE: 41
aggatcttac gaaactttcg g                                             21

<210> SEQ ID NO 42
<211> LENGTH: 21
<212> TYPE: DNA
<213> ORGANISM: Artificial Sequence
<220> FEATURE:
<223> OTHER INFORMATION: Synthetic

<400> SEQUENCE: 42
aggatcttac gaaacttcgg t                                             21

<210> SEQ ID NO 43
<211> LENGTH: 20
<212> TYPE: DNA
<213> ORGANISM: Artificial Sequence
<220> FEATURE:
<223> OTHER INFORMATION: Synthetic

<400> SEQUENCE: 43
tggatctgac atacctccga                                               20

<210> SEQ ID NO 44
<211> LENGTH: 17
<212> TYPE: DNA
<213> ORGANISM: Artificial Sequence
<220> FEATURE:
<223> OTHER INFORMATION: Synthetic

<400> SEQUENCE: 44
ccgtggatca gacacgc                                                          17

<210> SEQ ID NO 45
<211> LENGTH: 24
<212> TYPE: DNA
<213> ORGANISM: Artificial Sequence
<220> FEATURE:
<223> OTHER INFORMATION: Synthetic

<400> SEQUENCE: 45
tgcgttgcgt aaaggcgatg aaga                                                  24

<210> SEQ ID NO 46
<211> LENGTH: 26
<212> TYPE: DNA
<213> ORGANISM: Artificial Sequence
<220> FEATURE:
<223> OTHER INFORMATION: Synthetic

<400> SEQUENCE: 46
tttccggcac caggttaatg gtggtt                                                26

<210> SEQ ID NO 47
<211> LENGTH: 24
<212> TYPE: DNA
<213> ORGANISM: Artificial Sequence
<220> FEATURE:
<223> OTHER INFORMATION: Synthetic

<400> SEQUENCE: 47
tgaacttaca ccagcccagc actt                                                  24

<210> SEQ ID NO 48
<211> LENGTH: 26
<212> TYPE: DNA
<213> ORGANISM: Artificial Sequence
<220> FEATURE:
<223> OTHER INFORMATION: Synthetic

<400> SEQUENCE: 48
ttccggcacc aggttaatgg tggttt                                                26

<210> SEQ ID NO 49
<211> LENGTH: 28
<212> TYPE: DNA
<213> ORGANISM: Artificial Sequence
<220> FEATURE:
<223> OTHER INFORMATION: Synthetic

<400> SEQUENCE: 49
tcaatatgct aaaacgcgcg agaaaccg                                              28

<210> SEQ ID NO 50
<211> LENGTH: 19
<212> TYPE: DNA
<213> ORGANISM: Artificial Sequence
<220> FEATURE:
<223> OTHER INFORMATION: Synthetic

<400> SEQUENCE: 50
cgtctcagtg atccgggggg                                                       19

<210> SEQ ID NO 51

```
<211> LENGTH: 21
<212> TYPE: DNA
<213> ORGANISM: Artificial Sequence
<220> FEATURE:
<223> OTHER INFORMATION: Synthetic

<400> SEQUENCE: 51
cgccacaagg gccatgaaca g                                              21

<210> SEQ ID NO 52
<211> LENGTH: 22
<212> TYPE: DNA
<213> ORGANISM: Artificial Sequence
<220> FEATURE:
<223> OTHER INFORMATION: Synthetic

<400> SEQUENCE: 52
taacatcatc atgagacaga gc                                             22

<210> SEQ ID NO 53
<211> LENGTH: 23
<212> TYPE: DNA
<213> ORGANISM: Artificial Sequence
<220> FEATURE:
<223> OTHER INFORMATION: Synthetic

<400> SEQUENCE: 53
tgttgtctta aacaagagag gtc                                            23

<210> SEQ ID NO 54
<211> LENGTH: 30
<212> TYPE: DNA
<213> ORGANISM: Artificial Sequence
<220> FEATURE:
<223> OTHER INFORMATION: Synthetic

<400> SEQUENCE: 54
tgacggggtc acccacactg tgcccatcta                                     30

<210> SEQ ID NO 55
<211> LENGTH: 30
<212> TYPE: DNA
<213> ORGANISM: Artificial Sequence
<220> FEATURE:
<223> OTHER INFORMATION: Synthetic

<400> SEQUENCE: 55
ctagaagcat ttgcggtgga cgatggaggg                                     30
```